US009451773B2

(12) United States Patent
Fefer et al.

(10) Patent No.: US 9,451,773 B2
(45) **Date of Patent: *Sep. 27, 2016**

(54) PARAFFINIC OIL-IN-WATER EMULSIONS FOR CONTROLLING INFECTION OF CROP PLANTS BY FUNGAL PATHOGENS

(75) Inventors: Michael Fefer, Whitby (CA); Jun Liu, Oakville (CA)

(73) Assignee: Suncor Energy Inc., Calgary, Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/123,716

(22) PCT Filed: Jun. 4, 2012

(86) PCT No.: PCT/CA2012/050376

§ 371 (c)(1), (2), (4) Date: Dec. 3, 2013

(87) PCT Pub. No.: WO2012/162846
PCT Pub. Date: Dec. 6, 2012

(65) Prior Publication Data

US 2014/0107070 A1 Apr. 17, 2014

Related U.S. Application Data

(60) Provisional application No. 61/493,118, filed on Jun. 3, 2011, provisional application No. 61/496,500, filed on Jun. 13, 2011.

(51) Int. Cl.

| | |
|---|---|
| *A01N 55/00* | (2006.01) |
| *A01N 43/56* | (2006.01) |
| *A01N 25/04* | (2006.01) |
| *A01N 27/00* | (2006.01) |
| *A01N 43/653* | (2006.01) |

(52) U.S. Cl.
CPC ............... *A01N 43/56* (2013.01); *A01N 25/04* (2013.01); *A01N 27/00* (2013.01); *A01N 43/653* (2013.01); *A01N 55/00* (2013.01)

(58) Field of Classification Search

CPC ...................................................... A01N 55/00

See application file for complete search history.

(56) References Cited

U.S. PATENT DOCUMENTS

| | | | |
|---|---|---|---|
| 2,714,062 | A | 7/1955 | Lockrey et al. |
| 2,786,821 | A | 3/1957 | Gardner et al. |
| 2,870,037 | A | 1/1959 | Converse et al. |
| 3,131,119 | A | 4/1964 | Fordyce et al. |
| 3,426,126 | A | 2/1969 | Thorne et al. |
| 3,615,799 | A | 10/1971 | Gannon et al. |
| 3,689,574 | A | 9/1972 | Engelhart |
| 3,799,758 | A | 3/1974 | Franz |
| 3,948,635 | A | 4/1976 | Vachette et al. |
| 3,950,265 | A | 4/1976 | Albrecht et al. |
| 3,997,322 | A | 12/1976 | Ratledge |
| 4,002,628 | A | 1/1977 | Benefiel et al. |
| 4,015,970 | A | 4/1977 | Hennart |
| 4,041,164 | A | 8/1977 | Albrecht et al. |
| 4,094,845 | A | 6/1978 | De Long |
| 4,124,720 | A | 11/1978 | Wenmaekers |
| 4,243,405 | A | 1/1981 | Balasubramanyan et al. |
| 4,431,554 | A | 2/1984 | Baur |
| 4,584,013 | A | 4/1986 | Brunner |
| 4,618,360 | A | 10/1986 | Brunner |
| 4,693,745 | A | 9/1987 | Brunner |
| 4,698,334 | A | 10/1987 | Horriere et al. |
| 4,734,432 | A | 3/1988 | Szego et al. |
| 4,737,515 | A | 4/1988 | Hallenbach et al. |
| 4,761,423 | A | 8/1988 | Szego et al. |
| 4,826,863 | A | 5/1989 | Szego et al. |
| 4,834,908 | A | 5/1989 | Hazen et al. |
| 4,853,026 | A | 8/1989 | Frisch et al. |
| 4,902,333 | A | 2/1990 | Quimby, Jr. |
| 4,971,840 | A | 11/1990 | Boho et al. |
| 5,084,087 | A | 1/1992 | Hazen et al. |
| 5,102,442 | A | 4/1992 | Hazen et al. |
| 5,137,726 | A | 8/1992 | Ogawa |
| 5,178,795 | A | 1/1993 | Roberts |
| 5,229,356 | A | 7/1993 | Tocker |
| 5,238,604 | A | 8/1993 | Hazen et al. |
| 5,308,827 | A | 5/1994 | Sakamoto et al. |
| 5,330,995 | A | 7/1994 | Eicken et al. |

(Continued)

FOREIGN PATENT DOCUMENTS

| | | |
|---|---|---|
| CA | 964482 | 3/1975 |
| CA | 2069311 | 4/1991 |

(Continued)

OTHER PUBLICATIONS

Iowa State University. "Fungicides: Triazoles." (c) 2006. Available from: < http://www.ipm.iastate.edu/ipm/icm/2006/5-30/fungicides.htm >.*

The Seed Site. "Monocots and Dicots." (c) Feb. 24, 2010. Available from: < Available from: < http://web.archive.org/web/20100224074428/http://theseedsite.co.uk/monocothtml >.*

Iowa State University. "Fungicides: Qol Fungicides." (c) 2006. Available from: < http://www.ipm.iastate.edu/ipm/icm/2006/5-22/fungicides.html >.*

U Schutte, G.C., et al. "Application of Azoxystrobin for Control of Benomyl-Resistant *Guignardia citricarpa* on 'Valencia' Oranges in South Africa." Plant Disease. (2003), vol. 87, No. 7, pp. 784-788.*

Material Data Safety Sheet. "Sunspray 6E." (c) Jun. 1, 2009.*

The National Turfgrass Research Initiative. (c) Apr. 2003.*

(Continued)

*Primary Examiner* — Noble Jarrell
*Assistant Examiner* — John S Kenyon
(74) *Attorney, Agent, or Firm* — Fish & Richardson P.C.

(57) ABSTRACT

This disclosure features fungicidal combinations that include a paraffinic oil and an emulsifier. The combinations can further include one or more of the following: pigments, silicone surfactants, anti-settling agents, conventional fungicides such as demethylation inhibitors (DMI) and quinone outside inhibitors (QoI) and water. The fungicidal combinations are used for controlling infection of a crop plant by a fungal pathogen.

35 Claims, 6 Drawing Sheets

(56) References Cited

U.S. PATENT DOCUMENTS

| | | |
|---|---|---|
| 5,336,661 A | 8/1994 | Lucas |
| 5,352,729 A | 10/1994 | Birkhofer et al. |
| 5,362,167 A | 11/1994 | Loftin |
| 5,393,770 A | 2/1995 | Grayson |
| 5,393,791 A | 2/1995 | Roberts |
| 5,409,885 A | 4/1995 | Derian et al. |
| 5,504,054 A | 4/1996 | Murphy |
| 5,547,918 A | 8/1996 | Newton et al. |
| 5,558,806 A | 9/1996 | Policello et al. |
| 5,580,567 A | 12/1996 | Roberts |
| 5,599,768 A | 2/1997 | Hermansky |
| 5,599,804 A | 2/1997 | Mudge |
| 5,643,852 A | 7/1997 | Lucas et al. |
| 5,658,851 A | 8/1997 | Murphy et al. |
| 5,665,672 A | 9/1997 | Lucas |
| 5,668,086 A | 9/1997 | Tadayuki et al. |
| 5,703,016 A | 12/1997 | Magin et al. |
| 5,739,371 A | 4/1998 | O'Lenick, Jr. |
| 5,741,502 A | 4/1998 | Roberts |
| 5,919,858 A | 7/1999 | Loftin |
| 5,958,104 A | 9/1999 | Nonomura et al. |
| 6,033,647 A | 3/2000 | Touzan et al. |
| 6,117,820 A | 9/2000 | Cutler et al. |
| 6,146,652 A | 11/2000 | Gore et al. |
| 6,159,900 A | 12/2000 | Bieringer et al. |
| 6,162,763 A | 12/2000 | Tateno |
| 6,210,656 B1 | 4/2001 | Touzan et al. |
| 6,221,811 B1 | 4/2001 | Policello et al. |
| 6,329,321 B2 | 12/2001 | Okura et al. |
| 6,403,061 B1 | 6/2002 | Candau et al. |
| 6,416,748 B1 | 7/2002 | Candau et al. |
| 6,432,877 B2 | 8/2002 | Okura et al. |
| 6,515,031 B2 | 2/2003 | Fefer |
| 6,673,360 B2 | 1/2004 | Fefer |
| 6,683,030 B2 | 1/2004 | Kober et al. |
| 6,713,518 B1 | 3/2004 | Bessette et al. |
| 6,727,205 B2 | 4/2004 | Brinkman |
| 6,734,202 B2 | 5/2004 | Cotter et al. |
| 6,803,345 B2 | 10/2004 | Herold et al. |
| 6,878,674 B2 | 4/2005 | Kobayashi |
| 6,972,273 B2 | 12/2005 | Sedun et al. |
| 7,135,435 B2 | 11/2006 | Cooper et al. |
| 7,799,343 B2 | 9/2010 | Loughner |
| 7,923,452 B2 | 4/2011 | Birner et al. |
| RE42,394 E | 5/2011 | Mudge |
| 8,076,267 B2 | 12/2011 | Diebold et al. |
| 8,298,990 B2 | 10/2012 | Wu et al. |
| 8,426,343 B2 | 4/2013 | Norton et al. |
| 8,569,210 B2 * | 10/2013 | Fefer et al. ............ 504/191 |
| 8,747,874 B2 | 6/2014 | Fefer |
| 8,748,342 B2 | 6/2014 | Gewehr et al. |
| 8,853,128 B2 | 10/2014 | Fefer et al. |
| 9,044,008 B2 | 6/2015 | Fefer |
| 2001/0019728 A1 | 9/2001 | Basinger et al. |
| 2002/0161057 A1 | 10/2002 | Fefer |
| 2003/0087764 A1 | 5/2003 | Pallas et al. |
| 2003/0187079 A1 | 10/2003 | Fefer |
| 2003/0194454 A1 | 10/2003 | Bessette et al. |
| 2003/0198659 A1 | 10/2003 | Hoffmann et al. |
| 2003/0198696 A1 | 10/2003 | Keen |
| 2004/0132621 A1 | 7/2004 | Frisch et al. |
| 2004/0151749 A1 | 8/2004 | Hasebe et al. |
| 2004/0167034 A1 | 8/2004 | Coote et al. |
| 2004/0192556 A1 | 9/2004 | Schregenberger et al. |
| 2005/0026786 A1 | 2/2005 | Deckwer et al. |
| 2005/0181949 A1 | 8/2005 | Norton et al. |
| 2005/0202102 A1 | 9/2005 | Miller |
| 2005/0233907 A1 | 10/2005 | Nabors et al. |
| 2005/0261379 A1 | 11/2005 | Fefer |
| 2005/0274164 A1 | 12/2005 | Coates et al. |
| 2006/0063676 A1 | 3/2006 | Brigance et al. |
| 2006/0068991 A1 | 3/2006 | Norton et al. |
| 2006/0194699 A1 | 8/2006 | Moucharafieh et al. |
| 2006/0276339 A1 | 12/2006 | Windsor et al. |
| 2006/0282961 A1 | 12/2006 | Hughes |
| 2006/0293188 A1 | 12/2006 | Norton et al. |
| 2007/0184005 A1 | 8/2007 | Policello et al. |
| 2007/0197387 A1 | 8/2007 | Polge |
| 2007/0287720 A1 | 12/2007 | Royalty et al. |
| 2008/0064601 A1 | 3/2008 | Casanello et al. |
| 2008/0085832 A1 | 4/2008 | Fefer et al. |
| 2008/0112909 A1 | 5/2008 | Faler et al. |
| 2008/0153702 A1 | 6/2008 | Voeste et al. |
| 2008/0161367 A1 | 7/2008 | Voeste et al. |
| 2008/0280763 A1 | 11/2008 | Hodge et al. |
| 2008/0293567 A1 | 11/2008 | Birner et al. |
| 2009/0325922 A1 | 12/2009 | Fefer et al. |
| 2010/0016447 A1 | 1/2010 | Fefer |
| 2010/0317527 A1 | 12/2010 | Takeuchi et al. |
| 2011/0306495 A1 | 12/2011 | Samarajeewa et al. |
| 2012/0245232 A1 | 9/2012 | Bousque et al. |
| 2013/0253016 A1 | 9/2013 | Fefer et al. |
| 2013/0303374 A1 | 11/2013 | Fefer et al. |
| 2013/0324620 A1 | 12/2013 | Fefer |
| 2014/0228218 A1 | 8/2014 | Fefer et al. |
| 2014/0256556 A1 | 9/2014 | Fefer et al. |
| 2015/0065475 A1 | 3/2015 | Fefer et al. |
| 2015/0237869 A1 | 8/2015 | Fefer |

FOREIGN PATENT DOCUMENTS

| | | |
|---|---|---|
| CA | 2434848 | 8/2002 |
| CA | 2496142 | 8/2005 |
| CA | 2472806 | 11/2005 |
| CA | 2507482 | * 11/2005 |
| CA | 2209920 | 1/2007 |
| CA | 2562718 | 4/2008 |
| CA | 2605092 | 4/2008 |
| CA | 2625415 | 9/2008 |
| CA | 2748084 | 7/2010 |
| CA | 2839775 A1 | 6/2013 |
| CN | 101238820 | 8/2008 |
| CN | 101304658 | 11/2008 |
| CN | 101390517 | 3/2009 |
| CN | 101473849 | 7/2009 |
| CN | 101998827 | 3/2011 |
| CN | 101773113 | 2/2013 |
| DE | 2511077 | 9/1976 |
| EP | 0 267 778 | 5/1988 |
| EP | 0498231 | 8/1992 |
| EP | 0526206 | 2/1993 |
| EP | 0598515 | 5/1994 |
| EP | 0862857 | 9/1998 |
| EP | 1563734 | 8/2005 |
| GB | 745360 | 2/1956 |
| GB | 747909 | 4/1956 |
| GB | 748422 | 5/1956 |
| GB | 753976 | 8/1956 |
| GB | 758926 | 10/1956 |
| GB | 762866 | 12/1956 |
| GB | 763246 | 12/1956 |
| GB | 765459 | 1/1957 |
| GB | 792045 | 3/1958 |
| GB | 1044895 | 10/1966 |
| GB | 1168913 | 10/1969 |
| GB | 1249674 | 10/1971 |
| GB | 1417364 | 12/1975 |
| GB | 1499397 | 2/1978 |
| GB | 2123819 | 2/1984 |
| GB | 2176493 | 12/1986 |
| JP | 50-063141 | 5/1975 |
| JP | 54-036205 | 11/1979 |
| JP | 55-129213 | 10/1980 |
| JP | 57-028184 | 2/1982 |
| JP | 59-067205 | 4/1984 |
| JP | 59-210007 | 11/1984 |
| JP | 2-138376 | 5/1990 |
| JP | 3-183505 | 8/1991 |
| JP | 3-221576 | 9/1991 |
| JP | 4-128003 | 4/1992 |
| JP | 7-179306 | 7/1995 |
| JP | 8-218225 | 8/1996 |
| JP | 10-29901 | 2/1998 |
| JP | 11-137084 | 5/1999 |

(56) References Cited

FOREIGN PATENT DOCUMENTS

| | | |
|---|---|---|
| JP | 11-349588 | 12/1999 |
| JP | 2006-124337 | 5/2006 |
| JP | 2008-502640 | 1/2008 |
| NL | 8900381 | 9/1990 |
| SU | 1021415 | 6/1983 |
| WO | WO9007272 | 7/1990 |
| WO | WO9312175 | 6/1993 |
| WO | WO9621353 | 7/1996 |
| WO | WO9632010 | 10/1996 |
| WO | WO9632011 | 10/1996 |
| WO | WO9835561 | 8/1998 |
| WO | WO0064257 | 11/2000 |
| WO | WO0221913 | 3/2002 |
| WO | WO0234047 | 5/2002 |
| WO | WO02089573 | 11/2002 |
| WO | WO02096199 | 12/2002 |
| WO | WO03101195 | 12/2003 |
| WO | WO03105587 | 12/2003 |
| WO | WO2004030641 | 4/2004 |
| WO | WO2004080177 | 9/2004 |
| WO | WO2005009132 | 2/2005 |
| WO | WO2005018324 | 3/2005 |
| WO | WO2005055716 | 6/2005 |
| WO | WO2005082137 | 9/2005 |
| WO | WO2007054473 | 3/2007 |
| WO | WO2007117720 | 10/2007 |
| WO | WO2007136597 | 11/2007 |
| WO | WO2008049192 | 5/2008 |
| WO | WO2008073397 | 6/2008 |
| WO | WO2009090181 | 7/2009 |
| WO | WO2009126370 | 10/2009 |
| WO | WO2009139106 | 11/2009 |
| WO | WO2009/155693 | 12/2009 |
| WO | WO 2009155693 A1 * | 12/2009 |
| WO | WO2010043447 | 4/2010 |
| WO | WO2010132169 | 11/2010 |
| WO | WO2011028987 | 3/2011 |
| WO | WO2011070503 | 6/2011 |
| WO | WO2012031355 | 3/2012 |
| WO | 2012/040804 | 4/2012 |
| WO | WO2012055991 | 5/2012 |
| WO | WO2012126094 A1 | 9/2012 |
| WO | WO2012162846 | 12/2012 |
| WO | WO2012171126 | 12/2012 |
| WO | WO2013078546 A1 | 6/2013 |
| WO | WO2014139012 | 9/2014 |

OTHER PUBLICATIONS

Oregon State University. National Forage & Grasslands Curriculum. "Discuss the basics of grass growth." (c) 2008.*
Fertilome. "Broad Spectrum Landscape & Garden Fungicide (32 oz)." (c) Dec. 30, 2010. Available from: < http://web.archive.org/web/20101230174658/http://www.fertilome.com/product.aspx?pid=9950d7c1-dfed-4268-9474-eb508f967dc0 >.*
Beckerman: "Disease Management Strategies for Horticultural Crops Using organic Fungicides", Purdue Extension, Apr. 1, 2008, pp. 1-4, Retrieved from the Internet: URL:https://www.extension.purdue.edu/extmedia/bp/bp-69-w.pdf [retrieved on Sep. 29, 2014].
"Sunspray 6E—Material Safety Data Sheet," Jun. 1, 2009, pp. 1-5, Retrieved from the Internet: URL:http://www.recarroll.com/cw3/Assets/product files/Sunspray 6E.pdf [retrieved on Sep. 30, 2014].
European Search Report issued in European Application No. 127939197.7 on Oct. 13, 2014, 6 pages.
Examination Report in corresponding New Zealand Application No. 618310 on Sep. 30, 2014, 2 pages.
Examination Report in corresponding Australian Application No. 2012262230, dated Jul. 28, 2014, pp. 1-3.
Soomary SD et al., "Evaluation of Fungicides for Control of the Leaf Spot Disease Caused by *Mycosphaerella eumusae* on Banana in Mauritius," Food and Agricultural Research Council, Proceedings Fourth Annual Meeting of Agricultural Scientists. Feb. 2001, pp. 61-65 (Soomary et al.).

Dell, KJ et al., The Efficacy of JMS Stylet-Oil on Grape Powdery Mildew and Botrytis Bunch Rot and Effects on Fermentation. *Am J Enol. Vitic.* 1998, 49, 11-16.
Schutte, GC et al., Application of Azoxystrobin for Control of Benomyl-Resistant *Guignardia citricarpa* on 'Valencia' Oranges in South Africa. *Plant Dis.* 2003, 87, 784-788.
"Auxin," Wikipedia [online]. Retrieved from the Internet: <URL: http://en.wikipedia.org/wiki/Auxin>, 12 pages, Retrieved on Apr. 9, 2015.
Engvild, "Herbicidal activity of 4-chloroindoleacetic acid and other auxins on pea, barley and mustard," Physiologia Plantarum, 96(2):333-337, Feb. 1996.
Holly Frontier®, "Sunspray Oils," 2014 [retrieved on Jul. 27, 2015]. Retrieved from the Internet: <URL: http://www.hollyfrontierlsp.com/Products/Horticultural-Oils/Sunspray-Oils/85/>, 1 page.
BERC Biomass Energy Resource Center, "Grass Energy Basics," 6 pages, 2015.
"Addendum 9. Northeastern Collegiate Weed Science Contest Weed, Crop, and Herbicide Lists," revised May 2007. Retrieved from the Internet: <URL: http://www.newss.org/docs/mop/addendum-9.pdf>, 7 pages.
"An Online Guide to Plant Disease Control," Oregon State University Extension, print 1954, web 1996. Retrieved from the Internet: <URL: http:/plant-disease.orst.edu/>, 7 pages.
"Bentgrass Dead Spot: Ophiosphaerella agrostis," Cornell University, created Apr. 2001, updated Jan. 2015. Retrieved from the Internet: <URL: http://plantclinic.cornell.edu/factsheets/bentgrassdeadspot.pdf>, 2 pages.
"Biological/Biorational Products for Disease Management," University of Connecticut Integrated Pest Management, [online] Jan. 2006. Retrieved from the Internet: <URL: http://www.ipm.uconn.edu/ipm/greenhs/htms/biofung.htm>, 6 pages.
"Characteristics of Plant Growth Regulators used in Fine Turf," Clemson University, retrieved on Aug. 24, 2011. Retrieved from the Internet: <URL: http://www.clemson.edu/extension/horticulture/turf/pest-guidelines/2011-p- est-guidelines/plant growth-reg-2011.pdf>, 9 pages.
"Chemical Update: Plant growth regulators," Grounds Maintenance [online] 2008. Retrieved from the Internet: <URL: http://www.grounds-mag.com/mag/grounds_maintenance_chemical_update_plant_6>, 2 pages.
"Civitas Technical Bulletin—Fungicide Resistance," Petro-Canada. Retrieved from the Internet: <URL: http://www.civitasturf.com/pdf/techBulletin.pdf>, 2 pages, 2009.
"Deformulation of RD 7212 Grazz Greenzit," 5 pages, 2009.
"Dollar Spot on Turfgrass," Cornell University, retreived on Aug. 22, 2011. Retrieved from the Internet: <URL: http://counties.cce.cornell.edu/wyoming/agriculture/resources/ipd/dollar_spot_turfgrass.htm>, 3 pages.
"Emerald® Fungicide A Better Standard For Dollar Spot Control," Jan. 1, 2007 [retrieved on Jan. 14, 2014]. Retrieved from the Internet <URL: http://betterturf.basf.us/products/related-documents/emerald-info-sheet.pdf>, 2 pages.
"Food, Crop & Livestock Safety: Phytotoxicity," British Columbia Ministry of Agriculture. Archived Oct. 27, 2005. Retrieved from the Internet: <URL: http://www.agf.gov.bc.ca/pesticides/e_10.htm>, 2 pages.
"Fungicide Synergy," Kansas State University, Feb. 26, 2009. Retrieved from the Internet: <URL: http://www.ksuturf.com/LISTServArchive/2009-02-26-Fungicide-Synergy.pdf>, 3 pages.
"Gray leaf spot of perennial ryegrass," Kansas State University Turfgrass Research, 4 pages, revised Aug. 2008.
"Heat Stress Study Using Greenzit Pigment," University of Guelph, 3 pages, 2009.
"Herbicide Recommendations for Turfgrass: Postemergence Broadleaf Herbicides," Ontario Ministry of Agriculture, Food and Rural Affairs, Nov. 25, 2002, reviewed May 15, 2006. Retreived from the Internet: <URL: http://www.omafra.gov.on.ca/english/crops/pub75/17turpbh.htm>, 7 pages.
"Herbicide," Wikipedia [online], retrieved on Aug. 29, 2006. Retrieved from the Internet: <http://en.wikipedia.org/wiki/Herbicide>, 5 pages.

(56) References Cited

OTHER PUBLICATIONS

"Horticultural Oils," IPM of Alaska [online] retrieved on Apr. 5, 2005. Retrieved from the Internet: <URL: http:/www.ipmofalaska.com/filed/hortoils.html>, 3 pages.
"Inert (other) Pesticide Ingredients in Pesticide Products," U.S. Environment Protection Agency, retrieved Sep. 11, 2007. Retrieved from the Internet: <http://www.epa.gov/opprd001/inerts/lists.html> 3 pages.
"It pays to be pure," Retrieved from the Internet: <http://www.findarticles.com/p/articles/mi-qa3824/is-200405/ai-n9424665/print>, Meister Media Worldwide, 1 pages, May 2004.
"Kannar Product Range Turf Enhancing Products," 1 page. Retreived on Dec. 14, 2007. Retrieved from the Internet: <URL: http://web.archive.org/web/20040101182326/http:kannar.com/>, 1 page.
"Leaf Spot and Melting-out (crown and root rot) Diseases," Center for Turfgrass Science, Penn State College of Agricultural Sciences, retrieved on Aug. 30, 2011. Retrieved from the Internet: <URL: http://cropsoil.psu.edu/turf/extension/factsheets/managing-diseases/leaf-spot>, 2 pages.
"Performance of generic phosphite fungicides: A status report," AgNet Mar. 8, 2004, The Canadian Phytopathological Society, Retrieved from the Internet: <URL: http://www.cps-scp.ca/pathologynews/performanceofgenericfungicides.html>, 2 pages.
"Plant Growth Regulators for Turf, Landscape and Garden," Lawn Care Academy [online], retrieved Dec. 28, 2010. Retrieved from the Internet: <URL: http://www.lawn-care-academy.com/plant-growth-regulators.html>, 6 pages.
"The Stylet-Oil User's Guide," Retrieved from the Internet: <URL: http://www.stylet-oil.com>, 15 pages. Retreived on Mar. 22, 2005.
"Trinexapac-ethyl—Compound Summary," PubChem Public Chemical Database, [online] retrieved on Aug. 25, 2011. Retrieved from the Internet: <URL: http://pubchem.ncbi.nlm.nih.gov/summary/summary.cgi?cid=92421&loc=ec_rcs>, 3 pages.
"Turf grass coloration using hexadentate cobalt phthalocyanine amine complex salts," AN-1976-74211X[40], p. 1, 1975.
"Turfgrass Diseases: Leaf Spots and Tip Blights, Melting Out, Crown and Root Rots," University of Rhode Island Landscape Horticulture Program, 2000. Retrieved from the Internet: <URL: http://www.uri.edu/ce/factsheets/prints/leafspotsetcprint.html>, 3 pages.
"Turfgrass Pest Management Manual: A Guide to Major Turfgrass Pests & Turfgrasses," North Carolina State University, Mar. 26, 2007. Retrieved from the Internet: <URL: http://www.turffiles.ncsu.edu/PDFFiles/004041/Turfgrass_Pest_Management_Manual_A_Guide_to_Major_Turfgrass_Pests_and_Turfgrasses.pdf>, 106 pages.
Aerosil 200, Evonik [online] <URL: http://www.aerosil.com/lpa-productfinder/page/productsbytext/detail.html?pid=1855&lang=en>, Jun. 19, 2012, 1 page.
Agnello, "Petroleum-derived spray oils: chemistry, history, refining and formulation," in Beattie, G.A.C., Watson, D.M., Stevens, M., Spooner-Hart, R. and Rae, D.J. (eds). Spray Oils Beyond 2000—Sustainable Pest & Disease Management. University of Western Sydney, 2002. Retrieved from the Internet: <URL: http://web.entomology.cornell.edu/agnello/assets/1-1_Agnello.pdf>, 17 pages.
Application of SK EnSpray Oil, Chen Zhengdon, Pesticide Science and Administration, 28(10)25-29, Dec. 31, 2007.
Bakke, "Analysis of Issues Surrounding the Use of Spray Adjuvants with Herbicides," Dec. 2002, Revised Jan. 2007. Retrieved from the Internet: <URL: http://www.fs.usda.gov/Internet/FSE_DOCUMENTS/fsbdev3_045552.pdf>, 61 pages.
Beasley and Branham, "Trinexapac-ethyl and Paclobutrazol Affect Kentucky Bluegrass Single-Leaf Carbon Exchange Rates and Plant Growth," *Crop Sci.*, 47:132-138, Jan. 22, 2007.
Ben-Tal, "Effect of Chloro-Aluminum-Phtahalocyanine on the Growth of Lenma gibba G3," *J. Plant Physiol.*, 135(5):635-636, 1989.

Bigelow et al., "Evaluation of Commercially Available Plant Growth Regulator Programs for Creeping Bentgrass Fairway Management," Retrieved from the Internet: <URL: http://www.agry.purdue.edu/turf/report/2003/Page66.pdf>, pp. 66-74, 2003.
Biology and Control of Dollar Spot Disease, Ontario Ministry of Agriculture Food & Rural Affairs, retreived on Aug. 22, 2011. Retrieved from the Internet: <URL: http://www.omafra.gov.on.ca/english/crops/facts/info_turfdollarspot.htm>, 3 pages.
Blenis et al, "Evaluation of Fungicides and Surfactants for Control of Fairy Rings Caused by Marasmius oreades (Bolt ex. Fr.) Fr.," *HortScience*, 32(6):1077-1084, 1997.
Bradley, "Some ways in which a paraffin oil impedes APHID transmission of potato virus Y," *Canadian Journal of Microbiology*, 9(3): 369-380, 1963.
Brochure for Civitas, Petro-Canada, retrieved on Aug. 22, 2011. Retrieved from the Internet: <URL: http://www.civitasturf.com/pdf/CIVITAS-technical-brochure.pdf>, 12 pages.
Brown Patch on Turfgrass *Rhizoctonia* spp., Cornell University Department of Plant Pathology and Plant-Microbe Biology, created Aug. 1999, updated May 2011. Retrieved from the Internet: <URL: http://plantclinic.cornell.edu/factsheets/brownpatch.pdf>, 3 pages.
Brown Patch Rhizoctonia solani, University of Guelph, Nov. 27, 2003. Retrieved from the Internet: <URL: http://www.uoguelph.ca/pdc/Factsheets/PDFs/127TurfBrownPatch.pdf>, 1 page.
Brown Patch, Center for Turfgrass Science, Penn State College of Agricultural Sciences, retrieved on Aug. 30, 2011. Retrieved from the Internet: <URL: http://cropsoil.psu.edu/turf/extension/factsheets/managing-diseases/brown-​-patch>, 3 pages.
Buckley et al., "An Integrated Approach to Insect Management in Turfgrass: Black Cutworm," Rutgers, The State University of New Jersey, Mar. 2010. Retrieved from the Internet: <URL: http://snyderfarm.rutgers.edu/pdfs/BlackCutworms.pdf>, 3 pages.
Burpee and Latin, "Reassessment of Fungicide Synergism for Control of Dollar Spot," *Plant Disease*, 92(4):601-606, 2008.
Burpee et al., Interactive Effects of Plant Growth Regulators and Fungicides on Epidemics of Dollar Spot in Creeping Bentgrass, *Plant Disease*, 80(11):1245-1250, 1996.
Burr and Warren, "Enhancement of Herbicide Activitiy with an Isoparaffinic Oil Carrier," *Weed Science*, 19(6):701-705, Nov. 1971
Burt, "Tolerance of warmseason turf grasses to herbicides," Plantation Field Laboratory Mimeo Report PFL66-1, University of Florida Digital Collections [online] Aug. 1966. Retrieved from the Internet: <URL: http://ufdc.ufl.edu/UF00076427/00001>, 11 pages.
Buss, "Insect Pest Management on Golf Courses," University of Florida. Retrieved from the Internet: <URL: http://edis.ifas.ufl.edu/in410>, 14 pages. Retrieved on Aug. 26, 2011.
Buss, "Insect Pest Management on Turfgrass," University of Florida. Retrieved from the Internet: <URL: http://edis.ifas.ufl.edu/ig001>, 13 pages. Retrieved on Aug. 26, 2011.
Butler, "Cultural practices and their effects upon turf grass growth and stress tolerance," The British and International Golf Greenkeepers Association Limited, Jul. 2006. Retrieved from the Internet: <URL: http://www.bigga.org.uk/about-us/magazine/back-issues/07-2006/cultural-pray-tim-butler/00919.html>, 7 pages.
Bywater, "Plant Growth Regulators: Mode of Action," AGCSA [online] Australian Turfgrass Management vol. 3.3, Jun.-Jul. 2001. Retrieved from the Internet: <URL: http://www.agcsa.com.au/static/atm_articles/html/3_3c.html>, 3 pages.
Cawthon and Pyle, "Use of Plant Growth Regulators to Retard Growth of Bermudagrass and Dallisgrass in the Landscape," Texas A&M University, retrieved Aug. 24, 2011. Retrieved from the Internet: URL:<http://www.tamu-commerce.edu/agscience/res-dlc/turf/pgr.html>, 5 pages.
Chase and Simone, "Phytotoxicity on Foliage Ornamentals Caused by Bactericides and Fungicides," Plant Pathology Fact Sheet, Florida Cooperative Extension Service, Institute of Food and Agricultural Sciences, University of Florida. Retrieved from the Internet: <URL: http://plantpath.ifas.ufl.edultakextpublFactSheetsip-pOO30.pdf>, 8 pages. Retrieved on Aug. 26, 2011.
Chemical Structures, The Bugwood Network, Nov. 7, 2002. Retrieved from the Internet: <URL: http://www.bugwood.org/PAT/22chemicalstructures.html>, 8 pages.

(56) References Cited

OTHER PUBLICATIONS

Christians, "Creative uses for plant growth regulators," *USGA Green Sec. Rec*, 39: 11-13, Sep. 2001/ Oct. 2001.
Clarke et al., "Pest Control Recommendations for Lawn and Turf Areas, 2006" Rutgers NJAES Cooperative Extension, Jul. 13, 2006. Retrieved from the Internet: <URL: http://njaes.rutgers.edu/pubs/publication.asp?pid=e037>, 33 pages.
Cleary Chemical Corporation, "Use of Cleary's Grass Greenzit™," 1 page, 2004.
Cline, "OLR mating disruption just got easier," Western Farm Press [online] Jun. 1, 2001. Retrieved from the Internet: <URL: http://westernfarmpress.com/olr-mating-disruption-just-got-easier>, 4 pages.
Cockerham et al., "Evaluation of Turfgrass Growth Retardant Chemicals," *California Turfgrass Culture*, 23-24, 21(3):23-24, 1971.
Colby, "Calculating synergistic and antagonistic responses of herbicide combinations," *Weeds*, 20-22, 1967.
Coo-Ranger et al., "Ionic silicone surfactants in water-in-silicone oil emulsions containing proteins," *Polymer Preprints*, 45(1):674-675, 2004.
Cortes-Barco et al., "Comparison of induced resistance activated by benzothiadiazole,(2R, 3R)-butanediol and an isoparaffin mixture against anthracnose of Nicotiana benthamiana," *Plant pathology*, 59(4):643-653, 2010.
Cortes-Barco et al., "Induced systemic resistance against three foliar diseases of Agrostis stolonifera by (2R, 3R)-butanediol or an isoparaffin mixture," *Annals of Applied Biology*, 157(2):179-189, 2010.
Corwin, "Integrated Pest Management: Identification & Management of Turfgrass Disease," University of Missouri Extension. Retrieved from the Internet: <URL: http://extension.missouri.edu/p/IPM1029> 56 pages, 2007.
Cranmer et al., "Controlled droplet application (CDA) of fluazifop and sethoxydim for annual and perennial weed control," 1983 Meeting of the Weed Science Society of America, 1983, 23-24, Weed Abstract vol. 033 Abs. (No. 00871).
Cranshaw, "Clover and Other Mites of Turfgrass," Colorado State University Extension. Dec. 2012. Retrieved from the Internet: <URL: http://www.ext.colostate.edu/pubs/insect/05505.html>, 2 pages.
Crocker & Simpson, "Pesticide screening test for the southern chinch bug," *Journal of Economic Entomology*, 74(6):730-731, 1981
Croda, "Volpo," Croda Chemicals Europe Ltd, Jul. 2001. Retrieved from the Internet: <URL: http://www.chservice.ru/download/DC%20Volpo.pdf>, May 2004.
Cropper, "Towards Reducing Fungicide Use in the Control of Dollar Spot (Sclerotinia Homoeocarpa F.T. Bennett) Disease on Creeping Bentgrass (*Agrostis stolonifera* L.)," May 4, 2009, Master of Science Thesis, University of Kentucky. Retrieved from the Internet: <URL: http://archive.uky.edu/handle/10225/1044>, 69 pages.
Danneberger and Street, "Turfgrass Growth Substances," *Golf Course Management*, Apr. 1990, 58(4):80, 82, 86, 88.
Datapak for SALVO herbicide, United Agri Products Canada Inc., 14 pages, Oct. 2005.
Dickey, "Using plant growth regulators in turfgrass management. (Green Science).," Golfscape [online] Sep. 1, 2002. Retrieved from the Internet: <URL: http://www.highbeam.com/doc/1G1-105617663.html/print>, 2 pages.
Diesburg, "Effects of Turf Colorants and FES04 on Spring Greenup of Zoysiagrass," 1990. Retrieved from the Internet: <URL: http://www.turf.uiuc.edu/research/summaries/1990/effect_colorant.pdf>, 2 pages.
Dokkuma, "Plant Growth Regulators as a Turfgrass Management Tool," Greenkeeper [online] 2008. Retrieved from the Internet: <URL: http://www.greenkeeper.com/upload/alinea_1425.pdf>, 4 pages.

Dokkuma, Plant Growth Regulators Used in Turfgrass Management, Greenkeeper [online] 2008. Retrieved from the Internet: <URL: http://www.greenkeeper.eu/upload/alinea_1420.pdf>, 4 pages.
Duell, "Turfgrass quality and phytotoxicity affected by growth retardants," Chapter 70. Retrieved from the Internet: <URL: http://archive.lib.msu.edu/tic/its/articles/1985pro749.pdf>, 8 pages. Retreived on Aug. 24, 2011.
Erhan and Nelsen, "Comparisons of volatile organic chemical content of news, sheetfed, and heatset ink formulations," *Journal of the American Oil Chemists' Society*, 78(4):419-422, 2001.
Fasold, "Plant Growth Regulators: More Color, Less Clippings," Irrigation and Green Industry [online], May 15, 2009. Retrieved from the Internet: <URL: http://www.igin.com/article-925-%20plant_growth_regulat.html>, 4 pages.
Fidanza et al., "Evaluation of fungicide and plant growth regulator tank-mix programmes on dollar spot severity of creeping bentgrass," *Crop Protection*, 25(9):1032-1038, 2006.
Fidanza et al., "Use of a Soil Surfactant with Fungicides for Control of Fairy Ring Disease in Turfgrass," *Journal of ASTM International*, 4(4):77-82, 2007.
Fishel, "Plant Growth Regulators," University of Florida, Feb. 2006, Revised Apr. 2009, 5 pages.
Fungicide Resistance Action Committee [FRAC] Code List: Fungicides sorted by mode of Action, Fungicide Resistance Action Committee, retrieved on Aug. 22, 2011. Retrieved from the Internet: <URL: http://www.frac.info/frac/publication/anhang/FRAC%20Code%20List%202011final.pdf>, 10 pages.
Furuta, "Strangers in a Strange Land," California Turfgrass Culture, 21(3):22-23, 1971.
Gaussoin and Branham, "Plant Growth Regulator Effects on Annual Bluegrass/Creeping Bentgrass Competition," Department of Crop & Soil Sciences Michigan State University, pp. 52-56, Jul. 2008. Retrieved from the Internet: <URL: http://archive.lib.msu.edu/tic/mitgc/article/198852a.pdf>.
Gauvrit and Cabanne, "Oils for weed control: Uses and mode of action," *Pesticide Science*, 37(2):147-153, 1993.
Gebhardt et al., "Herbicide application with the controlled droplet applicator when using soybean oil," American Society of Agricultural Engineers, Paper No. 83/1509, 13 pages, 1983.
Gilbert and Kopec, "Spring Greenup of Dormant Non-Overseeded Bermudagrass," University of Arizona College of Agriculture 2004 Turfgrass and Ornamental Research Report. Retrieved from the Internet: <URL: http://ag.arizona.edu/pubs/crops/az1359/az13593c11.pdf>, 4 pages.
Golden Artist Colors, "Pigment Identification Charts," retreived on Sep. 15, 2011. Retrieved from the Internet: <URL: http://www.goldenpaints.com/technicaldata/pigment.php>, 15 pages.
Goodwin and McBrydie, "Effect of surfactants on honey bee survival," *New Zealand Plant Protection*, 53:230-234, 2000.
Grey et al., "Timed Release of Flurprimidol from a Granular Formulation in Mulches and Sand," *HortScience*, 44(2):512-515, 2009.
Grover et al., "Droplet and Vapor Drift from Butyl Ester and Dimethylamine Salt of 2,4-D," *Weed Science*, 20(4): 320-324, Jul. 1972.
Guy et al., "The performance of postemergence grass herbicides applied with sprinkler irrigation," Proceedings of the 39th annual meeting of the Southern Weed Science Society, p. 106, 8A, 1986.
Harmon and Latin, "Gray leaf spot of perennial ryegrass," Plant Health Progress [online]. Retrieved from the Internet: <URL: http://www.plantmanagementnetwork.org/pub/php/diagnosticguide/2003/ryegrass/>, 8 pages, 2003.
Hartzler, "Role of spray adjuvants with postemergence herbicides," Iowa State University Weed Science [online], Mar. 7, 2001, Retrieved from the Internet: <URL: http:/www.weeds.iastate.edu/mgmt/2001/additives.htm>, 3 pages.
Heil and Bostock, "Induced systemic resistance (ISR) against pathogens in the context of induced plant defences," Annals of Botany, 89(5), 503-512, 2002.
Hill, "Silicone surfactants—new developments," *Current opinion in colloid & interface science*, 7(5):255-261, 2002.

(56) References Cited

OTHER PUBLICATIONS

Hodgson, "Armyworms and cutworms in turfgrass," Utah State University Extension, Jun. 2007. Retrieved from the Internet: <URL: http://utahpests.usu.edu/IPM/files/uploads/PDFDocs/factsheet-pdf/armyw-cutw-turf07.pdf>, 3 pages.
Hoffman et al., "Application of Fungicides for Suppression of Fusarium Head Blight (Scab)," North Dakota State University, May 2000. Retreived from the Internet: <URL: http://www.ag.ndsu.edu/pubs/ageng/machine/ae1148.pdf>, 4 pages.
Hoffman, "Analysis of Alcohol and Alkylphenol Polyethers via Packed Column Supercritical Fluid Chromatography," (Doctoral dissertation, Virginia Polytechnic Institute and State University), 2004.
Horn, "Increasing the Effectiveness of Turf Herbicides by Use of Oil," Florida State Horticultural Society, pp. 499-509, 1966.
Horn, "Tolerance of Several Southern Turfgrasses to Various Spray Oils," Florida State Horticultural Society, pp. 494-499, 1966.
Hsiang and Tian, "Chemical Trials for Dollar Spot Disease Control," Summer 2006, Guelph Turfgrass Institute, 2006 Annual Research Report, Retrieved from the Internet <URL: http://131.104.104.3/06anrep/40-42.pdf>, pp. 40-42.
Hsiang et al., "Baseline sensitivity and cross-resistance to demethylation-inhibiting fungicides in Ontario isolates of Sclerotinia homoeocarpa," *European journal of plant pathology*, 103(5):409-416, 1997.
Hsiang et al., "Sensitivity of Sclerotinia homoeocarpa to demethylation-inhibiting fungicides in Ontario, Canada, after a decade of use," *Plant pathology*, 56(3):500-507, 2007.
Huang, "Better Creeping Bentgrass Through Electricity," *GMC*, 2003, pp. 85-86. Retrieved from the Internet: <http://www2.gcsaa.org/gcm/2003/dec03/pdfs/12electricity.pdf>, 2 pages.
Huang, "Plant growth regulators: What and why," *Golf Course Management*, pp. 157-160, Jan. 2007.
Jordan, "Enhanced post-emergence herbicide efficacy with ultra-low volume application," Proceedings of the 48th annual meeting of the Southern Weed Science Society, 48, pp. 208-212, 1995.
Kaminski and Dernoeden, "Dead Spot Disease of Creeping Bentgrass," University of Maryland, Nov. 2003. Retrieved from the Internet: <URL: http://www.hgic.umd.edu/content/documents/TT-14DeadSpot.pdf>, 2 pages.
Kaminski and Dernoeden, "Dead Spot of Creeping Bentgrass and Hybrid Bermudagrass," Plant Management Network [online], Apr. 19, 2005. Retrieved from the Internet: <URL: http://www.plantmanagementnetwork.org/pub/ats/diagnostic/2005/deadspot/>, 8 pages.
Kaminski and Dernoeden, "Understanding Bentgrass Dead Spot," USGA Turfgrass and Environmental Research Online, 2(2):1-7, Jan. 15, 2003. Retrieved rom the Internet: <URL: http://turf.lib.msu.edu/tero/v02/n02.pdf>, 9 pages.
Kaminski, "Bentgrass dead spot," University of Connecticut, Dec. 2006. Retrieved from the Internet: <http://www.turf.uconn.edu/pdf/research/factsheets/Disease_Bentgrass_Dead_Spot.pdf>, 2 pages.
Kopec et al., "Repeat Applications of Paclobutrazole (TGR) Plant Growth Regulator on Overseeded Bermudagrass Turf: Weed Control and Bermudagrass Transition," Turfgrass, Landscape and Urban IPM Research Summary, The University of Arizona. Retrieved from the Internet: <URL: http://ag.arizona.edu/pubs/crops/az1487/14875e.pdf>, pp. 174-196, Feb. 2009.
Kopeck and Gilbert, "Overseed Greens Performance Trials," 6 pages, 1995-1996.
Koppenhofer et al., "An Integrated Approach to Insect Management in Turfgrass: Sod Webworms," Rutgers, The State University of New Jersey, Mar. 2010. Retrieved from the Internet: <URL: http://snyderfarm.rutgers.edu/pdfs/SodWebworms.pdf> 3 pages.
Koppenhofer et al., "An Integrated Approach to Insect Management in Turfgrass: White Grubs," Jun. 2002. Retrieved from the Internet: <URL: https://www.co.somerset.nj.us/pdf/JapBeetleFS.pdf>, 4 pages.
Kremer et al., "Control of Sclerotinia homoeocarpa in turfgrass using effective microorganisms," *Em World J*, 1:16-21, 2000.

Latin and Stewart, "Turfgrass Disease Profiles: Gray Leaf Spot," Purdue University. Retrieved from the Internet: <URL: https://www.extension.purdue.edu/extmedia/BP/BP-107-W.pdtf> Apr. 2008, 2 pages.
Latin, "Turfgrass Disease Profiles: Brown Patch," Purdue University, Retrieved from the Internet: <URL: https://www.extension.purdue.edu/extmedia/BP/BP-106-W.pdf> Apr. 2008, 2 pages.
Latin, "Turfgrass Disease Profiles: Dollar Spot," Purdue University. Retrieved from the Internet: <URL: https://www.extension.purdue.edu/extmedia/BP/BP-105-W.pdf>, Jan. 2010, 3 pages.
Latin, "Turfgrass Disease Profiles: Gray Snow Mold," Purdue University, Retrieved from the Internet: <URL: https://www.extension.purdue.edu/extmedia/BP/BP-101-W.pdf> Jan. 2006, 3 pages.
Latin, "Turfgrass Disease Profiles: Leaf Spot/Melting Out," Purdue University, Retrieved from the Internet: <http://www.ces.purdue.edu/extmedia/bp/bp-103-w.pdf>, Apr. 2008, 2 pages.
Latin, "Turfgrass Disease Profiles: Pink Snow Mold and Microdochium Patch," Purdue University, Retrieved from the Internet: <URL: https://www.extension.purdue.edu/extmedia/BP/BP-102-W.pdf>, Jan. 2006, 3 pages.
Lickfeldt et al., "Implications of repeated trinexapac-ethyl applications on Kentucky bluegrass," *Agronomy Journal*, 93(5):1164-1168, 2001.
Lincoln County Noxious Weed Control, "Herbicide Facts," 2007, Retrieved from the Internet: <URL: http://www.co.lincoln.wa.us/WeedBoard/herbicide/herbicidefacts.pdf>, 22 pages.
Liu, "Cytokinin Effects on Creeping Bentgrass Responses to Heat Stress: I. Shoot and Root Growth," *Crop. Sci.*, 42:457-465, 2002.
Liu, "Painting dormant bermudagrass putting greens," *Golf Course Manage*, 75(11):86-91, 2007.
Lorbeer, "Synergism, Antagonism, and Additive Action of Fungicides in Mixtures," *Phytopathology*, 86(11):1261-1262, 1996.
Material Safety Data Sheet for AGRI-DEX, Helena Chemical Company, 1 page, Apr. 29, 2005.
Material Safety Data Sheet for Banner MAXX, Syngenta Crop Protection, Inc., 5 pages, Aug. 30, 2010.
Material Safety Data Sheet for BLENDEX VHC, Helena Chemical Company, 1 page, Jul. 27, 2000.
Material Safety Data Sheet for Broadcoat Spray Adjuvant, Caltex Australia Limited, 5 pages, Sep. 2003.
Material Safety Data Sheet for Chipco Signature, Bayer CropScience Pty Ltd, May 1, 2007, 6 pages.
Material Safety Data Sheet for Chipco Signature, Bayer CropScience Pty Ltd, Oct. 21, 2002, 7 pages.
Material Safety Data Sheet for Civitas, Petro-Canada Lubricants, Inc., 6 pages, Mar. 21, 2011.
Material Safety Data Sheet for Cleary 3336 Plus, Cleary Chemical Corporation, Feb. 1, 2005, 4 pages.
Material Safety Data Sheet for Daconil 2787, Syngenta Crop Protection Canada, Inc., 7 pages, Dec. 31, 2008.
Material Safety Data Sheet for Daconil Ultrex Fungicide, Syngenta Crop Protection Canada, Inc., 7 pages, Aug. 1, 2009.
Material Safety Data Sheet for FORE 80 WP Rainshield, Dow AgroSciences, Jun. 1, 2001, 9 pages.
Material Safety Data Sheet for FORE Fungicide, Rohm and Haas Company, 9 pages, Oct. 16, 1995.
Material Safety Data Sheet for Grass Greenzit, W.A.Cleary Chemical Corporation, 2 pages, Oct. 1997.
Material Safety Data Sheet for Green Lawnger, Becker Underwood, Inc., 5 pages, Feb. 25, 2009.
Material Safety Data Sheet for Harmonizer, Petro-Canada Lubricants Inc., 6 pages, May 6, 2011.
Material Safety Data Sheet for JMS Stylet-Oil, 4 pages, Mar. 1, 1994.
Material Safety Data Sheet for Kannar Turikare Green, 1 page, Sep. 18, 2007.
Material Safety Data Sheet for Killex Lawn Weed Control Concentate (Ortho), Scotts Canada Ltd., 7 pages, Sep. 13, 2005.
Material Safety Data Sheet for Lambent MFF 159-100, Lambent Technologies Corp., 3 pages, Apr. 4, 2006.
Material Safety Data Sheet for Lambent MFF-199 SW, Lambent Technologies Corp., 3 pages, Jan. 31, 2005.

(56) References Cited

OTHER PUBLICATIONS

Material Safety Data Sheet for PEPTOIL, Drexel Chemical Company, 1 page, Jan. 7, 2005.
Material Safety Data Sheet for Regreen™ Turfgrass Colorant, Precision Laboratories, Inc., 3 pages, Mar. 1, 2010.
Material Safety Data Sheet for Rovral Green GT Flowable Fungicide, Bayer CropScience Inc., 9 pages, Mar. 2, 2011.
Material Safety Data Sheet for Silsurf A008-UP, Siltech Corporation, 4 pages, Aug. 21, 2009.
Material Safety Data Sheet for Surf AC 820, Drexel Chemical Company, 1 page, Jul. 22, 2005.
Material Safety Data Sheet for Sylgard 309 Silicone Surfactant, Dow Corning Corporation, 9 pages, Apr. 5, 2001.
McCarty and Whitwell, "Plant Growth Regulators for Fine Turf," Clemson University, South Carolina, archived Sep. 15, 2009. Retrieved from the Internet: <URL: http://www.clemson.edu/extension/horticulture/turf/pest_guidelines/growth_regulators.html>, 1 page.
McCowan, "Turf Herbicide Rx: Add Oil," Agricultural Chemicals, 23(4):18-21, 1968.
McCullough et al., "Ethephon and Trinexapac-ethyl Influence Creeping Bentgrass Growth, Quality, and Putting Green Performance," Plant Management Network, 2006. Retrieved from the Internet: <URL: http://www.plantmanagementnetwork.org/publats/research/2006/creeping/>, 7 pages.
McCullough et al., "Plant Growth Regulator Regimens Reduce Poa annua Populations in Creeping Bentgrass," *Plant Management Network*, 6 pages, Mar. 4, 2005.
McCullough, "Turfgrass Growth Regulators For Professional Managers," Extension Agronomist-Weed Science, Georgia Turf, retrieved Aug. 25, 2011. Retrieved from the Internet: <URL: http://commodities.caes.uga.edu/turfgrass/georgiaturf/publicat/PCRP2011 /PGR.pdf>, 2 pages.
Meister, Jr., Farm Chemicals, 141(1), pp. 4, 38, 42, 44, 46, 48, 77, 78, 80, 82, 84, 86, 92, 94, 96, Jan. 1978.
Mercier, "Use of the growth regulator paclobutrazol in the management of dollar spot of creeping bentgrass in Minnesota," *Phytoprotection*, 80(2):65-70, 1999.
Mergos et al., "Dielectric properties of nanopowder emulsions in paraffin oil," 2011 IEEE International Conference on Dielectric Liquids, Sep. 8, 2011.
Morris, "A Guide to NTEP Turfgrass Ratings," NTEP.org [online], 2011. Retrieved from the Internet: <URL: http://www.ntep.org/reports/ratings.htm>, 5 pages.
Murphy et al., "Plant Growth Regulators Used in Turfgrass Management," Georgia Turf, retreived on Aug. 25, 2011. Retrieved from the Internet: <http://commodities.caes.uga.edu/turfgrass/georgiaturf/WeedMngt/weedcontrol/PGR.htm>, 10 pages.
Murphy, "Turfgrass Growth Regulators For Professional Managers," Extension Agronomist-Weed Science, Georgia Turf, retrieved Aug. 25, 2011. Retrieved from the Internet: <URL: http://commodities.caes.uga.edu/turfgrass/georgiaturf/Publicat/PCRP2009/PGR.09.pdf>, 1 page.
Nalewaja et al., "Crop origin oils with grass control herbicides." *Proc. North Cent. Weed Control Conf.*, vol. 38, p. 3, 1983 (Abstract).
Nelson and Shearer, "2, 4-D and Mycoleptodiscus terrestris for control of Eurasian watermilfoil," *Journal of Aquatic Plant Management*, 43: 29-34, 2005.
Notice for Mecoprop-P TGAC, Commonwealth of Australia Gazette No. NRA 3, 2 pages, Mar. 6, 2001.
Ostmeyer, "The Color Green," *Golf Course Management*, pp. 40, 44, Aug. 1994.
Palla et al., "Correlation of dispersion stability with surfactant concentration and abrasive particle size for chemical mechanical polishing (cmp) slurries," *Journal of dispersion science and tecnology*, 21(5):491-509, 2000.
Pamphlet for Daconil 2787 Flowable Fungicide, Syngenta Crop Protection Canada, Inc., 9 pages, May 2004.
Pamphlet for Daconil Ultrex Fungicide, Syngenta Crop Protection Canada, Inc., 9 pages, May 2004.
Patton and Latin, "Turfgrass Disease Profiles: Rhizoctonia Large Patch," Purdue University, Retrieved from the Internet: <URL: https://www.extension.purdue.edu/extmedia/BP/BP-117-W.pdf> Feb. 2005, 3 pages.
Pavlista, "Paraffin enhances yield and quality of the potato cultivar Atlantic," *J. Prod. Agric.*, 8(1):40-42, 1995.
Perry, "Ground Covers: Specifications and Costs," *California Turfgrass Culture*, 21(3):21-22, 1971.
Perry, "Silicone Surface-Active Agents," Dow Corning Corporation, 2005. Retrieved from the Internet: <URL: http://www.dowcorning.com/content/publishedlit/26/1365.pdf>, 12 pages.
Pest Control for Professional Turfgrass Managers 2011, North Carolina State University, retrieved on Sep. 15, 2011. Retrieved from the Internet: <URL: http://www.turffiles.ncsu.edu/PDFFiles/004176/AG408PestControl_Prof- essionals.pdf>, 58 pages.
Pesticide Product Label System (PPLS), Search Results for PureSpray Oil 10E, Approval dates Apr. 21, 2000, Jul. 23, 2002, Sep. 24, 2003, Mar. 5, 2004. EPA Office of Pesticide Programs. Retrieved from the Internet: <http://oaspub.epa.gov/pestlabl/ppls.srchreslt?CompNum=69526&ProdNum=5>, 26 pages.
Platte Chemical Co., "Product Information Bulletin: Salvo: A premium broadleaf herbicide for use in corn, small grains, grass pastures, reangeland and other crop and noncrop areas," 6 pages, 2001.
Product Bulletin for Caltex, Caltex Australia, retrieved Aug. 2, 2006. Retrieved from the Internet: <URL: http://www.caltex.com.au/products_oil_detail_print.asp?id=229>, 2 pages.
Product Information Sheet for Sylgard 309 Silicone Surfactant, Dow Corning Corporation, 4 pages, May 2004.
Propiconazole Pesticide Information Profile, Extension Toxicology Network, Oct. 1997. Retrieved from the Internet: <URL: http://pmep.cce.cornell.edu/profiles/extoxnet/metiram-propoxur/propiconazole-ext.html>, 6 pages.
PureSpray Spray Oil 10E, Delaware Department of Agriculture Pesticide Database Searches, 2 pages, retrieved Apr. 7, 2005.
Puterka, "Fungal pathogens for arthropod pest control in orchard systems: mycoinsecticidal approach for pear psylla control," *BioControl*, 44(2):183-209, 1999.
Quantification of Phosphorus in Water Based Green Pigments, 1 page, 2009.
Quicksheet for SALVO Herbicide, UAP Canada, 4 pages, 2006.
Rieke, "Thatchremoval," *California Turfgrass Culture*, 21(3):19-20, 1971.
Ross et al., "The Effect of the Plant Growth Regulator Primo on Winter Hardiness Levels," Prairie Turfgrass Research Centre, retrieved on Aug. 25, 2011. Retrieved from the Internet: <URL: http://www.oldscollege.ca/ptrc/2004_ar/Primohardiness02-05.htm>, 4 pages.
Samoucha et al., "Synergism in fungicide mixtures against Pseudoperonospora cubensis," *Phytoparasitica*, 16(4):337-342, 1988.
Schott et al., "Effects of adjuvants on herbicidal action. III. Effects of petroleum and rapeseed oils on diclofop-methyl action on ryegrass," *Agronomie*, 11(1):27-34, 1991.
Scotts Canada Home: Killex Concentrate, retreived Aug. 2, 2006. Retrieved from the Internet: <URL: http://scottscanada.calindex.cfmleventlProductGuide.product/ documentld/30B255B82B>, 2 pages.
Shaposhnikov et al., "Carboxy-substituted phthalocyanine metal complexes," *Russian journal of general chemistry*, 75(9): 1480-1488, 2005.
Shearman et al., "Colorant effects on dormant buffalograss turf performance," *HortTechnology*, 15(2), 244-246, 2005.
Short and Castner, "Turfgrass Insects Sheet 1," University of Florida, Nov. 1992, reviewed Jun. 2005. Retrieved from the Internet: <URL: http://edis.ifas.ufl.edu/in025>, 2 pages.
Short and Castner, "Turfgrass Insects Sheet 2," University of Florida, Nov. 1992, reviewed May 2003. Retrieved from the Internet: <URL: http://edis.ifas.ufl.edu/in026>, 2 pages.

(56) References Cited

OTHER PUBLICATIONS

Smitley and Davis, "Black Cutworms," Michigan State University Turfgrass Science, archived on Feb. 12, 2010. Retrieved from the Internet: <URL: http://www.turf.msu.edu/black-cutworms>, 2 pages.
Specimen Label for AGRI-DEX, Helena Chemical Company, 2 pages, 2005.
Specimen Label for Banner MAXX, Syngenta Crop Protection, Inc., 31 pages, May 2004.
Specimen Label for BLENDEX VHC, Helena Chemical Company, 2 pages, May 2006.
Specimen Label for Chipco Signature, Bayer CropScience Pty Ltd, 2 pages, May 2004.
Specimen Label for Civitas, Petro-Canada Lubricants, Inc., 9 pages, May 2004.
Specimen Label for Cleary 3336 Plus, Cleary Chemical Corporation, 4 pages, May 2004.
Specimen Label for Fore 80WP Rainshield, Dow AgroSciences, 7 pages. Revised Jan. 8, 2007.
Specimen Label for Grass Greenzit: Permanent Green Pigment for Grass, 2 pages, 1998.
Specimen Label for Harmonizer, Petro-Canada Lubricants, Inc., 1 page, May 2004.
Specimen Label for Killex, Scotts, Canada Ltd., 6 pages, Jul. 23, 2001.
Specimen Label for Peptoil, Drexel Chemical Company, 2 pages, May 2004.
Specimen Label for Regreen, Precision Laboratories, Inc. 2 pages, Dec. 10, 2007.
Specimen Label for Rovral Green GT, Bayer CropScienc Inc., 2 pages, Mar. 19, 2009.
Specimen Label for Sil-Fact, Drexel Chemical Company, 1 page, May 2004.
Specimen Label for Sil-MES 100, Drexel Chemical Company, 1 pages, May 2004.
Specimen Label for Surf-Ac 820, Drexel Chemical Company, 1 page, May 2004.
Specimen Label for Trimec Classic, PBI/Gordon Corporation, 2 pages, 1973.
Specimen Label for Trimec Southern, PBt/Gordon Corporation, 2 pages, 1987.
Technical Data Sheet for Lambent MFF 159-100, Lambent Technologies Corp., 1 page, May 2004.
Technical Data Sheet for Lambent MFF-199 SW, Lambent Technologies Corp., 1 page, May 2004.
Technical Data Sheet for Silsurf A008-UP, Siltech Corporation, 1 page, May 2004.
Technical Information for Lutensol AT types, BASF SE, 10pages, May 2004.
Technical Sheet for Green Lawnger, Becker Underwood, Inc. 1 page, Nov. 2010.
Trathnigg et al., "Molecular characterization of ethoxylates by complementary chromatographic techniques. Evaluation of efficiency and reliability," *Tenside Surf. Det.*, 40(3), 148-154, 2003.
Tu et al., "Weed control methods handbook: tools and techniques for use in natural areas," *The Nature Conservancy*, Wildland Invasive Species Team, version Apr. 2001, 219 pages.
Turfgrass Pest Control, West Virginia University, retrieved on Aug. 22, 2011. Retreived from the Internet: <URL: http://www.wvu.edu/about.exten/infores/pubs/pest/pcerti19.pdf>, 12 pages.

University of Arkansas, "Turf Tip—MSMA, Fungicide synergism, Buffalograss, Pythium." Retrieved from the Internet: <URL: http://turf.uark.edu/turfhelp/archives/030509.html> Mar. 5, 2009, 3 pages.
Unruh and Brecke, "Plant Growth Retardants for Fine Turf and Roadsides/Utilities," University of Florida, Apr 1999, reviewed Sep. 2006, retrieved on Aug. 24, 2011. Retrieved from the Internet: <URL: http://edis.ifas.ufl.edu/pdffiles/WG/WG06400.pdf>, 5 pages.
Vallad and Goodman et al., "Systemic Acquired Resistance and Induced Systemic Resistance in Conventional Agriculture," *Crop Science*, 44(6):1920-1934, 2004.
Van Dam and Kurtz, "A Turfgrass Colorant Study," California Turfgrass Culture, 21(3):17-19, Summer 1971.
van Haeringen et al., "The Development of Solid Spectral Filters for the Regulation of Plant Growth," *Photochemistry and Photobiology*, 67(4):407-413, Apr. 1998.
VanBibber, "Putting the Numbers to PGRs," Grounds Maintenance, 2008. Retrieved from the Internet: <URL: http://grounds-mag.com/chemicals/ grounds_maintenance_putting_numbers_pgrs/>, 6 pages.
Vann et al., "Rhizoctonia Large Patch Disease of Zoysiagrass and Bermudagrass," University of Arkansas Division of Agriculture, <https://www.uaex.edu/publications/PDF/FSA-7527.pdt Mar. 1, 2007, 2 pages.
Vincelli, "Chemical Control of Turfgrass Diseases 2011," University of Kentucky College of Agriculture, <URL: http://pest.ca.uky.edu/PSEP/Manuals/ppal.pdf>, 24 pages.
Vol'pin et al., "Redox and fungicidal properties of phthalocyanine metal complexes as related to active oxygen," *Journal of Inorganic Biochemistry*, 81(4): 285-292, 2000.
Walsh et al., "Biology and management of dollar spot (*Sclerotinia homoeocarpa*); an important disease of turfgrass," *HortScience.*, 34(1): 13-21, 1999.
Wicks, "Control of grapevine powdery mildew with mineral oil: an assessment of oil concentration and spray volume," *Australian Journal of Grape and Wine Research*, 5: 61-65, 1999.
Wikipedia, "2,4-Dichlorophenoxyacetic acid," retrieved on Aug. 29, 2006. Retrieved from the Internet: <URL: http://en.wikipedia.orglwikii2%2C4-D>, 3 pages.
Womack et al., "A vegetable oil-based invert emulsion for mycoherbicide delivery," *Biological Control*, 6(1), 23-28, 1996.
Yang et al., "Infection of leafy spurge by Alternaria alternata and A. angustiovoidea in the absence of dew," *Phytopathology*, 83(9): 953-958, 1993.
Youngner et al., "Colorants for Dormant Bermuda and Other Subtropical Grasses," Southern California Turfgrass Culture, 8(1):7-8, 1958.
Youngner, "Gibberellic acid on Zoysia grasses," Southern Calif. Turfgrass Cult 8: 5-6, 1958.
Youngner, "Kikuyugrass, Pennisetum Clandestinum, and Its Control," Southern California Turfgrass Culture, 8(1):1-4, Jan. 1958.
International Search Report for PCT/CA2012/050376 mailed Aug. 28, 2012, 11 pages.
International Preliminary Report on Patentability for PCT/CA2012/050376 issued Dec. 4, 2013, 7 pages.
U.S. Appl. No. 14/376,006, filed Jul. 31, 2014, Liu et al.
U.S. Appl. No. 14/405,644, filed Dec. 4, 2014, Fefer et al.

\* cited by examiner

PARAFFINIC OIL-IN-WATER EMULSIONS FOR CONTROLLING INFECTION OF CROP PLANTS BY FUNGAL PATHOGENS

CROSS REFERENCE TO RELATED APPLICATIONS

This application claims the benefit of U.S. Provisional Application No. 61/493,118, filed Jun. 3, 2011, and U.S. Provisional Application No. 61/496,500, filed Jun. 13, 2011, each of which is incorporated by reference in its entirety.

TECHNICAL FIELD

This disclosure features combinations that include a paraffinic oil. The combinations can further include (but are not limited to) one or more of the following: one or more emulsifiers, one or more pigments, one or more silicone surfactants, one or more anti-settling agents, one or more conventional chemical fungicides (e.g., a DMI or a QoI), and water. In some implementations, the combinations can be in the form of a single composition (e.g., which is contained within a storage pack or a vessel (e.g., a tank) suitable for applying the composition to a plant, e.g., crop plant). Typically, the composition is applied to a plant after dilution with water. In other implementations, the combinations can include two or more separately contained (e.g., packaged) compositions, each containing one or more of the above-mentioned components. Said compositions can be combined and applied to a plant typically after dilution with water; or each composition can be applied separately to the same plant either simultaneously or sequentially, and typically after dilution with water. This disclosure also features methods of using the combinations for controlling infection of a crop plant by a fungal pathogen as well as methods of formulating combinations that include both oil and water as oil-in-water (O/W) emulsions.

BACKGROUND

Rusts are plant diseases caused by fungal pathogens of the order Pucciniales. Rusts can affect a variety of plants, including monocotyledons and dicotyledons, as well as various plant organs, including leaves, stems, fruits and seeds. Rust is typically observed as colored powdery pustules composed off tiny spores that form on the lower plant organ surfaces. Common rust-causing fungal species include *Gymnosporangium juniperi-virginianae* (Cedar-apple rust) which attacks apple and pear and hawthorn; *Cronartium ribicola* (White pine blister rust); which attacks white pines and currants; *Hemileia vastatrix* (Coffee rust) which attacks coffee plant; *Puccinia graminis* (wheat stem rust) which attacks Kentucky bluegrass, barley, and wheat; *Puccinia coronata* (Crown Rust of Oats and Ryegrass) which attacks oats; *Phakopsora meibomiae* and *P. pachyrhizi* (soybean rust) which attacks soybean and various legumes; *Uromyces phaseoli* (Bean rust) which attacks bean; *Puccinia hemerocallidis* (Daylily rust) which attacks Daylily; *Puccinia persistens* subsp. *triticina* causes (wheat rust in grains, also known as 'brown or red rust'); *P. sriiformis* (yellow or stripe rust); *Uromyces appendeculatus* which attacks bean.

Wheat stem rust is caused by the fungus *Puccinia graminis* and is a significant disease affecting cereal crops, particularly wheat (*Triticum* spp.) An epidemic of stem rust on wheat caused by race Ug99 is currently spreading across Africa, the Middle East, and Asia, and threatening large numbers of people who are dependent on wheat for sustenance. The rust fungus attacks the parts of the plant which are above ground. Spores that land on green wheat plants form a pustule that invades the outer layers of the stalk. Where infection has occurred on the stem or leaf, elliptical blisters or pustules called uredia develop. Infected plants produce fewer tillers and set fewer seed.

Soybean rust is a disease that primarily affects soybeans and other legumes. It is caused by two species of fungi, *Phakopsora pachyrhizi* and *Phakopsora meibomiae*. Soybean rust has been reported in Asia, Australia, Africa, South America and North America. Soybean rust is spread by wind-borne spores, which are released in cycles of seven days to two weeks. Yield losses can be severe with this disease and losses of 10-80% have been reported.

Multi-pronged approaches are desirable to address the spread of fungal infection. A variety of preventative methods may be employed. For example, rust diseases are correlated to relatively high moisture. Accordingly, avoidance of overhead watering at night, using drip irrigation, reducing crop density, and the use of fans to circulate air flow may serve to lower the relative moisture and decrease the severity of rust infection.

Other strategies may include reducing the area of the plant that the pathogen destroys, or slowing down the spread of the fungus. Fungus-resistant plants may be used to interrupt the disease cycle because many rusts are host-specific. This approach has proven very successful in the past for control of wheat stem rust; however, Ug99 is currently virulent against most wheat varieties. Currently, there are no commercial soybean varieties with resistance to soybean rust. Accordingly, soybean rust is managed with fungicides.

In large agricultural operations, conventional synthetic fungicides can be used to control fungal pathogens. De-methylation inhibitors (DMI) such tebuconazole (Folicur™, Bayer) and propioconazole (Tilt™) may be effective for the control of wheat stem rust, while tetraconazole (Domark™, Valent) be effective for the control of soybean rust. Quinone Outside Inhibitors (QoI), such as pyraclostrobin (Headline™, BASF), may be effective for the control of soybean rust, while azoxystrobin (Quadris™) may be effective for the control of wheat stem rust.

Conventional fungicides are generally applied by air to the foliage as contact between the pathogen with the fungicide is required for efficacy. This process can be expensive and fungicide application is often reserved for seasons when foliar diseases are severe. Second, conventional fungicides typically target specific sites of important pathogen proteins. Accordingly, strains may develop resistance to the fungicide after repeat applications. Third, the efficacy of conventional chemical fungicides is not always satisfactory for some of the diseases, such as *Fusarium* Head Blight (Scab). Finally, conventional fungicides are generally not acceptable for use in organic farming.

As an alternative approach to conventional chemical fungicides, oil-in-water emulsions comprising paraffinic oils (paraffinic oil-in-water emulsions) and paraffinic spray oils have been used in turfgrass management practices for controlling turfgrass pests (see, for example, Canadian Patent Application 2,472,806 and Canadian Patent Application 2,507,482). In addition, oil-in-water formulations comprising paraffinic oils and a pigment for controlling turfgrass pests have been reported (see, for example, WO 2009/155693). For example, Petro-Canada produces CIVITAS™, is a paraffinic oil-in-water emulsion that functions as a broad spectrum fungicide and insecticide for use on golf course turf and landscape ornamentals, used for example to control powdery mildew, adelgids and webworms on landscape ornamentals (US EPA REG. NO. 69526-13). Product labeling indicates that CIVITAS™ may be applied as part of an alternating spray program or in tank mixes with other turf and ornamental protection products; and that CIVITAS™ may be used as a preventative treatment with curative properties for the control of many important diseases on turf, including fairways and roughs.

SUMMARY

This disclosure features combinations that include a paraffinic oil. The combinations can further include (but are not limited to) one or more of the following: one or more emulsifiers, one or more pigments, one or more silicone surfactants, one or more anti-settling agents, one or more conventional chemical fungicides (e.g., a DMI or a QoI), and water. In some implementations, the combinations can be in the form of a single composition (e.g., which is contained within a storage pack or a vessel (e.g., a tank) suitable for applying the composition to a plant, e.g., crop plant). Typically, the composition is applied to a plant after dilution with water. In other implementations, the combinations can include two or more separately contained (e.g., packaged) compositions, each containing one or more of the above-mentioned components. Said compositions can be combined and applied to a plant typically after dilution with water; or each composition can be applied separately to the same plant either simultaneously or sequentially, and typically after dilution with water. This disclosure also features methods of using the combinations for controlling infection of a crop plant by a fungal pathogen as well as methods of formulating combinations that include both oil and water as oil-in-water (O/W) emulsions.

It has been found that the combinations described herein (e.g., combinations that include one or more conventional chemical fungicides, such as a DeMethylation Inhibitor (DMI) or a Quinone outside Inhibitor (QoI) fungicide, and the components present in CIVITAS™/CIVITAS HARMONIZER™) are surprisingly effective in controlling fungal diseases, including, e.g., wheat stem rust, soybean rust, leaf rust, stripe rust, *fusarium* head blight, spot blotch, and *Septoria* complex in vascular crop plants. In some implementations, the combined effect of two (or more) components of the combination (e.g., the paraffinic oil and one or more conventional chemical fungicides, such as a DeMethylation Inhibitor (DMI) or a Quinone outside Inhibitor (QoI) fungicide and/or the pigment) on controlling fungal disease is greater than the expected sum of each component's individual effect on controlling a fungal disease (e.g., wheat stem rust, soybean rust, leaf rust, stripe rust, *fusarium* head blight, spot blotch, and *Septoria* complex in vascular crop plants). In certain implementations, the combined effect of the two (or more) components present in the combinations described herein is a synergistic effect. The Examples illustrate that combined use of paraffinic oil with a pigment, a DMI fungicide, and or a QoI fungicide provides an unexpected synergistic response in the control of wheat stem rust, soybean rust, leaf rust, *fusarium* head blight, and spot blotch, in crop plants. In certain implementations, the dosage of such conventional chemical fungicides can be reduced significantly, such as to 50% the recommended label rates, as well provide significant reduction in the dosage of the combinations described herein.

In one aspect, combinations (e.g., fungicidal compositions) are featured that include various combinations of a paraffinic oil-in-water emulsion with a pigment and/or a conventional chemical fungicide, such as a DMI or a QoI, for controlling infection of a crop plant (e.g., vascular crop) plant by a fungal pathogen. In some implementations, two (or more) components of the combination (e.g., the paraffinic oil and one or more conventional chemical fungicides, such as a DeMethylation Inhibitor (DMI) or a Quinone outside Inhibitor (QoI) fungicide and/or the pigment) are present in amounts in which the combined effect of two (or more) components is greater than the expected sum of each component's individual effect on controlling a fungal disease (e.g., wheat stem rust, soybean rust, leaf rust, stripe rust, *fusarium* head blight, spot blotch, and *Septoria* complex in vascular crop plants). In certain implementations, the paraffinic oil and conventional chemical fungicide are present in amounts that are synergistically effective when applied to a plant for controlling a fungal pathogen of the plant.

In another aspect, uses are provided for combinations (e.g., fungicidal compositions) that include a paraffinic oil-in-water emulsion in controlling infection of a vascular plant by a fungal pathogen. The paraffinic oil-in-water emulsion includes paraffinic oil and an emulsifier and can further include any one or more of the components listed above.

The plant can be a crop plant.

The plant may be monocotyledonous. The monocotyledonous plant may be of the order Poaceae. The plant may be of the genus *Triticum, Secale, Hordeum, Oryza, Zea*, or *Elymus*. The fungal pathogen may be of the order Pucciniales. The fungal pathogen may be of the genus *Puccinia*. The fungal pathogen may be of the species *Puccinia graminis, Puccinia triticina*, or *Puccinia sriiformis*. The fungal pathogen can also be *Bipolaris sorokiniana* or *Fusarium graminearum.*

The plant can be dicotyledonous. The plant can be of the order Fabaceae. The plant can be of the species *Glycine max*. The fungal pathogen can be of the genus *Phakopsora*. The fungal pathogen can be *Phakopsora pachyrhizi* and *Phakopsora meibomiae*. The plant can be of the genus *Gossypium*. The fungal pathogen can be *Phakopsora gossypii.*

The paraffinic oil can include a paraffin having a number of carbon atoms of from 12 to 50. The paraffin can have a number of carbon atoms of from about 16 to 35. The paraffin can have an average number of carbon atoms of 23.

The paraffinic oil may have a paraffin content of at least 80%. The paraffinic oil may have a paraffin content of at least 90%. The paraffinic oil may have a paraffin content of at least 99%.

The paraffinic oil can be used in a range from 13 to 3200 oz/acre (i.e. 0.3 to 75 oz/1000 square feet). The paraffinic oil can be used in a range from 40 to about 640 oz/acre. The oil-in-water emulsion can be used in a range from 2 to 50 gallons per acre for foliar application. The oil-in-water emulsion can be used in a range from 200 to 400 gallons per acre for soil drench application or water-in application with irrigation.

The combinations (e.g., fungicidal compositions) can further include a demethylation inhibitor (DMI). The DMI may be tetraconazole, tebuconazole, propioconazole, azaconazole, bitertanol, bromuconazole, cyproconazole, difenoconazole, diniconazole, epoxiconazole, etaconazole, fenbuconazole, fluquinconazole, flusilazole, flutriafol, hexaconazole, imibenconazole, ipconazole, metconazole, myclobutanil, penconazole, prothioconazole, simeconazole, triadimefon, triadimenol, triticonazole, imazalil, oxpoconazole, pefurazoate, prochloraz, triflumizole, fenarimol, nuarimol, triforine, or pyrifenox. The DMI can be tebuconazole, and may be used in a range from about 0.02 to about 0.5 lb. ai./acre. The DMI may be propioconazole, and can be used in a range from about 0.01 to about 0.6 lb. ai./acre. The DMI can be tetraconazole, and may be used in a range from 0.015 to 0.15 lb. ai./acre. The DMI can be prothioconazole, and may be used in a range from 0.02 to 0.4 lb. ai./acre.

The combinations (e.g., fungicidal compositions) can further include a Quinone outside Inhibitor (QoI). The QoI may be azoxystrobin, enestrobin, picoxystrobin, pyraclostrobin, trifloxystrobin, dimoxystrobin, metominostrobin, orysastrobin, famoxadonem, fluoxastrobin, fenamidone, or pyribencarb. The QoI can be azoxystrobin, and may be used in a range from 0.01 to 0.50 lb. ai./acre. The QoI can be pyraclostrobin, and may be used in a range from 0.02 to 0.40 lb. ai./acre.

The combinations (e.g., fungicidal compositions) can further include an emulsifier (e.g., a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof).

The combinations (e.g., fungicidal compositions) can further include a pigment (e.g., a polychlorinated (Cu II) phthalocyanine).

The combinations (e.g., fungicidal compositions) can further include a silicone surfactant.

The combinations (e.g., fungicidal compositions) can further include a pigment and a silicone surfactant.

The combinations (e.g., fungicidal compositions) can further include a pigment, a silicone surfactant, and an emulsifier.

In certain implementations, the combinations (e.g., fungicidal compositions) can further include an emulsifier and a combination of a pigment and a silicone surfactant, and the combined effect of the emulsifier, the paraffinic oil, the pigment and the silicone surfactant is greater than the expected sum of each component's individual effect on controlling infection by the fungal pathogen (e.g., the aforementioned components can be present in amounts that, when applied to the plant, are synergistically effective at controlling infection by the fungal pathogen). The pigment can be a polychlorinated (Cu II) phthalocyanine. The pigment can be dispersed in water. The emulsifier can include a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. The pigment can be be dispersed in oil, and the emulsifier may include a natural or synthetic alcohol ethoxylate, a polymeric surfactant, a sorbitan fatty acid ester, or a combination thereof, and the combination may further comprises a polyethylene glycol according to formula IV:

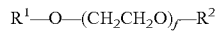

wherein R1=H or CH2=CH—CH2 or COCH3; R2=H or CH2=CH—CH2 or COCH3; and f≥1.

The ratio of the paraffinic oil-in-water emulsion to the combination of the pigment and the silicone surfactant can be from 32:1 to 4:1.

The ratio of the paraffinic oil to the pigment can be from about 5:1 to 100:1, such as 30:1).

The weight ratio of the paraffinic oil to the emulsifier can be from 10:1 to 100:1.

The weight ratio of the pigment to the silicone surfactant can be from 2:1 to 50:1.

The weight ratio of the paraffinic oil to the conventional chemical fungicide can be from 2:1 to 10,000:1

The fungicidal composition can be applied to the root tissue of the plant. The application to the root tissue can be by soil drench.

The compositions further include one or more anti-settling agents.

This disclosure also features combinations that include a paraffinic oil and a QoI fungicide. The combinations can further include (but are not limited to) one or more of the following: one or more emulsifiers, one or more pigments, one or more silicone surfactants, one or more anti-settling agents, and water.

Definitions

As used herein, the term "oil-in-water emulsion" refers to a mixture in which one of the paraffinic oil and water (e.g., the paraffinic oil) is dispersed as droplets in the other (e.g., the water). In some implementations, an oil-in-water emulsion is prepared by a process that includes combining the paraffinic oil, water, and any other components and the paraffinic oil and applying shear until the emulsion is obtained (typically a white milky color is indicative of the formation of an emulsion in the absence of any pigment; a green color is observed in the presence of a pigment). In other implementations, an oil-in-water emulsion is prepared by a process that includes combining the paraffinic oil, water, and any other components in the mixing tank and sprayed through the nozzle of a spray gun.

As used herein, the term "control a fungal pathogen of a plant" or "control a disease caused by a fungal pathogen" (and the like) means to diminish, ameliorate, or stabilize the disease and/or any other existing unwanted condition or side effect that is caused by the association of a fungal pathogen with the plant.

As used herein, the term "crop plant" refers to a non-woody plant, which is grown, tended to, and harvested in a cycle of one year or less as source of foodstuffs and/or energy. Examples of crop plants include, without limitation, sugar cane, wheat, rice, corn (maize), potatoes, sugar beets, barley, sweet potatoes, cassava, soybeans, tomatoes, legumes (beans and peas).

In certain implementations, the combinations, e.g., fungicidal compositions, exhibit a synergistic response, for example in controlling a fungal pathogen in a crop plant. In certain implementations, the combinations, e.g., fungicidal compositions may be synergistic fungicidal compositions for treating a fungal pathogen in crop plants. In selected implementations, the fungicidal compositions may exhibit a synergistic response, for example in controlling stem rusts in crop plants. As for example is suggested by Burpee and Latin (Plant Disease Vol. 92 No. 4, April 2008, 601-606), the term "synergy", "synergistic", or the like, may refer to the interaction of two or more agents so that their combined effect is greater than the sum of their individual effects, this may include, in the context of the invention, the action of two or more fungicidal agents in which the total response of a fungus to the fungicidal agent combination is greater than the sum of the individual components. Applying the approach to identifying synergy a set out in S. R. Colby, "Calculating synergistic and antagonistic responses of herbicide combinations", Weeds 15, 20-22 (1967), expected efficacy, E, may be expressed as: E=X+Y(100-X)/100, where X is the efficacy, expressed in % of the untreated control, of a first composition, and Y is the efficacy, expressed in % of the untreated control, of the second composition.

The details of one or more implementations of the combinations and methods described herein are set forth in the accompanying description below. Other features and advan-

DETAILED DESCRIPTION

Figure 1:
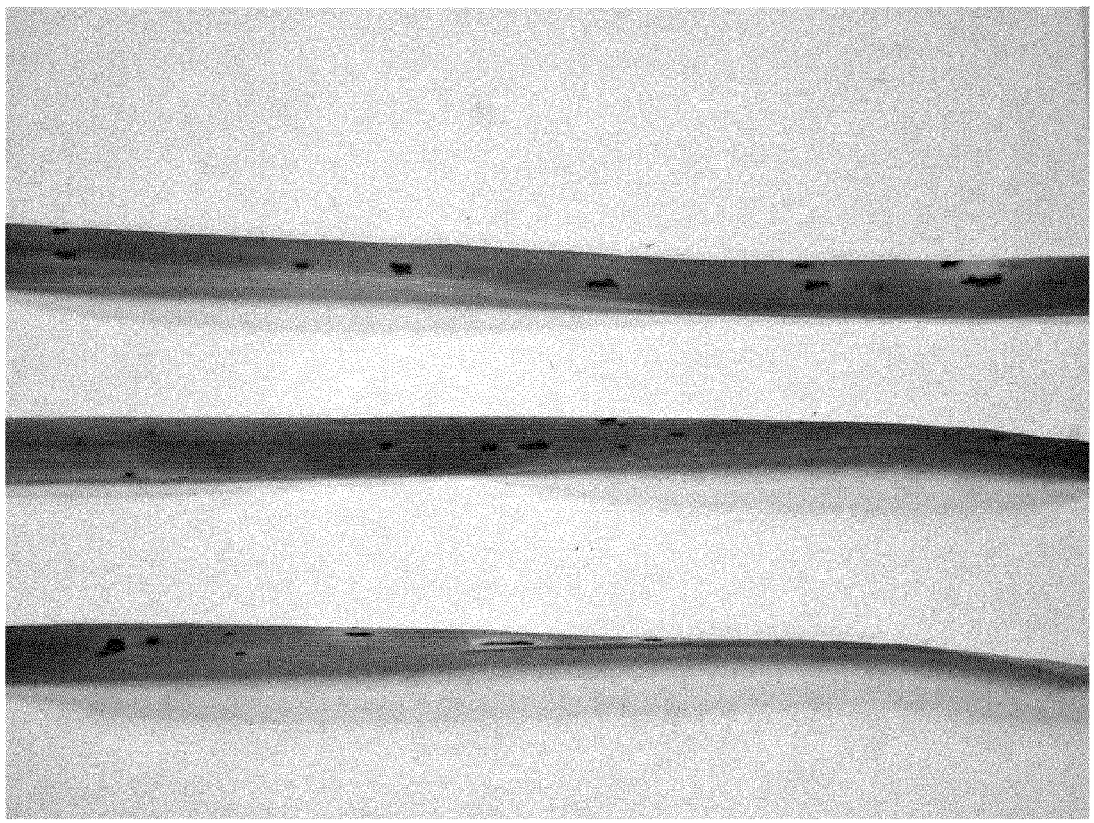
FIG. 1 is an image of a leaf blade of a wheat plant displaying splotch blot disease after inoculation with *Bipolaris sorokiniana* without prior treatment with a fungicidal composition.

This disclosure features combinations that include a paraffinic oil. The combinations can further include (but are not limited to) one or more of the following: one or more emulsifiers, one or more pigments, one or more silicone surfactants, one or more anti-settling agents, one or more conventional chemical fungicides (e.g., a DMI or a QoI), and water. In some implementations, the combinations can be in the form of a single composition (e.g., which is contained within a storage pack or a vessel (e.g., a tank) suitable for applying the composition to a plant, e.g., crop plant). Typically, the composition is applied to a plant after dilution with water. In other implementations, the combinations can include two or more separately contained (e.g., packaged) compositions, each containing one or more of the above-mentioned components. Said compositions can be combined and applied to a plant typically after dilution with water; or each composition can be applied separately to the same plant either simultaneously or sequentially, and typically after dilution with water. This disclosure also features methods of using the combinations for controlling infection of a vascular crop plant by a fungal pathogen as well as methods of formulating combinations that include both oil and water as oil-in-water (O/W) emulsions.

I. Components

[A] Conventional Chemical Fungicides

The combinations include isomers such as geometrical isomers, optical isomers based on asymmetric carbon, stereoisomers and tautomers of the compounds described herein and are not limited by the description of the compounds for the sake of convenience.

[1]

In some implementations, the conventional fungicide is a DMI fungicide.

In certain implementations, the DMI fungicide is at least one fungicide selected from the group consisting of tetraconazole, tebuconazole, propioconazole, azaconazole, bitertanol, bromuconazole, cyproconazole, difenoconazole, diniconazole, epoxiconazole, etaconazole, fenbuconazole, fluquinconazole, flusilazole, flutriafol, hexaconazole, imibenconazole, ipconazole, metconazole, myclobutanil, penconazole, prothioconazole, simeconazole, triadimefon, triadimenol, triticonazole, imazalil, oxpoconazole, pefurazoate, prochloraz, triflumizole, fenarimol, nuarimol, triforine, and pyrifenox.

In certain implementations, the DMI fungicide is at least one fungicide selected from the group consisting of tetraconazole, tebuconazole, and propioconazole. Tetraconazole can be obtained commercially, for example, as a product identified as Domark™ (available from Valent). Tebuconazole can be obtained commercially, for example, as a product identified as Folicur™ (available from Bayer Crop Science). Propioconazole can be obtained commercially, for example, in the product identified as Quilt™ (available from Syngenta).

In other implementations, the DMI fungicides described herein can be synthesized using conventional techniques known in the art of synthetic organic chemistry.

[2]

In some implementations, the conventional fungicide is a QoI fungicide.

In certain implementations, the QoI fungicide is at least one fungicide selected from the group consisting of pyraclostrobin, azoxystrobin, fluoxastrobin, trifloxystrobin, coumoxystrobin, dimoxystrobin, enoxastrobin, famoxadone, fenamidone, fenaminostrobin, flufenoxystrobin, kresoximmethyl, metominostrobin, orysastrobin, pyraoxystrobin picoxystrobin, pyrametastrobin, pyribencarb, and triclopyricarb.

In certain implementations, the QoI fungicide is at least one fungicide selected from the group consisting of pyraclostrobin, azoxystrobin, fluoxastrobin, and trifloxystrobin.

In certain implementations, the QoI fungicide is at least one fungicide selected from the group consisting of pyraclostrobin and azoxystrobin.

In certain implementations, the QoI fungicide is methyl (2E)-2-{2-[(3-butyl-4-methyl-2-oxo-2H-chromen-7-yl)oxymethyl]phenyl}-3-methoxyacrylate (coumoxystrobin): CAS No. 850881-70-8.

In certain implementations, the QoI fungicide is (E)-2-(methoxyimino)-N-methyl-2-[α-(2,5-xylyloxy)-o-tolyl]acetamide (dimoxystrobin): CAS No. 149961-52-4.

In certain implementations, the QoI fungicide is enoxastrobin. In alternative implementations, the QoI fungicide may be, for example, (RS)-3-anilino-5-methyl-5-(4-phenoxyphenyl)-1,3-oxazolidine-2,4-dione (famoxadone): CAS No. 131807-57-3.

In certain implementations, the QoI fungicide is (S)-1-anilino-4-methyl-2-methylthio-4-phenylimidazolin-5-one (fenamidone): CAS No. 161326-34-7.

In certain implementations, the QoI fungicide is fenaminostrobin.

In certain implementations, the QoI fungicide is flufenoxystrobin.

In certain implementations, the QoI fungicide is methyl (E)-methoxyimino[α-(o-tolyloxy)-o-tolyl]acetate (kresoxim-methyl): CAS No. 143390-89-0.

In certain implementations, the QoI fungicide is (E)-2-(methoxyimino)-N-methyl-2-(2-phenoxyphenyl)acetamide (metominostrobin): CAS No. 133408-50-1.

In certain implementations, the QoI fungicide may be, for example, (2E)-2-(methoxyimino)-2-{2-[ (3E,5E,6E)-5-(methoxyimino)-4,6-dimethyl-2,8-dioxa-3,7-diazanona-3,6-dien-1-yl]phenyl}-N-methylacetamide (orysastrobin): CAS No. 248593-16-0.

In certain implementations, the QoI fungicide is methyl (2E)-2-(2-{[3-(4-chlorophenyl)-1-methylpyrazol-5-yl]oxymethyl}phenyl)-3-methoxyacrylate (pyraoxystrobin): CAS No. 862588-11-2.

In certain implementations, the QoI fungicide is methyl (2E)-3-methoxy-2-{2-[6-(trifluoromethyl)-2-pyridyloxymethyl]phenyl}acrylate (picoxystrobin): CAS No. 117428-22-5.

In certain implementations, the QoI fungicide is pyrametastrobin.

In certain implementations, the QoI fungicide is methyl {2-chloro-5-[(1E)-1-(6-methyl-2-pyridylmethoxyimino)ethyl]benzyl}carbamate (pyribencarb): CAS No. 799247-52-2.

In certain implementations, the QoI fungicide is triclopyricarb.

In certain implementations, the QoI fungicide is carbamic acid, [2-[[[1-(4-chlorophenyl)-1H-pyrazol-3-yl]oxy]methyl]-phenyl]methoxy-, methyl ester (pyraclostrobin). Pyraclostrobin may be commercially available, for example, as a product identified as Insignia™ (available from BASF Corporation, 26 Davis Drive, Research Triangle Park, N.C. 27709).

In certain implementations, the QoI fungicide is methyl (E)-2-{2-[6-(2-cyano-phenoxy)pyrimidin-4-yloxy]phenyl}-3-methoxy-acrylate (azoxystrobin). Azoxystrobin may be commercially available, for example, as a product identified as Heritage™ (available from Syngenta Crop Protection, Inc., Greensboro, N.C. 27409).

In certain implementations, the QoI fungicide is [(1E)-[2-[[6-(2-chlorophenoxy)-5-fluoro-4-pyrimidinyl]oxy]phenyl]5,6-dihydro-1,4,2-dioxazin-3-yl]methanone-O-methyloxime] (fluoxastrobin). Fluoxastrobin may be commercially available, for example, as a product identified as Disarm™ (available from Arysta LifeScience North America, LLC, 15401 Weston Parkway, Suite 150, Cary, N.C. 27513).

In certain implementations, the QoI fungicide is benzeneacetic acid, (E,E)-alpha-(methoxyimino)-2((((1-(3-trifluoromethyl)phenyl]ethylidene)-amino)oxy)methyl)-, methyl ester (trifloxystrobin). Trifloxystrobin may be commercially available, for example, as a product identified as Compass™ (available from Bayer Environmental Science, 2T. W. Alexander Drive, Research Triangle Park, N.C. 27709).

In other implementations, the QoI fungicides described herein can be synthesized using conventional techniques known in the art of synthetic organic chemistry.

[B] Paraffinic Oil

The paraffinic oil confers properties (e.g., fungicidal properties) that are useful for promoting the health of a plant (e.g., crop plant). While not wishing to be bound by theory, it is believed that the paraffinic oil is able to provoke an induced systemic resistance (ISR) response, a systemic acquired resistance (SAR), or other defense response in a plant.

[1]

In some implementations, the paraffinic oil includes an oil enriched in paraffin.

In certain implementations, the paraffinic oil includes a paraffin having from 12 carbon atoms to 50 carbon atoms (e.g., 12 carbon atoms to 40 carbon atoms, 16 carbon atoms to 35 carbon atoms, 12 carbon atoms to 21 carbon atoms; e.g., 16 carbon atoms to 35 carbon atoms).

In certain implementations, the paraffinic oil includes a paraffin having an average number of carbon atoms that is less than or equal to about 20 (e.g., 16).

In certain implementations, the paraffinic oil includes a paraffin having an average number of carbon atoms of from 16 to 30 e.g., 23 or 27).

In certain implementations, the paraffinic oil includes a paraffin having from 16 carbon atoms to 35 carbon atoms and an average number of carbon atoms of 23.

In certain implementations, the paraffin is an isoparaffin (e.g., a synthetic isoparaffin manufactured from two-stage Severe Hydrocracking/Hydroisomerization process).

In some implementations, a paraffin is present in the paraffinic oil in an amount, that is at least 80% (e.g., at least 90%, at least 99%).

[2]

In some implementations, the paraffinic oil has been refined to remove compounds that are associated with plant injury, for example, aromatic compounds or compounds containing sulfur, nitrogen, or oxygen. In certain implementations, the paraffinic oil includes relatively low levels of aromatic compounds and/or compounds containing sulfur, nitrogen, or oxygen, e.g., less than 10 weight percent (less than 5 weight percent, less than 2 weight percent, less than 0.5 weight percent) of aromatic compounds and/or compounds containing sulfur, nitrogen, or oxygen.

[3]

Non-limiting examples of suitable paraffinic oils include, HT60, HT100, High Flash Jet, LSRD, and N65DW (available from Petro-Canada, Calgary, AB, Canada).

[C] Emulsifier

In some implementations, the combinations include both paraffinic oil, emulsifier, and water. It can be advantageous to store and/or apply such combinations as oil-in-water (O/W) emulsions.

Emulsions tend to be thermodynamically unstable due to excess free energy associated with the surface of the dispersed droplets such that the particles tend to flocculate (clumping together of dispersed droplets or particles) and subsequently coalesce (fusing together of agglomerates into a larger drop or droplets) to decrease the surface energy. If these droplets fuse, the emulsion will "break" (i.e., the phases will separate) destroying the emulsion, which in some cases can be detrimental to the storage shelf-life of the combinations. While not wishing to be bound by theory, it is believed that the addition of one (or more) emulsifying agents or emulsifiers can prevent or slow the "breaking" of an emulsion. As the skilled artisan will appreciate, the type and concentration of a particular emulsifying agent will depend, inter alfa, on the emulsion phase components and the desired result.

[1]

In some implementations, the emulsifier is a "fast break" or "quick break" emulsifier. While not wishing to be bound by theory, it is believed that a "fast break" or "quick break" emulsifier allows the paraffinic oil to be quickly released from the O/W emulsion upon application to the turfgrass for contact, e.g., with a fungal pathogen. When a "fast break" or "quick break" emulsifier is present in a suitable amount (for example a selected proportion or ratio with respect to the paraffinic oil), the resulting "fast break" or "quick break" O/W emulsion quickly releases the oil phase upon application to the turfgrass. As such, there is less runoff of the O/W emulsion from the grass blades (as compared to more stable O/W emulsions) resulting in more oil adhering to the turfgrass for a longer period of time to more effectively contact and control, e.g., associated fungal pathogen. In certain implementations, the oil phase resides on the turfgrass for a period of not less than one hour. In certain implementations, the oil phase resides on the turfgrass for a period of from not less than 1 hour but not more than 30 days. In certain implementations, the "fast break" or "quick break" emulsion may be, for example, an emulsion having an oil phase that, after mixing with water, is reconstituted in 0.5 to 15 minutes according to the following test:
1. Fill 100 mL graduated cylinder with tap water.
2. Add 1 mL of emulsified oil.
3. Invert graduated cylinder 5 times.
4. Using a stop watch and human observation, measure how long it takes for the oil phase to reconstitute after inversion (step 3).

In some implementations, the oil phase is reconstituted in from 2 minutes to 5 minutes according to the test described above. In some instances, the "fast break" or "quick break" property of the O/W emulsion is balanced with the need to provide an O/W emulsion with a suitable shelf life under suitable storing conditions, and for a suitable timeframe.

[2]

In some implementations, the emulsifier is (or includes) one (or more of the following) a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or any combination thereof.

In certain implementations, the emulsifier is (or includes) a natural or synthetic alcohol ethoxylate, a polymeric surfactant, a sorbitan fatty acid ester, or any combination thereof.

In certain implementations, the natural or synthetic alcohol ethoxylate is a polyoxyethylene (4 to 12) lauryl ether (C12), polyoxyethylene (10) cetyl ether (C16), polyoxyethylene (10) stearyl ether (C18), polyoxyethylene (10) oleyl ether (C18 mono-unsaturated), a polyoxyethylene (2 to 11) C12-C15 alcohol, a polyoxyethylene (3 to 9) C11-C14 alcohol, a polyoxyethylene (9) C12-C14 alcohol, a polyoxyethylene (11) C16-C18 alcohol, a polyoxyethylene (20) C12-C15 alcohol, or any combination thereof. For example, the natural or synthetic alcohol ethoxylate can be a polyoxyethylene (4 to 7) lauryl ether (C12), polyoxyethylene (10) cetyl ether (C16), a polyoxyethylene (2 to 11) C12-C15 alcohol, a polyoxyethylene (3 to 9) C11-C14 alcohol, a polyoxyethylene (9) C12-C14 alcohol, or any combination thereof. As another example, the alcohol alkoxylate can be a butyl ether polyoxyethylene/polyoxypropylene block copolymer.

In certain implementations, the emulsifier is (or includes) an alkyl polysaccharide, e.g., a C8-C11 alkylpolysaccharide or any combination thereof.

In certain implementations, the emulsifier is (or includes) a glycerol oleate, e.g., a glycerol mono-, di-, tri-oleate, or any combination thereof.

In certain implementations, the emulsifier is (or includes) a polyoxyethylene-polyoxypropylene block copolymer, e.g., a polyoxyethylene-polyoxypropylene block copolymer having a molecular weight (or relative molar mass) of from 1100 to about 11400 and 10 to 80% (ethylene oxide) EO.

In certain implementations, the emulsifier is (or includes) an alkyl phenol ethoxylate, e.g., a nonyl phenol ethoxylate, a dodecyl phenol ethoxylate, or any combination thereof. For example, the nonyl phenol ethoxylate can be a polyoxyethylene (2 to 8) nonylphenol.

In certain implementations, the emulsifier is (or includes) a polymeric surfactant, e.g., a graft copolymer, a random copolymer, or any combination thereof. For example, the graft copolymer can be a polymethacrylic acid and acrylate with polyoxyethylene chains. For example, the random copolymer can be a random copolymer having ester and ether groups.

In certain implementations, the emulsifier is (or includes) a polyethylene glycol, e.g., a polyethylene glycol having a molecular weight ("MW") (or relative molar mass) of from 200 to 8000, e.g., MW 400 PEG dioleate; or MW600 PEG dioleate.

In certain implementations, the emulsifier is (or includes) a sorbitan fatty acid ester ethoxylate, e.g., polyoxyethylene (20) sorbitan tristearate, polyoxyethylene (20) sorbitan monooleate, polyoxyethylene (5) sorbitan monooleate, polyoxyethylene (20) sorbitan trioleate, or any combination thereof. For example, the sorbitan fatty acid ester can be a sorbitan tristearate, a sorbitan triolate, or any combination thereof.

In certain implementations, the emulsifier is (or includes) an alkyl phenol ethoxylate, a mixture of an ethoxylated alcohol and a glycerol oleate, or any combination thereof.

In certain implementations, the emulsifier is (or includes) a mixture of an ethoxylated alcohol and a glycerol oleate, e.g.: a C10 to C16 alcohol ethoxylate and a glycerol oleate combination; or polyoxyethylene lauryl ether, C10 to C16 alcohol ethoxylates, and glycerol oleate; or ethoxylated alcohols having primary C5-C20 carbon chains with an average of about 2 to about 7 ethoxylation groups, and a glycerol oleate; or a polyoxyethylene (11) C16-18 alcohol.

In certain implementations, the emulsifier is (or includes) a sorbitan tristearate.

Non-limiting examples of suitable emulsifiers include AL3149 (available from Uniqema), AL3313 (available from Uniqema), PC Emuls Green (available from Petro-Canada, Calgary, AB, Canada), Lutensol™ AT11 (available from BASF), SPAN65 (available from Uniqema), and S-MAZ™65 K (available from BASF).

[3]

In some implementations, the weight ratio of the paraffinic oil to the emulsifier is from 10:1 to 500:1 (e.g., from 98:2 to 99.9:0.1, from 98:2 to 99.5:0.5). By way of example, the weight ratio of the paraffinic oil to the emulsifier can be 95:5, 98:2, 98.5:1.5, 99:1, 99.5:0.5.

[D] Pigment

In some implementations, the combinations can include one (or more) pigments. The pigments can provide color to the plant being treated (e.g., turf grass) and/or in some implementations, the pigment(s) and the paraffinic oil can exhibit a greater than additive effect in promoting the health of a plant (e.g., controlling a fungal pathogen of a plant; see, for example, WO 2009/155693).

In some implementations, the pigment is a water-based pigment dispersion.

In some implementations, the pigment is an oil-based pigment dispersion.

In some implementations, the pigment is a phthalocyanine compound.

In certain implementations, the pigment is a metal-free phthalocyanine compound. In certain implementations, the pigment is a halogenated, metal-free phthalocyanine, e.g., a polychlorinated metal-free phthalocyanine.

In certain implementations, the pigment is a metal phthalocyanine compound.

In certain implementations, the pigment is a copper phthalocyanine.

In certain implementations, the copper phthalocyanine is a non-halogenated copper phthalocyanine, e.g., a nonchlorinated copper phthalocyanine. As an example, the pigment can be Phthalocyanine Blue BN (CAS 147-14-8).

In certain implementations, the copper phthalocyanine is a halogenated copper phthalocyanine. As an example, the pigment can be Phthalocyanine Green 6G (CAS 14302-13-7). As another example, the pigment can be polychlorinated (Cu II) phthalocyanine, such as Phthalocyanine Green G (CAS 1328-45-6 and 1328-53-6).

Non-limiting examples of suitable pigments include Sunsperse™ Green 7 (Pigment Green 7 dispersed in water, available from Sun Chemical Corp. Performance Pigments Cincinnati, Ohio, USA), Sunsperse™ EXP 006-102 and 006-95B (Pigment Green 7 dispersed in oil, available from Sun Chemical Corp. Performance Pigments, Cincinnati, Ohio, USA), and Pigment Green 7 powder (available from Hercules Exports, Mumbai, India).

[E] Silicone Surfactant

In some implementations, it can be advantageous to further include one (or more) silicone surfactants in combinations that further include one or more pigments.

[1]

In some implementations, the silicone surfactant is (or includes) a silicone polyether.

In certain implementations, the silicone surfactant is (or includes) a silicone polyether having a suitable alkoxy group with hydrogen end groups (H-capped), methyl end groups ($CH_3$-capped), or acetyl end groups ($COCH_3$-capped). In certain implementations, the silicone surfactant is (or includes) a trisiloxane having a suitable alkoxy group with hydrogen end groups (H-capped), methyl end groups ($CH_3$-capped), or acetyl end groups ($COCH_3$-capped).

In certain implementations, the silicone surfactant is (or includes) a silicone polyether of the formula I:

$$\text{(I)}\quad CH_3-\underset{\underset{CH_3}{|}}{\overset{\overset{CH_3}{|}}{Si}}-O-\underset{\underset{CH_3}{|}}{\overset{\overset{CH_3}{|}}{Si}}-O-\left(\underset{\underset{CH_3}{|}}{\overset{\overset{(CH_2)_3-(OCH_2CH_2)_x-OR}{|}}{Si}}-O\right)_n-Si(CH_3)_3$$

in which R is H, $CH_3$ or $COCH_3$; x is 1 to 24; and n is 0 or $\geq 1$.

In certain implementations, the silicone surfactant is (or includes) a silicone polyether of the formula I wherein R=H; x=1 to 24; and n=0; e.g., a silicone polyether of the formula I wherein n=0; x=1-24; the average x=8-10; and R=H.

In certain implementations, the silicone surfactant is (or includes) a silicone polyether of the formula I wherein R=H; x=1 to 24; and n≥1.

In certain implementations, the silicone surfactant is (or includes) a silicone polyether of the formula I wherein R=$CH_3$; x=1 to 24; and n=0.

In certain implementations, the silicone surfactant is (or includes) a silicone polyether of the formula I wherein R=$CH_3$; x=1 to 24; and n≥1.

In certain implementations, the silicone surfactant is (or includes) a silicone polyether of the formula I wherein R=$COCH_3$; x=1 to 24; and n=0; e.g., a silicone polyether of the formula I wherein n=0; x=1-24, the average x=8-10; and R=$COCH_3$.

In certain implementations, the silicone surfactant is (or includes) a silicone polyether of the formula I wherein R=$COCH_3$; x=1 to 24; and n≥1.

In certain implementations, the silicone surfactant is (or includes) an H-capped dimethyl methyl (polyethylene oxide) silicone polymer; e.g., having a molecular weight (or relative molar mass) from 200 to 6000.

In certain implementations, the silicone surfactant is (or includes) a silicone polyether of the formula II:

$$\text{(II)}\quad (CH_3)_3Si-O-\underset{\underset{CH_3}{|}}{\overset{\overset{CH_3}{|}}{(SiO)_b}}-\underset{\underset{CH_3}{|}}{\overset{\overset{CH_2CH_2CH_2O(CH_2CH_2O)_cH}{|}}{Si}}-O-Si(CH_3)_3$$

wherein c=2-16; and b=2-70. In certain implementations, the average b=44. In certain implementations, the average c=10. In certain implementations, the average b=44, and the average c=10.

In certain implementations, the silicone surfactant is (or includes) an H-capped trisiloxane, such as a silicone polyether of the formula III:

$$\text{(III)}\quad (CH_3)_3Si-O-\underset{\underset{CH_3}{|}}{\overset{\overset{CH_2CH_2CH_2O(CH_2CH_2O)_dH}{|}}{Si}}-O-Si(CH_3)_3$$

wherein d=1-24. In certain implementations, d=1-20. In certain implementations, the average d=8-10 (e.g., 8).

In certain implementations, the silicone surfactant is (or includes) a silicone copolyol, containing a hydrogen end group and one pendant polyethylene oxide group and has an average molecular weight between about 600 to about 1000 Daltons. In certain implementations, the silicone surfactant is (or includes) a trisiloxane with an ethoxylated alkyl group having a hydrogen end group (H-End); e.g., having a number of ethoxylation groups in the range of 1-20. In certain implementations, the silicone surfactant the silicone surfactant is (or includes) a methyl (propylhydroxide, ethoxylated) bis(trimethylsiloxy) silane; e.g., a dimethyl, methyl (polyethylene oxide) silicone polymer.

[2]

In some implementations, commercial preparations of the silicone surfactants may or may not contain small amounts of polyethylene glycols (PEG) or other low molecular weight polydimethyl siloxanes (PDMS).

In some implementations, the silicone surfactant further includes a polyethylene glycol.

In certain implementations, the polyethylene glycol is (or includes) a polyethylene glycol of the formula IV:

$$R^1-O-(CH_2CH_2O)_f-R^2$$

wherein $R^1$=H or $CH_2$=CH—$CH_2$ or $COCH_3$; $R^2$=H or $CH_2$=CH—$CH_2$ or $COCH_3$; and f≥1.

In certain implementations, the polyethylene glycol has a relatively low molecular weight, e.g. from 300 Daltons to 1500 Daltons. In certain implementations, the polyethylene glycol is a low molecular weight polyethylene glycol allyl ether, such as a low molecular weight polyethylene glycol mono-allyl ether having an average molecular of from about 300 to about 600 Daltons and having from 1 to 20 moles of ethylene glycol with an average ethylene oxide unit (EO) of 8 to 10.

In certain implementations, the polyethylene glycol is (or includes) a polyethylene glycol of the formula IV wherein $R^1$=$CH_2$=CH—$CH_2$, $R^2$=H, and f=1-20 with an average f=8, a polyethylene glycol of the formula IV wherein $R^1$=$CH_2$=CH—$CH_2$ or $COCH_3$, and $R^2$=$COCH_3$, a polyethylene glycol of the formula IV wherein $R^1$=$CH_2$=CH—$CH_2$, and $R^2$=H, or any combination thereof.

In certain implementations, the polyethylene glycol is (or includes) a polyethylene glycol of the formula IV wherein $R^1$=$CH_2$=CH—$CH_2$ or $COCH_3$, and $R^2$=$COCH_3$, a polyethylene glycol of the formula IV wherein $R^1$=$CH_2$=CH—$CH_2$, and $R^2$=H, or any combination thereof.

In certain implementations, the polyethylene glycol is (or includes) a polyethylene glycol of the formula IV wherein $R^1$=$CH_2$=CH—$CH_2$, $R^2$=H, and f=1-20 with an average f=8.

In certain implementations, the polyethylene glycol is (or includes) a polyethylene glycol of the formula IV wherein $R^1$=$CH_2$=CH—$CH_2$ or $COCH_3$, and $R^2$=$COCH_3$.

In certain implementations, the polyethylene glycol is (or includes) a polyethylene glycol of the formula IV wherein $R^1$=$CH_2$=CH—$CH_2$, and $R^2$=H.

Non-limiting examples of suitable polyethylene glycols may include Polyglykol A500 (available from Clariant).

In certain implementations, the silicone surfactant includes from 10 to 30 weight percent of a polyethylene glycol as described anywhere herein.

[3]

Non-limiting examples of suitable silicone surfactants may include Sylgard™ 309 (available from Dow Corning, Midland, Mich., USA), Silfsurf™ A008-UP (available from Siltech Corp. Toronto, ON, Canada), Lambent MFF 199 SW (available from Lambent Technologies Corp., Gurnee, Ill., USA), and Lambent MFF 159-100 (available from Lambent Technologies Corp., Gurnee, Ill., USA).

[F] Anti-Settling Agent

In some implementations, the combination can include one (or more) "anti-settling agents," which reduce the likelihood of having solids suspended in a dispersion from settling out under the influence of gravity.

In some implementations, the anti-setting agent is (or includes) a metal oxide and/or an organically modified clay.

In some implementations, the anti-setting agent is (or includes) a metal oxide.

In certain implementations, the anti-setting agent is (or includes) a fumed metal oxide and/or a precipitated metal oxide.

In certain implementations, the anti-setting agent is (or includes) one or more of the following forms of silica: precipitated silica (e.g., an untreated, precipitated silica) or fumed silica (e.g., an untreated, fumed silica). As used herein, the term "untreated fumed silica", or the like, is used to refer to a hydrophilic fumed silica. As used herein, the term "treated fumed silica", or the like, is used to refer to a hydrophobic fumed silica.

In some implementations, the anti-settling agent is (or includes) an organically modified clay. In certain implementations, the anti-setting agent is (or includes) one or more of the following organically modified clays: an organically modified smectite clay, an organically modified hectorite clay, an organically modified bentonite clay, an organically modified montmorillonite clay and an organically modified attapulgite clay.

In certain implementations, the organically modified clay is activated by a chemical activator.

In certain implementations, the chemical activator includes a low-molecular-weight polar organic compound, e.g., a least one compound selected from the group consisting of a low-molecular weight ketone, a low-molecular weight alcohol and propylene carbonate.

In certain implementations, the chemical activator includes water and at least one compound selected from the group consisting of a low-molecular weight ketone, a low-molecular weight alcohol and propylene carbonate.

In certain implementations, the chemical activator includes a low-molecular weight ketone; or a low-molecular weight ketone and water (such as a low molecular weight ketone and water in a weight ratio of 95/5). An example of a low-molecular weight ketone is acetone.

In certain implementations, the chemical activator includes a low-molecular weight alcohol; or a low-molecular weight alcohol and water (such as a low-molecular weight alcohol and water in a weight ratio of 95/5). Examples of low-molecular weight alcohols include methanol or ethanol.

In certain implementations, the chemical activator includes propylene carbonate; or propylene carbonate and water (such as, propylene carbonate and water in a weight ratio of 95/5).

[G] Water

In some implementations, the combinations can further include water.

In some implementations, the pigment is dispersed in water before it is added to the remaining components of the combination (typically water is 1:1 weight percent with with pigment), resulting in, e.g., the presence of 3 parts per weight of water in the combination.

In some implementations, the combinations can further include water, e.g., as a diluent, e.g., as a diluent added prior to application of the combinations to a plant (e.g., a turfgrass).

In some implementations, the combinations can further include both sources of water described above.

In some implementations the water is distilled water and/or other waters having a low mineral electrolyte content.

[H] Other Components

In some implementations, the combinations further include one or more other components that are customary additives or adjuvants for the preparation of compositions in the field of crop protection and/or components that are inert (e.g., may not materially affect the activity and/or overall performance of the combinations) and/or one or more other active components. As an example, the combinations can further include customary additives or adjuvants that may be present in a commercially available conventional chemical fungicide.

In some implementations, the combinations include only combinations of the components set forth is sections [A] through [G] above.

In certain implementations, the combinations do not include one or more other components that are customary additives or adjuvants for the preparation of compositions in the field of crop protection and/or components that are inert (e.g., may not materially affect the activity and/or overall performance of the combinations) and/or one or more other active components that are other than conventional chemical fungicides.

In certain implementations, the combinations are free of one or more other components that are customary additives or adjuvants for the preparation of compositions in the field of crop protection and/or components that are inert (e.g., may not materially affect the activity and/or overall performance of the combinations) and/or one or more other active components that are other than conventional chemical fungicides; (e.g., the combinations contain less than 5%, less than 4%, less than 3%, less than 2%, less than 1% (w/w or w/v) of one or more other components that are customary additives or adjuvants for the preparation of compositions in the field of turf or field crop protection and/or components that are inert (e.g., may not materially affect the activity and/or overall performance of the combinations) and/or one or more other active components that are other than conventional chemical fungicides.

In some implementations, the combinations are substantially free of one or more other components that are customary additives or adjuvants for the preparation of compositions in the field of crop protection and/or components that are inert (e.g., may not materially affect the activity and/or overall performance of the combinations) and/or one or more other active components that are other than conventional chemical fungicides (e.g., the combinations contain less than 0.5%, less than 0.2, less than 0.1, less than 0.05% (w/w or w/v), do not include a detectable amount of one or more other components that are customary additives or adjuvants for the preparation of compositions in the field of turf or field crop protection and/or components that are inert (e.g., may not materially affect the activity and/or overall performance of the combinations) and/or one or more other that are other than conventional chemical fungicides.

II. Non-Limiting Combinations of Components

[A] Combinations that Include a Single Composition

[1]

In some implementations, the combinations can be in the form of a single composition (e.g., contained within a storage pack or a vessel suitable for applying the composition to a plant, e.g., turf grass). These compositions are sometimes referred to herein (without limitation, e.g., as to quantity or application mode) as a 1-pack formulations or concentrates in the absence of water for dilution.

In some implementations, the composition includes one (or more) paraffinic oils, which can include any one or more of the features described in any one or more of sections [I][B][1], [I][B][2], and [I][B][3] above.

In some implementations, the combination further includes (but is not limited to) one or more of the following:

(ii) one (or more) conventional chemical fungicides, which can include any one or more of the features described in any one or more of sections [I][A][1] and/or [I][A][2] (e.g., one or more DMI fungicides and/or one or more QoI fungicides);

(iii) one (or more) emulsifiers, which can include any one or more of the features described in any one or more of sections [I][C][1], [I][C][2], and [I][C][3] above;

(iv) one (or more) pigments which can include any one or more of the features described in section [I][D] above;

(v) one (or more) silicone surfactants, which can include any one or more of the features described in any one or more of sections [I][E][1], [I][E][2], and [I][E][3] above;

(vi) one (or more) anti-settling agents, which can include any one or more of the features described in section [I][D] above; and (vii) one (or more) components described in section [I][H].

In some implementations, the composition includes (i) and (iii).

In some implementations, the composition includes (i), (iii), and (vi).

In some implementations, the composition includes (i), (iii), (iv), and (v).

In some implementations, the composition includes (i), (iii), (iv), (v), and (vi).

In some implementations, the composition includes (i), (ii), and (iii).

In some implementations, the composition includes (i), (ii), (iii), and (vi).

In some implementations, the composition includes (i), (ii), (iii), (iv), and (v).

In some implementations, the composition includes (i), (ii), (iii), (iv), (v), and (vi).

[2] Concentrates

In some of the implementations described in section [II][A][1], one or more of the following applies:

(2-a) the weight ratio of paraffinic oil to the emulsifier is from 10:1 to 500:1 (e.g., from 45:1 to 55:1, e.g., 49:1, 50:1);

(2-b) the weight ratio of paraffinic oil to the pigment is from 5:1 to 100:1 (e.g., from 25:1 to 35:1, e.g., 28:1, 30:1);

(2-c) the weight ratio of pigment to the silicone surfactant is from 2:1 to 50:1 (e.g., from 3:1 to 6:1, e.g., 4.5:1);

(2-d) the weight ratio of paraffinic oil to the conventional chemical fungicide (e.g., one or more DMI fungicides and/or one or more QoI fungicides) is from 2:1 to 10000:1 (e.g., from 100:1 to 160:1; from 90:1 to 120:1, e.g., 111:1, 110:1; from 130:1 to 150:1, e.g., 139:1, 140:1).

In certain implementations, (2-a) applies; or (2-a), (2-b) and (2-c) apply; or (2-b), and (2-c) apply. In certain implementations, (2-d) further applies to any one of the above-listed combinations of (2-a), (2-b) and (2-c).

In some of the implementations described in section [II][A][1], one or more of the following applies:

(2-aa) the concentrate includes from 50 to 300 parts per weight (e.g., 200-300, e.g., 260; e.g., 50-150, e.g., 100) parts per weight of the paraffinic oil;

(2-bb) the concentrate includes from 1 to 10 parts per weight (e.g., 3-7, e.g., 5; e.g., 1-5, e.g., 1.9, e.g., 2) parts per weight of the emulsifier;

(2-cc) the concentrate includes from 1 to 15 parts per weight (e.g., 7-11, e.g., 9; e.g., 2-5, e.g., 3.5) parts per weight of the pigment;

(2-dd) the concentrate includes from 0.1 to 10 parts per weight (e.g., 0.5-1, e.g., 0.8, e.g., e.g., 2-5, e.g., 3.1) parts per weight of the silicone surfactant;

(2-ee) the concentrate includes from 0.5 to 20 parts per weight (e.g., 6-10, e.g., 8; e.g., 2-5, e.g., 3.1) parts per weight of the anti-settling agent; or (2-ff) the concentrate includes from 0.01 to 10 parts per weight (e.g., 0.5-1, e.g., 0.8, e.g., e.g., 1-3, e.g., 2) parts per weight of the conventional chemical fungicide.

In certain implementations, (2-aa) and (2-bb) apply; or (2-cc) and (2-dd) apply; or (2-aa), (2-bb), and (2-ff) apply; or (2-cc), (2-dd), and (2-ff) apply; or (2-aa), (2-bb), (2-cc), and (2-dd) apply, or (2-aa), (2-bb), (2-cc), (2-dd), and (2-ff) apply. In certain implementations, (2-ee) further applies to each of the above-listed implementations.

In some implementations, any one or more of the features described in one or more of (2-a) and (2-d) can be combined with any one or more of the features described in one or more of (2-aa) and (2-ff).

In some implementations, the pigment is dispersed in compatible oil, e.g., a paraffinic oil, e.g., the same paraffinic oil as is used to provide the fungicidal properties as described herein, for addition to the other components of the combinations described herein. In certain implementations, a silicone surfactant and/or emulsifier and/or anti-settling agent can be included, e.g., to stabilize the pigment in the oil-based combination.

For example, polychlorinated Cu (II) phthalocyanine can be dispersed in a paraffinic oil, such as N65DW (available from Petro-Canada) to provide about 18% polychlorinated CU (II) phthalocyanine (SUNSPERSE® EXP 006-102, available from Sun Chemical Corp. Performance Pigments, Cincinnati, Ohio USA) prior to mixing with the remaining components. In certain implementations, a silicone surfactant and/or emulsifier and/or anti-settling agent can be included. While not wishing to be bound by theory, it is believed that the addition of these components can provide an intermolecular hydrophilic and lipophilic balance within the fungicidal formulation so as to substantially prevent the polychlorinated Cu (II) phthalocyanine from separating out of suspension during application, e.g., to a turf grass.

In some of the implementations described in section [II][A][1], the composition includes the components present in Civitas™ 1-pack and those present in commercially available conventional chemical fungicides described anywhere herein.

[3]

In some of the implementations described in sections [II]A[1] and [II][A][2], the composition further includes water. In certain implementations, weight percent ratio of the undiluted composition to water is from 1:1 to 1:100 (e.g., from 1-50, 1-30, 1-20, 1-15). In certain implementations, the weight percent of the paraffinic oil in the diluted compositions is from 2-50 weight percent (e.g., 15%). In certain implementations, the composition is in the form of an oil in water emulsion as described anywhere herein.

In some implementations, the pigment is dispersed in water for addition to the other components of the combinations described herein. In certain implementations, a silicone surfactant and/or emulsifier and/or anti-settling agent can be included, e.g., to stabilize the pigment in the oil/water-based combination.

For example, polychlorinated Cu (II) phthalocyanine can be dispersed in a water to provide about 40% polychlorinated CU (II) phthalocyanine (SUNSPERSE® GREEN 7, available from Sun Chemical Corp. Performance Pigments, Cincinnati, Ohio USA) prior to mixing with the remaining components. In certain implementations, a silicone surfactant and/or emulsifier and/or anti-settling agent can be included. While not wishing to be bound by theory, it is believed that the addition of these components can provide an intermolecular network so as to substantially prevent the polychlorinated Cu (II) phthalocyanine from separating out of suspension during application, e.g., to a turf grass.

[B] Combinations that Include Two or More Compositions

[1]

In some implementations, the combinations include two or more separately contained (e.g., packaged) compositions, each containing one or more of the components described in sections [I][A]-[I][F] and [I][H]. These implementations are sometimes referred to (as appropriate and without limitation, e.g., as to quantity or application mode) as 2-pack and 3-pack formulations, compositions, or concentrates in the absence of water for dilution.

In some implementations, the combinations include a first and separately contained composition and a second and separately contained composition, in which:

(1) the first and separately contained composition includes:
one (or more) paraffinic oils, which can include any one or more of the features described in any one or more of sections [I][B][1], [I][B][2], and [I][B][3] above;
one (or more) conventional chemical fungicides, which can include any one or more of the features described in any one or more of sections [I][A][1] and/or [I][A][2] (e.g., one or more DMI fungicides and/or one or more QoI fungicides); and
one (or more) emulsifiers, which can include any one or more of the features described in any one or more of sections [I][C][1], [I][C][2], and [I][C][3] above; and (2) the second and separately contained composition includes:
one (or more) pigments, which can include any one or more of the features described in section [I][D] above and
one (or more) silicone surfactants, which can include any one or more of the features described in any one or more of sections [I][E][1], [I][E][2], and [I][E][3] above.

In some implementations, the combinations include a first and separately contained composition and a second and separately contained composition, in which:

(1) the first and separately contained composition includes:
one (or more) paraffinic oils, which can include any one or more of the features described in any one or more of sections [I][B][1], [I][B][2], and [I][B][3] above;
one (or more) emulsifiers, which can include any one or more of the features described in any one or more of sections [I][C][1], [I][C][2], and [I][C][3] above;
one (or more) pigments, which can include any one or more of the features described in section [I][D] above;
one (or more) silicone surfactants, which can include any one or more of the features described in any one or more of sections [I][E][1], [I][E][2], and [I][E][3] above; and
one (or more) anti-settling agents, which can include any one or more of the features described in section [I][D] above; and (2) the second and separately contained composition includes:
one (or more) conventional chemical fungicides, which can include any one or more of the features described in any one or more of sections [I][A][1] and/or [I][A][2] (e.g., one or more DMI fungicides and/or one or more QoI fungicides).

In some implementations, the combinations include a first and separately contained composition and a second and separately contained composition, in which:

(1) the first and separately contained composition includes:
one (or more) paraffinic oils, which can include any one or more of the features described in any one or more of sections [I][B][1], [I][B][2], and [I][B][3] above; and
one (or more) emulsifiers, which can include any one or more of the features described in any one or more of sections [I][C][1], [I][C][2], and [I][C][3] above;

(2) the second and separately contained composition includes:
one (or more) conventional chemical fungicides, which can include any one or more of the features described in any one or more of sections [I][A][1] and/or [I][A][2] (e.g., one or more DMI fungicides and/or one or more QoI fungicides);

one (or more) pigments, which can include any one or more of the features described in section [I][D] above; and one (or more) silicone surfactants, which can include any one or more of the features described in any one or more of sections [I][E][1], [I][E][2], and [I][E][3] above.

In some implementations, the combinations include a first and separately contained composition and a second and separately contained composition, in which:

(1) the first and separately contained composition includes:

one (or more) paraffinic oils, which can include any one or more of the features described in any one or more of sections [I][B][1], [I][B][2], and [I][B][3] above; and one (or more) emulsifiers, which can include any one or more of the features described in any one or more of sections [I][C][1], [I][C][2], and [I][C][3] above;

(2) the second and separately contained composition includes:

one (or more) pigments, which can include any one or more of the features described in section [I][D] above; and one (or more) silicone surfactants, which can include any one or more of the features described in any one or more of sections [I][E][1], [I][E][2], and [I][E][3] above.

In some implementations, the combinations include a first and separately contained composition, a second and separately contained composition, and a third and separately contained composition, wherein:

(1) the first and separately contained composition includes:

one (or more) paraffinic oils, which can include any one or more of the features described in any one or more of sections [I][B][1], [I][B][2], and [I][B][3] above; and one (or more) emulsifiers, which can include any one or more of the features described in any one or more of sections [I][C][1], [I][C][2], and [I][C][3] above; and (2) the second and separately contained composition includes:

one (or more) pigments, which can include any one or more of the features described in section [I][D] above and one (or more) silicone surfactants, which can include any one or more of the features described in any one or more of sections [I][E][1], [I][E][2], and [I][E][3] above; and (3) the third and separately contained composition includes:

one (or more) conventional chemical fungicides, which can include any one or more of the features described in any one or more of sections [I][A][1] and/or [I][A][2] (e.g., one or more DMI fungicides and/or one or more QoI fungicides).

[2] Component Amounts in Combinations Having Two or More Composition (Concentrates)

In some of the implementations described in section [II][B][1], one or more of the following applies:

(2-aaa) the weight ratio of paraffinic oil to the emulsifier is from 10:1 to 500:1 (e.g., from 45:1 to 55:1, e.g., 49:1, 50:1);

(2-bbb) the weight ratio of paraffinic oil in a composition to the pigment (in the same or a different composition) is from 5:1 to 100:1 (e.g., from 25:1 to 35:1, e.g., 28:1, 30:1);

(2-ccc) the weight ratio of pigment to the silicone surfactant is from 2:1 to 50:1 (e.g., from 3:1 to 6:1, e.g., 4.5:1);

(2-ddd) the weight ratio of paraffinic oil in a composition to the weight ratio of paraffinic oil to the conventional chemical fungicide (e.g., one or more DMI fungicides and/or one or more QoI fungicides) in the same or a different composition is from 2:1 to 10,000:1 (e.g., from 100:1 to 160:1; from 90:1 to 120:1, e.g., 111:1, 110:1; from 130:1 to 150:1, e.g., 139:1, 140:1).

In certain implementations, (2-aaa) applies; or (2-aaa), (2-bbb) and (2-ccc) apply; or (2-bbb), and (2-ccc) apply. In certain implementations, (2-ddd) further applies to any one of the above-listed combinations of (2-aaa), (2-bbb) and (2-ccc).

In some of the implementations described in section [II][B][1], one or more of the following applies:

(2-aaaa) the composition (concentrate) includes from 50 to 300 parts per weight (e.g., 100) parts per weight of the paraffinic oil;

(2-bbbb) the composition (concentrate) includes from 1 to 10 parts per weight (e.g., 1.9, e.g., 2) parts per weight of the emulsifier;

(2-cccc) the composition (concentrate) includes from 1 to 10 parts per weight (e.g., 3.5) parts per weight of the pigment;

(2-dddd) the composition (concentrate) includes from 0.1 to 10 parts per weight (e.g., 0.8) parts per weight of the silicone surfactant;

(2-eeee) the composition (concentrate) includes from 0.5 to 20 parts per weight (e.g., 3.1) parts per weight of the anti-settling agent; or (2-ffff) the composition (concentrate) includes from 0.01 to 10 parts per weight (e.g., 0.8) parts per weight of the conventional chemical fungicide (e.g., one or more DMI fungicides and/or one or more QoI fungicides).

In certain implementations, (2-aaaa) and (2-bbbb) apply; or (2-aaaa) through (2-eeee) apply; or (2-ffff) applies; or (2-cccc), (2-dddd), and (2-ffff) apply; or (2-cccc) and (2-dddd) apply.

In certain implementations, (2-aaaa) through (2-eeee) apply in a composition (concentrate), and (2-ffff) applies in another composition (concentrate).

In certain implementations, (2-aaaa) and (2-bbbb) apply in a composition (concentrate), and (2-cccc), (2-dddd), and (2-ffff) apply in another composition (concentrate).

In certain implementations, (2-aaaa) and (2-bbbb) apply in a composition (concentrate), and (2-cccc) and (2-dddd) apply in another composition (concentrate).

In certain implementations, (2-aaaa) through (2-eeee) apply in a composition (concentrate), (2-cccc) and (2-dddd) apply in a second composition (concentrate), and (2-ffff) applies in a third composition (concentrate).

In some implementations, any one or more of the features described in one or more of (2-aaa) and (2-ddd) can be combined with any one or more of the features described in one or more of (2-aaaa) and (2-ffff).

In some of the implementations described in section [II][B][1], the second composition can further include water (e.g., resulting in a dispersion of the pigment in the water).

In some of the implementations described in section [II][B][1], the first and second composition include the components present in Civitas™ 2-pack (Civitas™/Harmonizer™ 16:1) and those present in commercially available conventional chemical fungicides described anywhere herein.

In some of the implementations described in section [II][B][1], the first and second composition include the components present in Civitas™ 2-pack (Civitas™/Harmonizer™ 16:1), and the third composition includes the components present in commercially available conventional chemical fungicides described anywhere herein.

[3]

In some of the implementations described in sections [II][B][1] and [II][B][2], each of the compositions, independently, further includes water. In certain implementations, the combination of compositions (concentrates) described above are combined and diluted with water ((e.g., spray volume of the diluted end product is 5 to 50 gal/acre, e.g., 10 to 20 gal/acre). In certain implementations, oil in the end product is from 80 to 640 oz/acre (other components can be calculated based on ratio with oil).

[C]

As the skilled artisan will appreciate, the weight percent of a given component(s) can vary, e.g., due to dilution with water or whether the combination is in the form of a single composition or two or more separately contained compositions. In some implementations, the weight ratio of any two or more components is essentially the same regardless of whether the combination is in the form of a single composition (diluted with water or undiluted) or in the form two or more separately contained compositions (diluted with water or undiluted). In the latter case, this can be achieved by adjusting the component amounts in each of the separately contained compositions to match, for example, a weight percent ratio employed in single composition combination.

III. Application of Combinations

In general, the combinations can be applied to the plant by conventional methods known in the art, e.g., spraying, misting, sprinkling, pouring, or any other suitable method. The compositions may be reapplied as required.

In some implementations, the combinations include both paraffinic oil and water. It is advantageous to apply such combinations as oil-in-water (O/W) emulsions. In some implementations, an oil-in-water emulsion is prepared by a process that includes combining the paraffinic oil, water, and any other components and the paraffinic oil and applying shear until the emulsion is obtained. In other implementations, an oil-in-water emulsion is prepared by a process that includes combining the paraffinic oil, water, and any other components at the nozzle of a spray gun.

In other implementations, the combinations can include two or more separately contained (e.g., packaged) compositions, each containing one or more of the above-mentioned components. Said compositions can be combined and applied to a plant (e.g., crop plant) with or without prior dilution with water; or each composition can be applied separately to the same plant (e.g., crop plant) either simultaneously or sequentially, and each independently applied with or without prior dilution with water.

In the above-described implementations, application of any one (or more) compositions can be repeated one or more times.

In some implementations, any one or more of the following can apply:
the paraffinic oil is applied to a plant (e.g., crop plant) at a rate from 80 to 640 oz/acre (e.g., from 100 oz/acre to 400 oz/acre);
the paraffinic oil is used or applied to the plant (e.g., crop plant) 1 to 10 times during growing season until harvest, with intervals greater or equal to 7 days;
conventional chemical fungicide (e.g., one or more DMI fungicides and/or one or more QoI fungicides) is applied to a plant (e.g., crop plant) at a rate from 0.01 lbs/acre to 1.50 lbs/acre;
DMI fungicide (e.g., propioconazole) is applied to a plant (e.g., crop plant) at a rate from 0.015 lbs/acre to 0.6 lbs/acre (e.g., from 0.060 lbs/acre to 0.25 lbs/acre); or a rate from (e.g., tebuconazole, prothioconazole) 0.02 to about 0.45 lbs./acre; or at a rate from (e.g., tetaconazole) 0.015 to about 0.15 lbs./acre;
QoI fungicide is applied to a plant (e.g., crop plant) at a rate from 0.01 lbs/acre to 0.50 lbs/acre (e.g., azoxystrobin); or a rate from 0.02 lbs/acre to 0.40 lbs/acre (e.g., pyraclostrobin); or a rate from and
conventional chemical fungicide (e.g., one or more DMI fungicides and/or one or more QoI fungicides) is used or applied to the plant 1 to 5 times during growing season until harvest, with intervals greater or equal to 14 days.

In certain implementations, the interval rates for the paraffinic oil and the conventional chemical fungicide (e.g., one or more DMI fungicides and/or one or more QoI fungicides) overlap (e.g., when tank-mixed and applied at the same time). In other implementations, the interval rates for the paraffinic oil and the conventional chemical fungicide (e.g., one or more DMI fungicides and/or one or more QoI fungicides) do not overlap (e.g., when applied separately and/or sequentially).

In some implementations, the combinations described herein can be prepared using the methods described in, for example, WO 2009/155693.

The features described in section III above can be combined with any one or more of the features described in sections I and II above.

In some implementations, the fungal pathogen may be, for example, *Gymnosporangium juniperi-virginianae, Cronartium ribicola, Hemileia vastatrix Puccinia graminis, Puccinia coronata, Puccinia hemerocallidis, Puccinia persistens* subsp. *Triticina, Puccinia sriiformis, Puccinia triticina, Phakopsora meibomiae, Phakopsora pachyrhizi, Uromyces phaseoli, Uromyces appendeculatus, Fusarium graminearum, Bipolaris sorokiniana*, or a combination thereof. In alternative implementations, the fungal disease may be, for example: cedar-apple rust, which attacks, for example, apple and pear and hawthorn); white pine blister rust, which attacks, for example, white pines and currants; coffee rust, which attacks, for example, the coffee plant; wheat stem rust, which attacks, for example, Kentucky bluegrass, barley, and wheat; crown rust, which attacks, for example, oats and ryegrass; soybean rust, which attacks, for example, soybean and various legumes; leaf rust, which attacks, for example, wheat; bean rust which attacks, for example, bean; Daylily rust, which attacks, for example, Daylily; wheat rust in grains, also known as "brown" or "red rust"); "yellow" or "stripe rust", which attacks, for example, wheat; spot blotch, which attacks, for example, wheat; and *Fusarium* head blight, which attacks, for example, wheat.

In alternative implementations, the fungal pathogen may be, for example, a fungus that blights leaf tissue in a crop plant. In selected implementations, the crop plant pathogen is the fungal pathogen *Gymnosporangium juniperi-virginianae*, and the disease may be, for example, cedar-apple rust. In alternative implementations, the crop plant pathogen is the fungal pathogen *Cronartium ribicola*, and the disease may be, for example, white pine blister rust. In selected implementations, the crop plant pathogen is the fungal pathogen, and the disease may be, for example, coffee rust. In alternative implementations, the crop plant pathogen is the fungal pathogen *Puccinia graminis*, and the disease may be, for example, wheat stem rust. In selected implementations, the crop plant pathogen is the fungal pathogen *Puccinia coronata*, and the disease may be, for example, crown rust. In alternative implementations, the crop plant pathogen is the fungal pathogen *Phakopsora meibomiae* or *Phakospora pachyrhizi*, and the disease may be, for example, soybean rust. In alternative implementations, the crop plant pathogen is the fungal pathogen *Uromyces phaseoli*, and the disease may be, for example, bean rust. In selected implementations, the crop plant pathogen is the fungal pathogen *Puccinia hemerocallidis*, and the disease may be, for example, Daylily rust. In alternative implementations, the crop plant pathogen is the fungal pathogen *Puccinia persistens* subsp. *triticina*, and the disease may be, for example, brown rust or red rust. In selected implementations, the crop plant pathogen is the fungal pathogen *Puccinia sriiformis*, and the disease may be, for example, yellow rust or strip rust. In alternative implementations, the crop plant pathogen is the fungal pathogen *Uromyces* appendeculatus, and the disease may be, for example, bean rust. In selected implementations, the crop plant pathogen is the fungal pathogen *Puccinia triticina*, and the disease may be, for example, leaf rust. In alternative implementations, the crop plant fungal pathogen is *Fusarium graminearum* and the disease may be, for example, *Fusarium* head blight. In selected implementations, the crop plant pathogen is the fungal pathogen *Bipolaris sorokiniana*, and the disease may be, for example, spot blotch.

In various additional implementations wherein the crop plant is wheat, the fungal pathogen may be any one of the fungal pathogens listed in the right hand column of Table 1, and the disease may be the corresponding disease of wheat listed in the left column of Table 1.

TABLE 1

Fungal diseases of wheat.

| Disease | Causative fungal pathogen(s) |
|---|---|
| *Alternaria* leaf blight | *Alternaria triticina* |
| Anthracnose | *Colletotrichum graminicola* |
|  | *Glomerella graminicola* [teleomorph] |
| *Ascochyta* leaf spot | *Ascochyta tritici* |
| *Aureobasidium* decay | *Microdochium bolleyi* = |
|  | *Aureobasidium bolleyi* |
| Black head molds = sooty molds | *Alternaria* spp. |
|  | *Cladosporium* spp. |
|  | *Epicoccum* spp. |
|  | *Sporobolomyces* spp. |
|  | *Stemphylium* spp. and other genera |
| *Cephalosporium* stripe | *Hymenula cerealis* = |
|  | *Cephalosporium gramineum* |
| Common bunt = stinking smut | *Tilletia tritici* = |
|  | *Tilletia caries* |
|  | *Tilletia laevis* = |
|  | *Tilletia foetida* |
| Common root rot | *Cochliobolus sativus* [teleomorph] |
|  | *Bipolaris sorokiniana* [anamorph] = |
|  | *Helminthosporium sativum* |
| Cottony snow mold | *Coprinus psychromorbidus* |
| Crown rot = foot rot, seedling blight, dryland root rot | *Fusarium* spp. |
|  | *Fusarium pseudograminearum* |
|  | *Gibberella zeae* |
|  | *Fusarium graminearum* Group II [anamorph] |
|  | *Gibberella avenacea* |
|  | *Fusarium avenaceum* [anamorph] |
|  | *Fusarium culmorum* |
| *Dilophospora* leaf spot = twist | *Dilophospora alopecuri* |
| Downy mildew = crazy top | *Sclerophthora macrospora* |
| Dwarf bunt | *Tilletia controversa* |
| Ergot | *Claviceps purpurea* |
|  | *Sphacelia segetum* [anamorph] |

TABLE 1-continued

Fungal diseases of wheat.

| Disease | Causative fungal pathogen(s) |
|---|---|
| Eyespot = foot rot, strawbreaker | *Tapesia yallundae* |
|  | *Ramulispora herpotrichoides* [anamorph] = |
|  | *Pseudocercosporella herpotrichoides* W-pathotype |
|  | *Tapesia acuformis* |
|  | *Ramulispora acuformis* [anamorph] = |
|  | *Pseudocercosporella herpotrichoides* var. *acuformis* R-pathoytpe |
| False eyespot | *Gibellina cerealis* |
| Flag smut | *Urocystis agropyri* |
| Foot rot = dryland foot rot | *Fusarium* spp. |
| Halo spot | *Pseudoseptoria donacis* = |
|  | *Selenophoma donacis* |
| Karnal bunt = partial bunt | *Tilletia indica* = |
|  | *Neovossia indica* |
| Leaf rust = brown rust | *Puccinia triticina* = |
|  | *Puccinia recondita* f.sp. *tritici* |
|  | *Puccinia tritici-duri* |
| *Leptosphaeria* leaf spot | *Phaeosphaeria herpotrichoides* = |
|  | *Leptosphaeria herpotrichoides* |
|  | *Stagonospora* sp. [anamorph] |
| Loose smut | *Ustilago tritici* = |
|  | *Ustilago segetum* var. *tritici* |
|  | *Ustilago segetum* var. *nuda* |
|  | *Ustilago segetum* var. *avenae* |
| *Microscopica* leaf spot | *Phaeosphaeria microscopica* = |
|  | *Leptosphaeria microscopica* |
| *Phoma* spot | *Phoma* spp. |
|  | *Phoma glomerata* |
|  | *Phoma sorghina* = |
|  | *Phoma insidiosa* |
| Pink snow mold = *Fusarium* patch | *Microdochium nivale* = |
|  | *Fusarium nivale* |
|  | *Monographella nivalis* [teleomorph] |
| *Platyspora* leaf spot | *Clathrospora pentamera* = |
|  | *Platyspora pentamera* |
| Powdery mildew | *Erysiphe graminis* f. sp. *tritici* |
|  | *Blumeria graminis* = |
|  | *Erysiphe graminis* |
|  | *Oidium monilioides* [anamorph] |
| *Pythium* root rot | *Pythium aphanidermatum* |
|  | *Pythium arrhenomanes* |
|  | *Pythium graminicola* |
|  | *Pythium myriotylum* |
|  | *Pythium volutum* |
| *Rhizoctonia* root rot | *Rhizoctonia solani* |
|  | *Thanatephorus cucumeris* [teleomorph] |
| Ring spot = Wirrega blotch | *Pyrenophora seminiperda* = |
|  | *Drechslera campanulata* |
|  | *Drechslera wirreganensis* |
| Scab = head blight | *Fusarium* spp. |
|  | *Gibberella zeae* |
|  | *Fusarium graminearum* Group II [anamorph] |
|  | *Gibberella avenacea* |
|  | *Fusarium avenaceum* [anamorph] |
|  | *Fusarium culmorum* |
|  | *Microdochium nivale* = |
|  | *Fusarium nivale* |
|  | *Monographella nivalis* [teleomorph] |
| *Sclerotinia* snow mold = snow scald | *Myriosclerotinia borealis* = |
|  | *Sclerotinia borealis* |
| *Sclerotium* wilt (see Southern blight) | *Sclerotium rolfsii* |
|  | *Athelia rolfsii* [teleomorph] |
| *Septoria* blotch | *Septoria tritici* |
|  | *Mycosphaerella graminicola* [teleomorph] |
| Sharp eyespot | *Rhizoctonia cerealis* |
|  | *Ceratobasidium cereale* [teleomorph] |
| Snow rot | *Pythium* spp. |
|  | *Pythium aristosporum* |
|  | *Pythium iwayamae* |
|  | *Pythium okanoganense* |

TABLE 1-continued

Fungal diseases of wheat.

| Disease | Causative fungal pathogen(s) |
|---|---|
| Southern blight = *Sclerotium* base rot | *Sclerotium rolfsii* *Athelia rolfsii* [teleomorph] |
| Speckled snow mold = gray snow mold or *Typhula* blight | *Typhula idahoensis* *Typhula incarnata* *Typhula ishikariensis* *Typhula ishikariensis* var. *canadensis* |
| Spot blotch | *Cochliobolus sativus* [teleomorph] *Bipolaris sorokiniana* [anamorph] = *Helminthosporium sativum* |
| *Stagonospora* blotch | *Phaeosphaeria avenaria* f. sp. *triticae* *Stagonospora avenae* f. sp. *triticae* [anamorph] = *Septoria avenae* f. sp. *triticea* *Phaeosphaeria nodorum* *Stagonospora nodorum* [anamorph] = *Septoria nodorum* |
| Stem rust = black rust | *Puccinia graminis* = *Puccinia graminis* f. sp. *tritici* (Ug99) |
| Storage molds | *Aspergillus* spp. *Penicillium* spp. and others |
| Stripe rust = yellow rust | *Puccinia striiformis* *Uredo glumarum* [anamorph] |
| Take-all | *Gaeumannomyces graminis* var. *tritici* *Gaeumannomyces graminis* var. *avenae* |
| Tan spot = yellow leaf spot, red smudge | *Pyrenophora tritici-repentis* *Drechslera tritici-repentis* [anamorph] |
| Tar spot | *Phyllachora graminis* *Linochora graminis* [anamorph] |
| Wheat Blast | *Magnaporthe grisea* |
| Zoosporic root rot | *Lagena radicicola* *Ligniera pilorum* *Olpidium brassicae* *Rhizophydium graminis* |

In various additional embodiments wherein the crop plant is of the genus *Zea*, the fungal pathogen may be any one of the fungal pathogens listed in the right hand column of Table 2, and the disease may be the corresponding disease of wheat listed in the left column of Table 2.

TABLE 2

Fungal diseases of maize.

| Disease | Causative fungal pathogen |
|---|---|
| Anthracnose leaf blight | *Colletotrichum graminicola* |
| Anthracnose stalk rot | *Glomerella graminicola* [teleomorph] *Glomerella tucumanensis* *Glomerella falcatum* [anamorph] |
| *Aspergillus* ear and kernel rot | *Aspergillus flavus* |
| Banded leaf and sheath spot | *Rhizoctonia solani* = *Rhizoctonia microsclerotia* *Thanatephorus cucumeris* [teleomorph] |
| Black bundle disease | *Acremonium strictum* = *Cephalosporium acremonium* |
| Black kernel rot | *Lasiodiplodia theobromae* = *Botryodiplodia theobromae* |
| Borde blanco | *Marasmiellus* sp. |
| Brown spot Black spot Stalk rot | *Physoderma maydis* |
| *Cephalosporium* kernel rot | *Acremonium strictum* = *Cephalosporium acremonium* |
| Charcoal rot | *Macrophomina phaseolina* |
| *Corticium* ear rot | *Thanatephorus cucumeris* = *Corticium sasakii* |
| *Curvularia* leaf spot | *Curvularia clavata* *Curvularia eragrostidis* = *Curvularia maculans* *Cochliobolus eragrostidis* [teleomorph] *Curvularia inaequalis* *Curvularia intermedia* *Cochliobolus intermedius* [teleomorph] *Curvularia lunata* *Cochliobolus lunatus* [teleomorph] *Curvularia pallescens* *Cochliobolus pallescens* [teleomorph] *Curvularia senegalensis* *Curvularia tuberculata* *Cochliobolus tuberculatus* [teleomorph] |
| *Didymella* leaf spot | *Didymella exitalis* |
| *Diplodia* ear rot and stalk rot | *Diplodia frumenti* *Botryosphaeria festucae* [teleomorph] |
| *Diplodia* ear rot Stalk rot Seed rot Seedling blight | *Diplodia maydis* |
| *Diplodia* leaf spot or leaf streak | *Stenocarpella macrospora* = *Diplodia macrospora* |
| Brown stripe downy mildew | *Sclerophthora rayssiae* |

TABLE 2-continued

| Fungal diseases of maize. | |
|---|---|
| Disease | Causative fungal pathogen |
| Crazy top downy mildew | *Sclerophthora macrospora* = *Sclerospora macrospora* |
| Green ear downy mildew | *Sclerospora graminicola* |
| *Graminicola* downy mildew | |
| Java downy mildew | *Peronosclerospora maydis* = *Sclerospora maydis* |
| Philippine downy mildew | *Peronosclerospora philippinensis* = *Sclerospora philippinensis* |
| Sorghum downy mildew | *Peronosclerospora sorghi* = *Sclerospora sorghi* |
| *Spontaneum* downy mildew | *Peronosclerospora spontanea* = *Sclerospora spontanea* |
| Sugarcane downy mildew | *Peronosclerospora sacchari* = *Sclerospora sacchari* |
| Dry ear rot | *Nigrospora oryzae* |
| Cob, kernel and stalk rot | *Khuskia oryzae* [teleomorph] |
| Ear rots, minor | *Alternaria alternata* = *Alternaria tenuis* |
| | *Aspergillus glaucus* |
| | *Aspergillus niger* |
| | *Aspergillus* spp. |
| | *Botrytis cinerea* |
| | *Botryotinia fuckeliana* [teleomorph] |
| | *Cunninghamella* sp. |
| | *Curvularia pallescens* |
| | *Doratomyces stemonitis* = *Cephalotrichum stemonitis* |
| | *Fusarium culmorum* |
| | *Gonatobotrys simplex* |
| | *Pithomyces maydicus* |
| | *Rhizopus microsporus* |
| | *Rhizopus stolonifer* = *Rhizopus nigricans* |
| | *Scopulariopsis brumptii* |
| Ergot | *Claviceps gigantea* |
| Horse's tooth | *Sphacelia* sp. [anamorph] |
| Eyespot | *Aureobasidium zeae* = *Kabatiella zeae* |
| *Fusarium* ear and stalk rot | *Fusarium subglutinans* = *Fusarium moniliforme* |
| *Fusarium* kernel, root and stalk rot, seed rot and seedling blight | *Fusarium moniliforme* *Gibberella fujikuroi* [teleomorph] |
| *Fusarium* stalk rot | *Fusarium avenaceum* |
| Seedling root rot | *Gibberella avenacea* [teleomorph] |
| *Gibberella* ear and stalk rot | *Gibberella zeae* *Fusarium graminearum* [anamorph] |
| Gray ear rot | *Botryosphaeria zeae* = *Physalospora zeae* *Macrophoma zeae* [anamorph] |
| Gray leaf spot | *Cercospora sorghi* = *Cercospora sorghi* |
| *Cercospora* leaf spot | *Cercospora zeae-maydis* |
| *Helminthosporium* root rot | *Exserohilum pedicellatum* = *Helminthosporium pedicellatum* *Setosphaeria pedicellata* [teleomorph] |
| *Hormodendrum* ear rot *Cladosporium* rot | *Cladosporium cladosporioides* = *Hormodendrum cladosporioides* *Cladosporium herbarum* *Mycosphaerella tassiana* [teleomorph] |
| *Hyalothyridium* leaf spot | *Hyalothyridium maydis* |
| Late wilt | *Cephalosporium maydis* |
| Leaf spots, minor | *Alternaria alternata* |
| | *Ascochyta maydis* |
| | *Ascochyta tritici* |
| | *Ascochyta zeicola* |
| | *Bipolaris victoriae* = *Helminthosporium victoriae* |
| | *Cochliobolus victoriae* [teleomorph] |
| | *Cochliobolus sativus* |
| | *Bipolaris sorokiniana* [anamorph] = *Helminthosporium sorokinianum* = *H. sativum* |
| | *Epicoccum nigrum* |
| | *Exserohilum prolatum* = *Drechslera prolata* |
| | *Setosphaeria prolata* [teleomorph] |
| | *Graphium penicillioides* |
| | *Leptosphaeria maydis* |
| | *Leptothyrium zeae* |
| | *Ophiosphaerella herpotricha* |
| | *Scolecosporiella* sp. [anamorph] |
| | *Paraphaeosphaeria michotii* |
| | *Phoma* sp. |

TABLE 2-continued

Fungal diseases of maize.

| Disease | Causative fungal pathogen |
|---|---|
| | *Septoria zeae* |
| | *Septoria zeicola* |
| | *Septoria zeina* |
| Northern corn leaf | *Setosphaeria turcica* |
| blight | *Exserohilum turcicum* [anamorph] = |
| White blast | *Helminthosporium turcicum* |
| Crown stalk rot | |
| Stripe | |
| Northern corn leaf spot | *Cochliobolus carbonum* |
| *Helminthosporium* ear rot | *Bipolaris zeicola* [anamorph] = |
| (race 1) | *Helminthosporium carbonum* |
| *Penicillium* ear rot | *Penicillium* spp. |
| Blue eye | *Penicillium chrysogenum* |
| Blue mold | *Penicillium expansum* |
| | *Penicillium oxalicum* |
| *Phaeocytostroma* stalk rot and root rot | *Phaeocytostroma ambiguum* = *Phaeocytosporella zeae* |
| *Phaeosphaeria* leaf spot | *Phaeosphaeria maydis* = *Sphaerulina maydis* |
| *Physalospora* ear rot | *Botryosphaeria festucae* = *Physalospora zeicola* |
| *Botryosphaeria* ear rot | *Diplodia frumenti* [anamorph] |
| Purple leaf sheath | Hemiparasitic bacteria and fungi |
| *Pyrenochaeta* stalk rot and root rot | *Phoma terrestris* = *Pyrenochaeta terrestris* |
| *Pythium* root rot | *Pythium* spp. |
| | *Pythium arrhenomanes* |
| | *Pythium graminicola* |
| *Pythium* stalk rot | *Pythium aphanidermatum* = *Pythium butleri* |
| Red kernel disease Ear mold, leaf and seed rot | *Epicoccum nigrum* |
| *Rhizoctonia* ear rot | *Rhizoctonia zeae* |
| Sclerotial rot | *Waitea circinata* [teleomorph] |
| *Rhizoctonia* root rot and stalk rot | *Rhizoctonia solani* |
| | *Rhizoctonia zeae* |
| Root rots, minor | *Alternaria alternata* |
| | *Cercospora sorghi* |
| | *Dictochaeta fertilis* |
| | *Fusarium acuminatum Gibberella acuminata* [teleomorph] |
| | *Fusarium equiseti* |
| | *Gibberella intricans* [teleomorph] |
| | *Fusarium oxysporum* |
| | *Fusarium pallidoroseum* |
| | *Fusarium poae* |
| | *Fusarium roseum* |
| | *Gibberella cyanogena* |
| | *Fusarium sulphureum* [anamorph] |
| | *Microdochium bolleyi* |
| | *Mucor* sp. |
| | *Periconia circinata* |
| | *Phytophthora cactorum* |
| | *Phytophthora drechsleri* |
| | *Phytophthora nicotianae* |
| | *Rhizopus arrhizus* |
| *Rostratum* leaf spot *Helminthosporium* leaf disease, ear and stalk rot | *Setosphaeria rostrata* = *Helminthosporium rostratum* |
| Rust, common corn | *Puccinia sorghi* |
| Rust, southern corn | *Puccinia polysora* |
| Rust, tropical corn | *Physopella pallescens* |
| | *Physopella zeae* = *Angiopsora zeae* |
| *Sclerotium* ear rot | *Sclerotium rolfsii* |
| Southern blight | *Athelia rolfsii* [teleomorph] |
| Seed rot-seedling blight | *Bipolaris sorokiniana* |
| | *Bipolaris zeicola* = *Helminthosporium carbonum* |
| | *Diplodia maydis* |
| | *Exserohilum pedicillatum* |
| | *Exserohilum turcicum* = *Helminthosporium turcicum* |
| | *Fusarium avenaceum* |
| | *Fusarium culmorum* |
| | *Fusarium moniliforme* |
| | *Gibberella zeae* |
| | *Fusarium graminearum* [anamorph] |
| | *Macrophomina phaseolina* |
| | *Penicillium* spp. |
| | *Phomopsis* spp. |
| | *Pythium* spp. |

TABLE 2-continued

Fungal diseases of maize.

| Disease | Causative fungal pathogen |
|---|---|
| | Rhizoctonia solani |
| | Rhizoctonia zeae |
| | Sclerotium rolfsii |
| | Spicaria spp. |
| Selenophoma leaf spot | Selenophoma sp. |
| Sheath rot | Gaeumannomyces graminis |
| Shuck rot | Myrothecium gramineum |
| Silage mold | Monascus purpureus |
| | Monascus ruber |
| Smut, common | Ustilago zeae = Ustilago maydis |
| Smut, false | Ustilaginoidea virens |
| Smut, head | Sphacelotheca reiliana = Sporisorium holci-sorghi |
| Southern corn leaf blight and stalk rot | Cochliobolus heterostrophus<br>Bipolaris maydis [anamorph] = Helminthosporium maydis |
| Southern leaf spot | Stenocarpella macrospora = Diplodia macrospora |
| Stalk rots, minor | Cercospora sorghi |
| | Fusarium episphaeria |
| | Fusarium merismoides |
| | Fusarium oxysporum |
| | Fusarium poae |
| | Fusarium roseum |
| | Fusarium solani |
| | Nectria haematococca [teleomorph] |
| | Fusarium tricinctum |
| | Mariannaea elegans |
| | Mucor spp. |
| | Rhopographus zeae |
| | Spicaria spp. |
| Storage rots | Aspergillus spp. |
| | Penicillium spp. and other fungi |
| Tar spot | Phyllachora maydis |
| Trichoderma ear rot and root rot | Trichoderma viride = Trichoderma lignorum<br>Hypocrea sp. [teleomorph] |
| White ear rot, root and stalk rot | Stenocarpella maydis = Diplodia zeae |
| Yellow leaf blight | Ascochyta ischaemi |
| | Phyllosticta maydis |
| | Mycosphaerella zeae-maydis [teleomorph] |
| Zonate leaf spot | Gloeocercospora sorghi |

In various additional embodiments wherein the crop plant is barley, the fungal pathogen may be any one of the fungal pathogens listed in the right hand column of Table 3, and the disease may be the corresponding disease of wheat listed in the left column of Table 3.

TABLE 3

Fungal diseases of barley.

| Disease | Causative fungal pathogen(s) |
|---|---|
| Anthracnose[1] | Colletotrichum cereale Manns |
| Barley stripe | Pyrenophora graminea = Drechslera graminea |
| Cephalosporium stripe | Hymenula cerealis = Cephalosporium gramineum |
| Common root rot, crown rot and seedling blight | Cochliobolus sativus = Bipolaris sorokiniana<br>Fusarium culmorum<br>Fusarium graminearum<br>Gibberella zeae [teleomorph] |
| Downy mildew | Sclerophthora rayssiae |
| Dwarf bunt | Tilletia controversa |
| Ergot | Claviceps purpurea<br>Sphacelia segetum [anamorph] |
| Eyespot | Pseudocercosporella herpotrichoides<br>Tapesia yallundae [teleomorph] |
| Halo spot | Pseudoseptoria donacis = Selenophoma donacis |

TABLE 3-continued

Fungal diseases of barley.

| Disease | Causative fungal pathogen(s) |
|---|---|
| Kernel blight = black point | Alternaria spp. |
| | Arthrinium arundinis[2] |
| | Apiospora montagnei [teleomorph] |
| | Cochlioboluus sativus |
| | Fusarium spp. |
| Ascochyta leaf spot[1][3] | Ascochyta hordei |
| | Ascochyta graminea |
| | Ascochyta sorghi |
| | Ascochyta tritici |
| Net blotch | Drechslera teres |
| | Pyrenophora teres [teleomorph] |
| Net blotch (spot form) | Drechslera feres f. maculata |
| Powdery mildew | Erysiphe graminis f. sp. hordei = Blumeria graminis |
| | Oidium monilioides [anamorph] |
| Pythium root rot | Pythium spp. |
| | Pythium arrhenomanes |
| | Pythium graminicola |
| | Pythium tardicrescens |
| Rhizoctonia root rot | Rhizoctonia solani |
| | Thanatephorus cucumeris [teleomorph] |
| Crown rust | Puccinia coronata var. hordei |
| Leaf rust | Puccinia hordei |
| Stem rust | Puccinia graminis f. sp. secalis |
| | Puccinia graminis f. sp. tritici |

TABLE 3-continued

Fungal diseases of barley.

| Disease | Causative fungal pathogen(s) |
|---|---|
| Stripe rust = yellow rust | *Puccinia striiformis* f. sp. *hordei* |
| Scab = head blight | *Fusarium* spp. |
| | *Fusarium graminearum* |
| Scald | *Rhynchosporium secalis* |
| *Septoria* speckled leaf blotch | *Septoria passerinii* |
| | *Stagonospora avenae* f. sp. *triticae* |
| Sharp eyespot | *Rhizoctonia cerealis* |
| | *Ceratobasidium cereale* [teleomorph] |
| Covered smut | *Ustilago hordei* |
| False loose smut | *Ustilago nigra* = |
| | *Ustilago avenae* |
| Loose smut | *Ustilago nuda* = |
| | *Ustilago tritici* |
| Gray snow mold = *Typhula* blight | *Typhula incarnata* |
| | *Typhula ishikariensis* |
| Pink snow mold = *Fusarium* patch | *Microdochium nivale* = |
| | *Fusarium nivale* |
| | *Monographella nivalis* [teleomorph] |
| Speckled snow mold | *Typhula idahoensis* |
| Snow rot | *Pythium iwayamae* |
| | *Pythium okanoganense* |
| | *Pythium paddicum* |
| Snow scald = *Sclerotinia* snow mold | *Myriosclerotinia borealis* = |
| | *Sclerotinia borealis* |
| Southern blight | *Sclerotium rolfsii* |
| | *Athelia rolfsii* [teleomorph] |
| Spot blotch | *Cochliobolus sativus* |
| | *Drechslera feres* [anamorph] |
| *Stagonospora* blotch | *Stagonospora avenae* f. sp. *triticae* |
| | *Phaeosphaeria avenaria* f. sp. *triticae* [teleomorph] |
| | *Stagonospora nodorum* = |
| | *Septoria nodorum* |
| | *Phaeosphaeria nodorum* [teleomorph] |
| Take-all | *Gaeumannomyces graminis* var *tritici* |
| Tan spot | *Pyrenophora tritici-repentis* = |
| | *Pyrenophora trichostoma* |
| | *Drechslera tritici-repentis* [anamorph] = |
| | *Helminthosporium tritici-repentis* |
| *Verticillium* wilt[4][5] | *Verticillium dahliae* |
| Wirrega blotch | *Drechslera wirreganensis* |

In various additional embodiments wherein the crop plant is rice, the fungal pathogen may be any one of the fungal pathogens listed in the right hand column of Table 4, and the disease may be the corresponding disease of wheat listed in the left column of Table 4.

TABLE 4

Fungal diseases of rice.

| Disease | Causative fungal pathogen(s) |
|---|---|
| Aggregate sheath spot | *Ceratobasidium oryzae-sativae* |
| | *Rhizoctonia oryzae-sativae* [anamorph] |
| Black kernel | *Curvularia lunata* |
| | *Cochliobolus lunatus* [teleomorph] |
| Blast (leaf, neck [rotten neck], nodal and collar) | *Pyricularia grisea* = |
| | *Pyricularia oryzae* |
| | *Magnaporthe grisea* [teleomorph] |
| Brown spot | *Cochliobolus miyabeanus* |
| | *Bipolaris oryzae* [anamorph] |
| Crown sheath rot | *Gaeumannomyces graminis* |
| Downy mildew | *Sclerophthora macrospora* |
| Eyespot | *Drechslera gigantea* |
| False smut | *Ustilaginoidea virens* |
| Kernel smut | *Tilletia barclayana* = |
| | *Neovossia horrida* |
| Leaf smut | *Entyloma oryzae* |
| Leaf scald | *Microdochium oryzae* = |
| | *Rhynchosporium oryzae* |

TABLE 4-continued

Fungal diseases of rice.

| Disease | Causative fungal pathogen(s) |
|---|---|
| Narrow brown leaf spot | *Cercospora janseana* = |
| | *Cercospora oryzae* |
| | *Sphaerulina oryzina* [teleomorph] |
| Pecky rice (kernel spotting) | Damage by many fungi including |
| | *Cochliobolus miyabeanus* |
| | *Curvularia* spp. |
| | *Fusarium* spp. |
| | *Microdochium oryzae* |
| | *Sarocladium oryzae* |
| | and other fungi. |
| Root rots | *Fusarium* spp. |
| | *Pythium* spp. |
| | *Pythium dissotocum* |
| | *Pythium spinosum* |
| Seedling blight | *Cochliobolus miyabeanus* |
| | *Curvularia* spp. |
| | *Fusarium* spp. |
| | *Rhizoctonia solani* |
| | *Sclerotium rolfsii* |
| | *Athelia rolfsii* [teleomorph] |
| | and other pathogenic fungi. |
| Sheath blight | *Thanatephorus cucumeris* |
| | *Rhizoctonia solani* [anamorph] |
| Sheath rot | *Sarocladium oryzae* = |
| | *Acrocylindrium oryzae* |
| Sheath spot | *Rhizoctonia oryzae* |
| Stackburn (*Alternaria* leaf spot) | *Alternaria padwickii* |
| Stem rot | *Magnaporthe salvinii* |
| | *Sclerotium oryzae* [synanamorph] |
| Water-mold (seed-rot and seedling disease) | *Achlya conspicua* |
| | *Achlya klebsiana* |
| | *Fusarium* spp. |
| | *Pythium* spp. |
| | *Pythium dissotocum* |
| | *Pythium spinosum* |

In various additional embodiments wherein the crop plant is soybean, the fungal pathogen may be any one of the fungal pathogens listed in the right hand column of Table 5, and the disease may be the corresponding disease of wheat listed in the left column of Table 5.

TABLE 5

Fungal diseases of soybean.

| Disease | Causative fungal pathogen(s) |
|---|---|
| *Alternaria* leaf spot | *Alternaria* spp. |
| Anthracnose | *Colletotrichum truncatum* |
| | *Colletotrichum dematium* f. *truncatum* |
| | *Glomerella glycines* |
| | *Colletotrichum destructivum* [anamorph] |
| Black leaf blight | *Arkoola nigra* |
| Black root rot | *Thielaviopsis basicola* |
| | *Chalara elegans* [synanamorph] |
| Brown spot | *Septoria glycines* |
| | *Mycosphaerella usoenskajae* [teleomorph] |
| Brown stem rot | *Phialophora gregata* = |
| | *Cephalosporium gregatum* |
| Charcoal rot | *Macrophomina phaseolina* |
| *Choanephora* leaf blight | *Choanephora infundibulifera* |
| | *Choanephora trispora* |
| Damping-off | *Rhizoctonia solani* |
| | *Thanatephorus cucumeris* [teleomorph] |
| | *Pythium aphanidermatum* |
| | *Pythium debaryanum* |
| | *Pythium irregulare* |
| | *Pythium myriotylum* |
| | *Pythium ultimum* |

TABLE 5-continued

Fungal diseases of soybean.

| Disease | Causative fungal pathogen(s) |
|---|---|
| Downy mildew | Peronospora manshurica |
| Drechslera blight | Drechslera glycines |
| Frogeye leaf spot | Cercospora sojina |
| Fusarium root rot | Fusarium spp. |
| Leptosphaerulina leaf spot | Leptosphaerulina trifolii |
| Mycoleptodiscus root rot | Mycoleptodiscus terrestris |
| Neocosmospora stem rot | Neocosmospora vasinfecta Acremonium spp. [anamorph] |
| Phomopsis seed decay | Phomopsis spp. |
| Phytophthora root and stem rot | Phytophthora sojae |
| Phyllosticta leaf spot | Phyllosticta sojaecola |
| Phymatotrichum root rot = cotton root rot | Phymatotrichopsis omnivora = Phymatotrichum omnivorum |
| Pod and stem blight | Diaporthe phaseolorum Phomopsis sojae [anamorph] |
| Powdery mildew | Microsphaera diffusa |
| Purple seed stain | Cercospora kikuchii |
| Pyrenochaeta leaf spot | Pyrenochaeta glycines |
| Pythium rot | Pythium aphanidermatum Pythium debaryanum Pythium irregulare Pythium myriotylum Pythium ultimum |
| Red crown rot | Cylindrocladium crotalariae Calonectria crotalariae [teleomorph] |
| Red leaf blotch = Dactuliophora leaf spot | Dactuliochaeta glycines = Pyrenochaeta glycines Dactuliophora glycines [synanamorph] |
| Rhizoctonia aerial blight | Rhizoctonia solani Thanatephorus cucumeris [teleomorph] |
| Rhizoctonia root and stem rot | Rhizoctonia solani |
| Rust | Phakopsora pachyrhizi |
| Scab | Spaceloma glycines |
| Sclerotinia stem rot | Sclerotinia sclerotiorum |
| Southern blight (damping-off and stem rot) = Sclerotium blight | Sclerotium rolfsii Athelia rolfsii [teleomorph] |
| Stem canker | Diaporthe phaseolorum Diaporthe phaseolorum var. caulivora Phomopsis phaseoli [anamorph] |
| Stemphylium leaf blight | Stemphylium botryosum Pleospora tarda [teleomorph] |
| Sudden death syndrome | Fusarium solani f. sp. glycines |
| Target spot | Corynespora cassiicola |
| Yeast spot | Nematospora coryli |

In various additional embodiments wherein the crop plant is potato, the fungal pathogen may be any one of the fungal pathogens listed in the right hand column of Table 6, and the disease may be the corresponding disease of wheat listed in the left column of Table 6.

TABLE 6

Fungal diseases of potato.

| Disease | Causative fungal pathogen(s) |
|---|---|
| Black dot | Colletotrichum coccodes = Colletotrichum atramentarium |
| Brown spot and Black pit | Alternaria alternata = Alternaria tenuis |
| Cercospora leaf blotch | Mycovellosiella concors = Cercospora concors Cercospora solani Cercospora solani-tuberosi |
| Charcoal rot | Macrophomina phaseolina = Sclerotium bataticola |

TABLE 6-continued

Fungal diseases of potato.

| Disease | Causative fungal pathogen(s) |
|---|---|
| Choanephora blight | Choanephora cucurbitarum |
| Common rust | Puccinia pittieriana |
| Deforming rust | Aecidium cantensis |
| Early blight | Alternaria solani |
| Fusarium dry rot | Fusarium spp. Gibberella pulicaris = Fusarium solani Other Fusarium spp. include: Fusarium avenaceum Fusarium oxysporum Fusarium culmorum Less common Fusarium spp. include: Fusarium acuminatum Fusarium equiseti Fusarium crookwellense |
| Fusarium wilt | Fusarium spp. Fusarium avenaceum Fusarium oxysporum Fusarium solani f. sp. eumartii |
| Gangrene | Phoma solanicola f. foveata Phoma foveata = Phoma exigua var. foveata = Phoma exigua f. sp. foveata Phoma exigua var. exigua |
| Gray mold | Botrytis cinerea Botryotinia fuckeliana [teleomorph] |
| Late blight | Phytophthora infestans |
| Leak | Pythium spp. Pythium ultimum var. ultimum = Pythium debaryanum Pythium aphanidermatum Pythium deliense |
| Phoma leaf spot | Phoma andigena var. andina |
| Pink rot | Phytophthora spp. Phytophthora cryptogea Phytophthora drechsleri Phytophthora erythroseptica Phytophthora megasperma Phytophthora nicotianae var. parasitica |
| Powdery mildew | Erysiphe cichoracearum |
| Powdery scab | Spongospora subterranea f. sp. subterranea |
| Rhizoctonia canker and black scurf | Rhizoctonia solani Thanatephorus cucumeris [teleomorph] |
| Rosellinia black rot | Rosellinia sp. Dematophora sp. [anamorph] |
| Septoria leaf spot | Septoria lycopersici var. malagutii |
| Silver scurf | Helminthosporium solani |
| Skin spot | Polyscytalum pustulans |
| Stem rot (southern blight) | Sclerotium rolfsii Athelia rolfsii [teleomorph] |
| Thecaphora smut | Angiosorus solani = Thecaphora solani |
| Ulocladium blight | Ulocladium atrum |
| Verticillium wilt | Verticillium albo-atrum Verticillium dahliae |
| Wart | Synchytrium endobioticum |
| White mold | Sclerotinia sclerotiorum |

Various alternative embodiments and examples of the invention are described herein. These embodiments and examples are illustrative, and not limiting.

Various implementations and examples of the combinations are described herein. These implementations and examples are illustrative, and not limiting.

EXAMPLES

Example 1

Greenhouse Stem Rust Evaluation Study

The efficacy of Civitas™ alone or in combination with Harmonizer™ in controlling infection of wheat (*Triticum aestivum* 'Norin43') by *Puccinia graminis* f. sp. *tritici*

("Pgt") was tested under greenhouse conditions. Briefly, each treatment consisted of four pots containing four plants. Plants were planted on March 2nd. Civitas™, Harmonizer™, and combinations thereof were applied to test plants, by foliar application, on March 10th, seven days before inoculation (DBI) on March 17th as indicated in Table 7. The average severity of infection, in terms of % leaf area infected, was evaluated 12 days after inoculation on March 29th.

TABLE 7

Results of greenhouse stem rust evaluation study.
Greenhouse Stem Rust Evaluation Study
Pathogen: *Puccinia graminis* f.sp. *tritici*

| Treat ID | Method | Carrier (gal/A) | Timing | Civitas (oz/acre) | Harmonizer (oz/acre) | Treated | % Leaf Area (severity) Avg. Sev | SD % | Infection Type Avg. IT | SD % |
|---|---|---|---|---|---|---|---|---|---|---|
| 1 | Foliar | 20 | 7DBI | 160 | 0 | 3/10 | 20.00 | 7.07 | 2.25 | 0.50 |
| 2 | Foliar | 20 | 7DBI | 320 | 0 | 3/10 | 15.00 | 4.08 | 2.25 | 0.50 |
| 3 | Foliar | 20 | 7DBI | 0 | 10 | 3/10 | 26.25 | 6.29 | 3.50 | 0.58 |
| 4 | Foliar | 20 | 7DBI | 0 | 20 | 3/10 | 25.00 | 4.08 | 3.25 | 0.50 |
| 5 | Foliar | 20 | 7DBI | 40 | 2.5 | 3/10 | 16.00 | 2.71 | 2.50 | 0.58 |
| 6 | Foliar | 20 | 7DBI | 160 | 10 | 3/10 | 11.25 | 4.79 | 1.75 | 0.50 |
| 7 | Foliar | 20 | 7DBI | 320 | 20 | 3/10 | 8.75 | 4.79 | 1.25 | 0.50 |
| 8 | Drench | 400 | 7DBI | 160 | 0 | 3/10 | 17.50 | 6.45 | 2.25 | 0.50 |
| 9 | Drench | 400 | 7DBI | 320 | 0 | 3/10 | 16.25 | 2.50 | 2.25 | 0.50 |
| 10 | Drench | 400 | 7DBI | 0 | 10 | 3/10 | 26.25 | 4.79 | 3.25 | 0.96 |
| 11 | Drench | 400 | 7DBI | 0 | 20 | 3/10 | 25.00 | 7.07 | 3.25 | 0.50 |
| 12 | Drench | 400 | 7DBI | 40 | 2.5 | 3/10 | 17.50 | 2.89 | 2.00 | 0.82 |
| 13 | Drench | 400 | 7DBI | 160 | 10 | 3/10 | 10.00 | 4.08 | 1.50 | 0.58 |
| 14 | Drench | 400 | 7DBI | 320 | 20 | 3/10 | 7.50 | 2.89 | 1.25 | 0.50 |
| 15 | Control | 20 | N/A | 0 | 0 | 3/10 | 27.50 | 6.45 | 3.75 | 0.50 |

Example 2

Wheat Stem Rust Study

The efficacy of Civitas™ alone or in combination with Harmonizer™, Folicur™, or Quilt™ in controlling infection of wheat (*Triticum aestivum* 'Norin43') by Pgt was tested between May and July. A field was treated with Roundup™ on May 9th and cultivated twice before planting. Plots were planted on May 28 using a seeding rate of 1.25 bu/A, and were 15 ft long by 5 ft wide with 7 rows. Due to flooding in the field shortly after planting, plots lengths were reduced to 7 ft long prior to cutting of the alleys. Plots consisting of a highly susceptible rust spreader mixture were alternated with the experimental units.

The experimental design was a randomized complete block with five replicates. Puma™ (0.4 pt/A) and Bronate Advanced™ (0.8 pt/A) were applied on June 10th to control weeds. On July 14th, urediniospores of Pgt were collected from nearby trap plots and applied to the spreader rows in a 0.1% water agar suspension using a hand-powered backpack sprayer. On July 20th, fungicide treatments were applied with a $CO_2$-powered backpack sprayer in a carrier volume of 20 gal/A using XR8002 flat fan nozzles and an application pressure of 40 PSI. The plants in each plot were at Feekes 10.51 (early anthesis). At 48 hr after fungicide application, the experimental plots were inoculated as previously described with Pgt and misted at night for 7 days (3 min on per each 30 min) to facilitate infection and disease development. One treatment received a second application 7 days later (Treatment 5, see Table 8 below). Plots were rated for stem rust severity at 14 d after inoculation by visually estimating the percentage of stem area covered with pustules for 50 plants per plot (5 randomly chosen locations of 10 plants each). Plots were harvested with a small plot combine and yield was determined. Data were analyzed using an ANOVA and pair-wise comparisons were performed using Tukey's HSD (P=0.05).

TABLE 8

Results of Wheat Stem Rust Study

| Trt No. | App Rate (oz/acre) | Upper Stem Severity (% infected area) | Average Stem Severity (% infected area) | Yield (g/plot) | Yield (% of Control) |
|---|---|---|---|---|---|
| 1 | Non-inoculated Control | 37.50 | 39.17 | 67.325 | 6 |
| 2 | Inoculated Control | 38.00 | 39.00 | 63.4 | 0 |
| 3 | Civitas (160) | 27.25 | 29.33 | 80.05 | 26 |
| 4 | Civitas (320) | 25.75 | 28.50 | 63.475 | 0 |
| 5 | Civitas + Harmonizer (160 + 10) (1 app) | 26.25 | 29.50 | 71.65 | 13 |
| 6 | Civitas + Harmonizer (160 + 10) (2 apps) | 27.00 | 29.75 | 96.225 | 52 |
| 7 | Civitas + Harmonizer | 25.50 | 30.00 | 78.525 | 24 |

TABLE 8-continued

Results of Wheat Stem Rust Study

| Trt No. | App Rate (oz/acre) | Upper Stem Severity (% infected area) | Average Stem Severity (% infected area) | Yield (g/plot) | Yield (% of Control) |
|---|---|---|---|---|---|
| | (320 + 20) | | | | |
| 8 | Folicur (4) | 25.00 | 29.08 | 142.175 | 124 |
| 9 | Quilt (14) | 14.50 | 19.17 | 161.75 | 155 |
| 10 | Civitas + 1/2 Folicur (160 + 2) | 20.75 | 24.75 | 169.75 | 168 |
| 11 | Civitas + Harmonizer + 1/2 Folicur (80 + 5 + 2) | 19.25 | 24.25 | 176.2 | 178 |
| 12 | Civitas + Harmonizer + 1/2 Folicur (160 + 10 + 2) | 16.75 | 22.17 | 203.5 | 221 |
| 13 | Civitas + Harmonizer + 1/2 Folicur (320 + 20 + 2) | 11.00 | 16.92 | 185.175 | 192 |
| 14 | Civitas + Harmonizer + 1/2 Quilt (80 + 5 + 7) | 19.50 | 25.00 | 162.075 | 156 |

Example 3

Greenhouse Spot Blotch Evaluation Study

The efficacy of Civitas™/Harmonizer™, alone or in combination with Folicur™ in controlling infection of wheat (*Triticum aestivum* 'Baart') by *Bipolaris sorokiniana* was tested under greenhouse conditions. Briefly, each treatment consisted of three pots (4" by 4") containing three plants each. Plants were planted on March 1st. Civitas™/Harmonizer™, Folicur™, and combinations thereof were applied to test plants, by foliar application on March 8 (seven DBI), by soil drench on March 8th (7 DBI), or by foliar application on March 14th (1 DBI), as indicated in Table 9 (rates of Civitas, Harmonizer, and Folicur are expressed in oz/acre). For foliar application, the treatments were applied in 0.2 mL per pot, which is the equivalent of 20 gal/A. For soil drench, treatments were applied in 3.8 mL, which is the equivalent of 400 gal/A. Plants were innoculated on March 15th. The average severity of infection, in terms of % leaf area infected, was evaluated 14 days after inoculation on March 29th.

Figure 2:
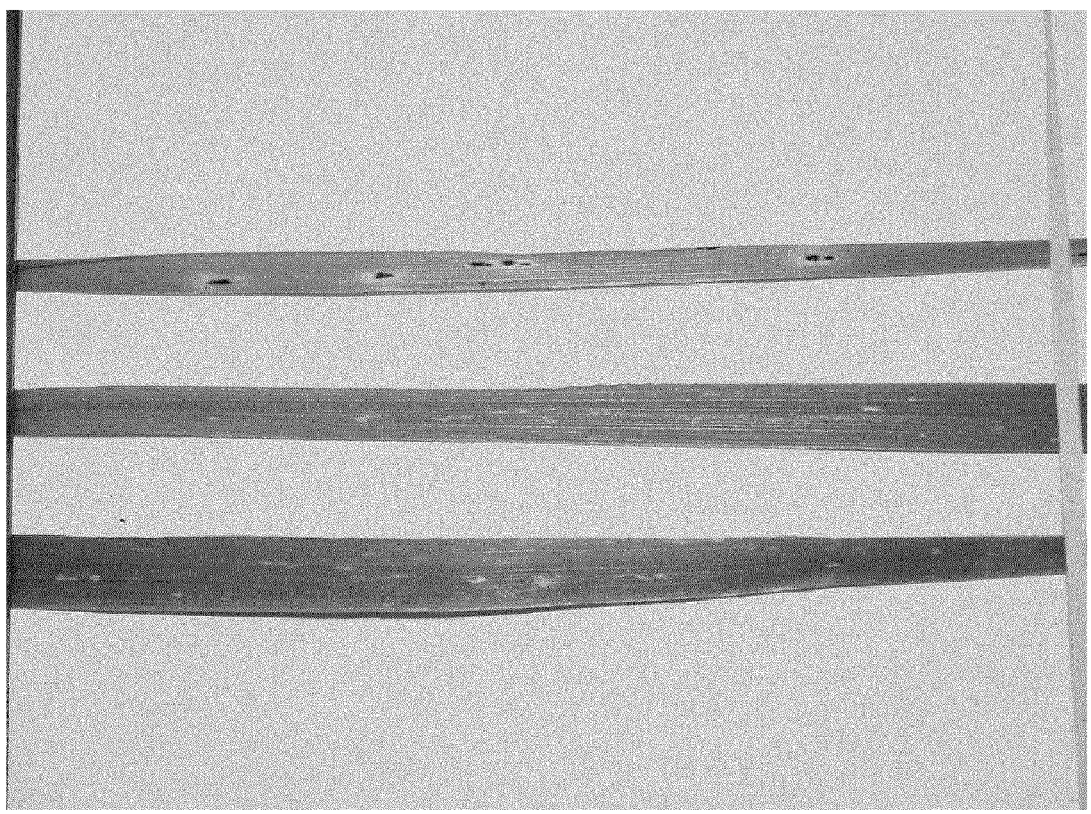
FIG. 2 is an image of a leaf blade of a wheat plant inoculated with *Bipolaris sorokiniana* following foliar application of a fungicidal composition comprising Civitas™. Harmonizer™, and Folicur™ seven days before inoculation.
Figure 3:
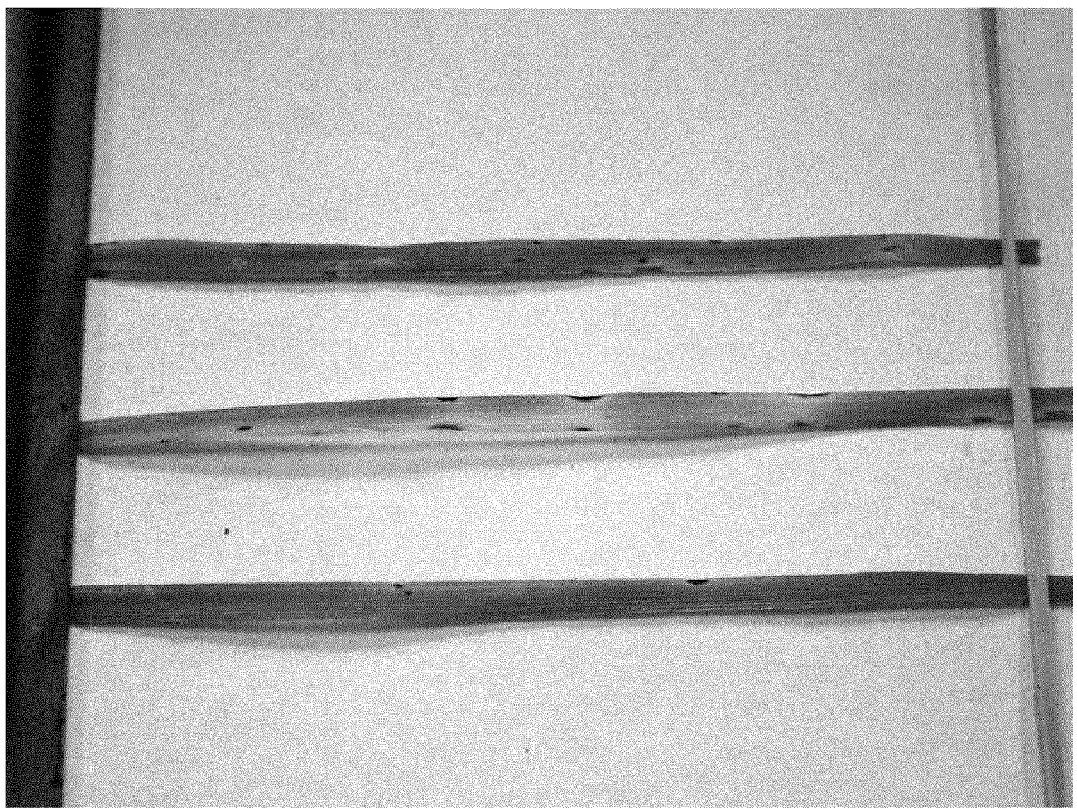
FIG. 3 is an image of a leaf blade of a wheat plant inoculated with *Bipolaris sorokiniana* following soil drench application of a fungicidal composition comprising Civitas™ and Harmonizer™ seven days before inoculation.

Images of the untreated, inoculated control are presented in FIG. 1. Note the number of pustules (dark spots), near lack of chlorosis (light halos surrounding dark spots), and large pustule size. FIG. 2 shows leaves of inoculated plants that were treated with Civitas™/Harmonizer™ (160+10 oz/acre) and Folicur (2 oz/acre) by foliar application 7 DBI. Note the near lack of symptoms, small pustule size, and chlorotic halos. FIG. 3 shows leaves of inoculated plants that were treated with Civitas™/Harmonizer™ (320+20 oz/acre) by soil drench application 7 DBI. Note the near lack of symptoms, chlorotic halos, and reduced pustule size.

TABLE 9

Results of Greenhouse Spot Blotch Evaluation Study
Greenhouse Spot Blotch Evaluation Study
Pathogen: *Bipolaris sorokiniana*

| Treat ID | Method | Carrier (gal/A) | Timing | Civitas | Harmonizer | Folicur | Treated | % Leaf Area (severity) Rep 1 | Rep 2 | Rep 3 | 0-4, R to Susceptible Infection Type Rep 1 | Rep 2 | Rep 3 | Avg. Sev | IT |
|---|---|---|---|---|---|---|---|---|---|---|---|---|---|---|---|
| 01 | Foliar | 0 | 7DBI | 160 | 10 | 0 | 3/8 | 5 | 5 | 5 | 2 | 1 | 1 | 5.0 | 1.3 |
| 02 | Foliar | 0 | 7DBI | 320 | 20 | 0 | 3/8 | 0 | 10 | 3 | 0 | 2 | 1 | 4.3 | 1.0 |
| 03 | Drench | 00 | 7DBI | 160 | 10 | 0 | 3/8 | 5 | 5 | 0 | 1 | 1 | 0 | 3.3 | 0.7 |
| 04 | Drench | 00 | 7DBI | 320 | 20 | 0 | 3/8 | 0 | 0 | 0 | 0 | 0 | 0 | 0.0 | 0.0 |
| 05 | Foliar | 0 | 1DBI | 160 | 10 | 0 | 3/14 | 10 | 10 | 10 | 3 | 3 | 1 | 10.0 | 2.3 |
| 06 | Foliar | 0 | 1DBI | 0 | 0 | 2 | 3/14 | 5 | 5 | 0 | 1 | 2 | 0 | 3.3 | 1.0 |
| 07 | Foliar | 0 | 1DBI | 0 | 0 | 4 | 3/14 | 5 | 0 | 2 | 1 | 0 | 1 | 2.3 | 0.7 |
| 08 | Foliar | 0 | 1DBI | 160 | 10 | 2 | 3/14 | 5 | 0 | 0 | 1 | 0 | 0 | 1.7 | 0.3 |
| Control | N/A | /A | /A | 0 | 0 | 0 | N/A | 15 | 20 | 15 | 4 | 4 | 4 | 16.7 | 4.0 |

Example 4

Greenhouse Leaf Rust Evaluation Study

The efficacy of Civitas™/Harmonizer™, alone or in combination with Folicur™ in controlling infection of wheat (*Triticum aestivum* 'Bawl') by *Puccinia triticina* was tested under greenhouse conditions. Briefly, each treatment consisted of three pots (4" by 4") containing three plants each. Plants were planted on March 1st. Civitas™/Harmonizer™, Folicur™, and combinations thereof were applied to test plants, by foliar application on March 8 (seven DBI), by soil drench on March 8th (7 DBI), or by foliar application on March 14th (1 DBI), as indicated in Table 10 (rates of Civitas, Harmonizer, and Folicur are expressed in oz/acre). For foliar application, the treatments were applied in 0.2 mL per pot, which is the equivalent of 20 gal/A. For soil drench, treatments were applied in 3.8 mL, which is the equivalent of 400 gal/A. Plants were inoculated on March 15th. The average severity of infection, in terms of % leaf area infected, was evaluated 14 days after inoculation on March 29th.

TABLE 10

Results of Greenhouse Leaf Rust Evaluation Study
Greenhouse Leaf Rust Evaluation Study
Pathogen: *Puccinia triticina*

| Treat ID | Method | Carrier (gal/A) | Timing | Civitas | Harmonizer | Folicur | Treated | % Leaf Area (severity) Rep 1 | Rep 2 | Rep 3 | 0-4, R to Susceptible Infection Type Rep 1 | Rep 2 | Rep 3 | Avg. Sev | Avg. IT |
|---|---|---|---|---|---|---|---|---|---|---|---|---|---|---|---|
| 1 | Foliar | 20 | 7DBI | 160 | 10 | 0 | 3/8 | 15 | 20 | 15 | 2 | 1 | 1 | 16.7 | 1.3 |
| 2 | Foliar | 20 | 7DBI | 320 | 20 | 0 | 3/8 | 15 | 15 | 10 | 1 | 1 | 2 | 13.3 | 1.3 |
| 3 | Drench | 400 | 7DBI | 160 | 10 | 0 | 3/8 | 20 | 20 | 25 | 2 | 2 | 2 | 21.7 | 2.0 |
| 4 | Drench | 400 | 7DBI | 320 | 20 | 0 | 3/8 | 20 | 15 | 20 | 2 | 2 | 1 | 18.3 | 1.7 |
| 5 | Foliar | 20 | 1DBI | 160 | 10 | 0 | 3/14 | 15 | 15 | 15 | 1 | 1 | 2 | 15.0 | 1.3 |
| 6 | Foliar | 20 | 1DBI | 0 | 0 | 2 | 3/14 | 5 | 5 | 5 | 1 | 1 | 1 | 5.0 | 1.0 |
| 7 | Foliar | 20 | 1DBI | 0 | 0 | 4 | 3/14 | 0 | 0 | 0 | 0 | 0 | 0 | 0.0 | 0.0 |
| 8 | Foliar | 20 | 1DBI | 160 | 10 | 2 | 3/14 | 0 | 5 | 5 | 0 | 1 | 1 | 3.3 | 0.7 |
| Control | Control | N/A | N/A | 0 | 0 | 0 | N/A | 25 | 30 | 30 | 3 | 3 | 3 | 28.3 | 3.0 |

Figure 4:
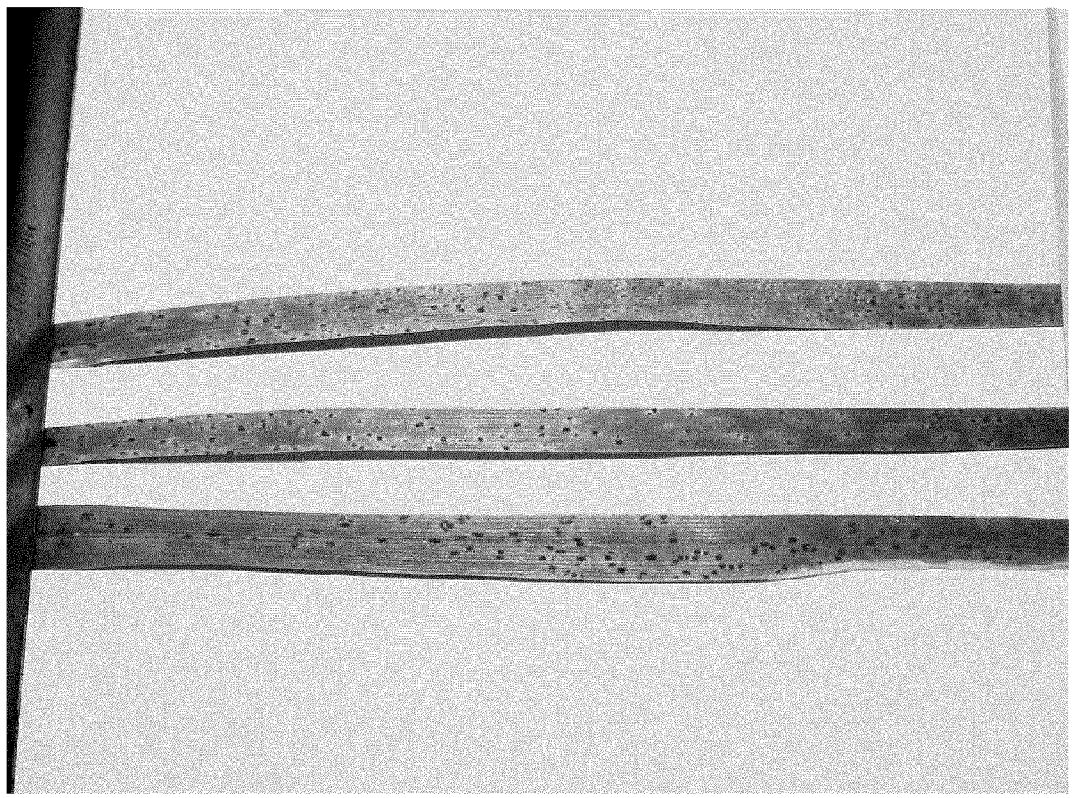
FIG. 4 is an image of a leaf blade of a wheat plant displaying splotch blot disease after inoculation with *Puccinia triticina* without prior treatment with a fungicidal composition.
Figure 5:
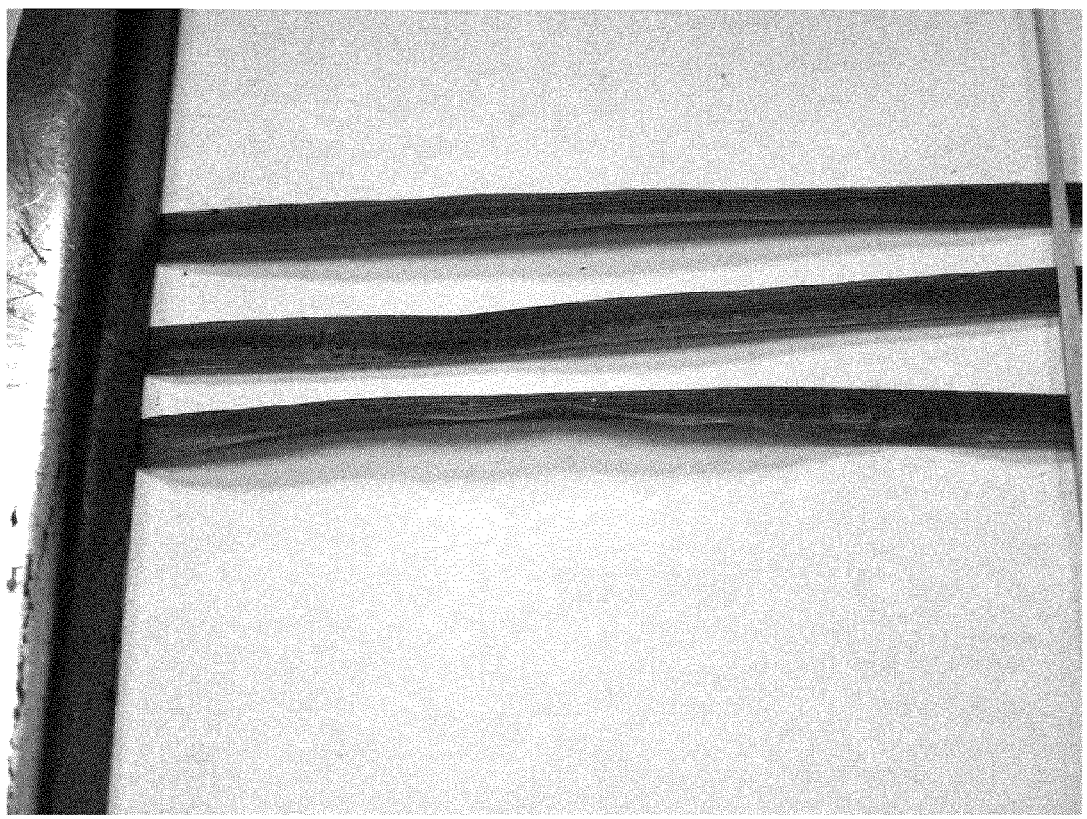
FIG. 5 is an image of a leaf blade of a wheat plant inoculated with *Puccinia triticina* following foliar application of a fungicidal composition comprising Civitas™. Harmonizer™, and Folicur™ seven days before inoculation.
Figure 6:
FIG. 6 is an image of a leaf blade of a wheat plant inoculated with *Puccinia triticina* following soil drench application of a fungicidal composition comprising Civitas™ and Harmonizer™ seven days before inoculation.

Images of the untreated, inoculated control are presented in FIG. 4. Note the large number of pustules (dark spots), near lack of chlorosis, and large pustule size. FIG. 5 shows leaves of inoculated plants that were treated with Civitas™/Harmonizer™ (160+10 oz/acre) and Folicur (2 oz/acre) by foliar application 7 DBI. Note the near lack of pustules, somewhat restricted size, and small chlorotic halos indicative of a resistance response. FIG. 6 shows leaves of inoculated plants that were treated with Civitas™/Harmonizer™ (320+20 gal/A) by soil drench application 7 DBI. Note the lack of pustules, restricted size, and large chlorotic halos indicative of a resistance response.

Example 5

Greenhouse *Fusarium* Head Blight Evaluation Study

The efficacy of Civitas™, Harmonizer™, and Folicur™ alone or in combination, in controlling infection of wheat (*Triticum aestivum* 'Sonalika') by *Fusarium graminearum* was tested under greenhouse conditions. Briefly, each treatment consisted of four pots (4" by 4") containing nine plants each. Plants were planted on March 2nd. Civitas™, Harmonizer™, Folicur™, and combinations thereof were applied to test plants, by foliar application or by soil drench on March 10 (39 DBI), or 35 DBI by foliar application on March 16th, as indicated in Table 11 (rates of Civitas, Harmonizer, and Folicur are expressed in oz/acre). For foliar application, the treatments were applied in 0.2 mL per pot, which is the equivalent of 20 gal/A. For soil drench, treatments were applied in 3.8 mL, which is the equivalent of 400 gal/A. Plants were innoculated on April 18th. The average severity of infection was evaluated 14 days after inoculation on May 2nd.

TABLE 11

Results of Greenhouse Spot Blotch Evaluation Study
Greenhouse Spot Blotch Evaluation Study
Pathogen: *Bipolaris sorokiniana*

| Treat ID | Method | Carrier (gal/A) | Timing | Civitas | Harmonizer | Folicur | Treated | % Leaf Area (severity) Rep 1 | Rep 2 | Rep 3 | 0-4, R to Susceptible Infection Type Rep 1 | Rep 2 | Rep 3 | Avg. Sev | Avg. IT |
|---|---|---|---|---|---|---|---|---|---|---|---|---|---|---|---|
| 01 | Foliar | 20 | 7DBI | 160 | 10 | 0 | 3/8 | 5 | 5 | 5 | 2 | 1 | 1 | 5.0 | 1.3 |
| 02 | Foliar | 20 | 7DBI | 320 | 20 | 0 | 3/8 | 0 | 10 | 3 | 0 | 2 | 1 | 4.3 | 1.0 |
| 03 | Drench | 400 | 7DBI | 160 | 10 | 0 | 3/8 | 5 | 5 | 0 | 1 | 1 | 0 | 3.3 | 0.7 |
| 04 | Drench | 400 | 7DBI | 320 | 20 | 0 | 3/8 | 0 | 0 | 0 | 0 | 0 | 0 | 0.0 | 0.0 |
| 05 | Foliar | 20 | 1DBI | 160 | 10 | 0 | 3/14 | 10 | 10 | 10 | 3 | 3 | 1 | 10.0 | 2.3 |
| 06 | Foliar | 20 | 1DBI | 0 | 0 | 2 | 3/14 | 5 | 5 | 0 | 1 | 2 | 0 | 3.3 | 1.0 |
| 07 | Foliar | 20 | 1DBI | 0 | 0 | 4 | 3/14 | 5 | 0 | 2 | 1 | 0 | 1 | 2.3 | 0.7 |
| 08 | Foliar | 20 | 1DBI | 160 | 10 | 2 | 3/14 | 5 | 0 | 0 | 1 | 0 | 0 | 1.7 | 0.3 |
| Control | N/A | N/A | N/A | 0 | 0 | 0 | N/A | 15 | 20 | 15 | 4 | 4 | 4 | 16.7 | 4.0 |

Example 6

Soybean Rust Study in Georgia

The efficacy of Civitas™, Harmonizer™, and Headline™ (Pyraclostrobin, BASF), and Domark®230 ME (Tetraconazole, Valent), alone or in combination, in controlling infection of soybean (*Glycine max*) by *Phakospora pachyrhizi* was tested in the field in Georgia. Civitas was tested at 640 oz/a (5 gal/a) and 320 oz/a (2.5 gal/a), with and without Harmonizer. Two conventional chemical fungicides that are labelled for soybean rust, Headline® and Domark®230 ME were used alone, as well as tank mix partners with Civitas. The total spray volume is 15 gal/a, significantly lower than the spray volume for turf applications (50-100 gal/a). Accordingly, the concentrations of the Civitas solution were much higher than in turf application (16% to 33% in this study). The treatments are listed in Table 12. The results of this study are provided in Table 13. Civitas showed significant control of *Phakospora pachyrhizi* on soybean. The incidence and severity were equal to or exceeded control by the conventional fungicides. The combination of the conventional fungicides with Civitas alone or Civitas/Harmonzier provided better efficacy than the conventional fungicides used alone.

TABLE 12

List of treatments of soybean plants prior to innoculation

| rt No. | Treatment | Form Conc. GA/L (%) | Form Type | Rate (oz/ acre) | Appl Code | Application Description | Amount Production to Measure |
|---|---|---|---|---|---|---|---|
| 1 | Headline | 250 | EC | 6 | AB | R2-R3 | 9.375 ml/mx |
| 2 | Headline | 250 | EC | 4 | AB | R2-R3 | 6.25 ml/mc |
| 3 | Headline | 250 | EC | 4 | AB | R2-R3 | 6.25 ml/mx |
| | Civitas | (1) | L | 640 | AB | R2-R3 | 1000.0 ml/mx |
| 4 | Headline | 250 | EC | 4 | AB | R2-R3 | 6.25 ml/mx |
| | Civitas | (1) | L | 320 | AB | R2-R3 | 500.0 ml/mx |
| | Harmonizer | (1) | L | 20 | AB | R2-R3 | 31.25 ml/mx |
| 5 | Headline | 250 | EC | 4 | AB | R2-R3 | 6.25 ml/mx |
| | Civitas | (1) | L | 640 | AB | R2-R3 | 1000.0 ml/mx |
| | Harmonizer | (1) | L | 40 | AB | R2-R3 | 62.25 ml/mx |
| 6 | Civitas | (1) | L | 640 | AB | R2-R3 | 1000.0 ml/mx |
| 7 | Civitas | (1) | L | 640 | AB | R2-R3 | 1000.0 ml/mx |
| | Harmonizer | (1) | L | 40 | AB | R2-R3 | 62.25 ml/mx |
| 8 | Headline | 250 | EC | 6 | AB | R2-R3 | 9.375 ml/mx |
| | Civitas | (1) | L | 320 | AB | R2-R3 | 500. mlmx |
| | Harmonizer | (1) | L | 20 | AB | R2-R3 | 31.25 ml/mx |
| 9 | Domark 230 ME | 230 | ME | 4 | AB | R2-R3 | 6.25 ml/mx |
| 10 | Domark 230 ME | 230 | ME | 2 | AB | R2-R3 | 3.12 ml/mx |
| 11 | Domark 230 ME | 230 | ME | 2 | AB | R2-R3 | 3.125 ml/mx |
| | Civitas | (1) | L | 640 | AB | R2-R3 | 1000.0 ml/mx |
| 12 | Domark 230 ME | 230 | ME | 2 | AB | R2-R3 | 3.125 ml/mx |
| | Civitas | (1) | L | 320 | AB | R2-R3 | 500.0 ml/mx |
| | Harmonizer | (1) | L | 20 | AB | R2-R3 | 31.25 ml/mx |
| 13 | Domark 230 ME | 230 | ME | 2 | AB | R2-R3 | 3.125 ml/mx |
| | Civitas | (1) | L | 640 | AB | R2-R3 | 1000.0 ml/mx |
| | Harmonizer | (1) | L | 40 | AB | R2-R3 | 62.5 ml/mx |
| 14 | Civitas | (1) | L | 640 | AB | R2-R3 | 1000.0 ml/mx |
| 15 | Civitas | (1) | L | 640 | AB | R2-R3 | 1000.0 ml/mx |
| | Harmonizer | (1) | | 40 | AB | R2-R3 | 62.5 ml/mx |
| 16 | Domark 230 ME | 230 | ME | 4 | AB | R2-R3 | 6.25 ml/mx |
| | Civitas | (1) | L | 320 | AB | R2-R3 | 500.0 ml/mx |
| | Harmonizer | (1) | L | 20 | AB | R2-R3 | 31.25 ml/mx |

TABLE 13

Results of Soybean Rust Study.

| | Pest Type | D Disease | D Disease | D Disease | D Disease | D Disease |
|---|---|---|---|---|---|---|
| | Pest Name | SBR | SBR | SBR | SBR | SBR |
| | Crop Name | Soy Bean | Soy Bean | Soy Bean | Soy Bean | Soy Bean |
| | Rating Date | Oct. 21 | Oct. 21 | Oct. 21 | Oct. 21 | Nov. 17 |
| | Rating Date Type | Defoliation | Incidence | Leaf Area | Severity | Yield |
| | Rating Unit | % | | % | Scale | Lb |
| | Sample Size Unit | | | | | Plot |
| | Days After First/ Last Applic. | 71/42 | 71/42 | 71/42 | 71/42 | 98/69 |
| Trt No. | Treatment Name | 1 | 2 | 3 | 4 | 5 |
| 1 | Headline | 82.5 b-e | 32.5 b-e | 1.258 a | 0.58 a | 23.755 a |
| 2 | Headline | 76.3 e | 62.5 ab | 3.423 a | 1.45 ab | 24.070 a |
| 3 | Headline Civitas | 83.8 b-e | 30.0 b-e | 4.963 a | 1.20 abc | 19.660 cd |
| 4 | Headline Civitas Harmonizer | 81.3 b-e | 32.5 b-e | 0.378 a | 0.38 bcd | 19.575 cd |
| 5 | Headline Civitas Harmonizer | 83.8 b-e | 20.0 cde | 0.213 a | 0.30 cd | 18.868 cde |
| 6 | Civitas | 83.8 b-e | 27.5 b-e | 0.218 a | 0.30 cd | 18.868 cde |
| 7 | Civitas Harmonizer | 88.8 ab | 50.0 a-d | 1.405 a | 0.85 bcd | 18.325 def |
| 8 | Headline Civitas Harmonizer | 80.8 cde | 30.0 b-e | 0.275 a | 0.33 cd | 23.370 ab |
| 9 | Domark 230 ME | 77.5 de | 30.0 b-e | 0.265 a | 0.30 cd | 23.370 ab |

TABLE 13-continued Results of Soybean Rust Study.

| | | | | | | |
|---|---|---|---|---|---|---|
| 10 | Domark 230 ME | 87.5 abc | 20.0 cde | 0.158 a | 0.20 cd | 19.688 cd |
| 11 | Domark 230 ME Civitas | 87.5 abc | 5.0 e | 0.015 a | 0.05 d | 19.008 cde |
| 12 | Domark 230 ME Civitas Harmonizer | 85.0 a-d | 17.5 de | 0.105 a | 0.18 cd | 21.030 bc |
| 13 | Domark 230 ME Civitas Harmonizer | 92.2 a | 12.5 de | 0.073 a | 0.13 cd | 16.560 ef |
| 14 | Civitas | 86.3 abc | 57.5 abc | 1.460 a | 0.90 bcd | 18.925 cde |
| 15 | Civitas Harmonizer | 87.2 abc | 37.5 b-e | 1.880 a | 0.75 bcd | 16.143 f |
| 16 | Domark 230 ME Civitas Harmonizer | 88.8 ab | 30.0 b-e | 0.375 a | 0.35 cd | 18.385 def |
| 17 | Untreated Control | 82.5 b-e | 82.5 a | 6.233 a | 2.20 a | 23.210 ab |
| | LSD (P = .05) | 7.52 | 39.88 | 4.0345 | 1.082 | 2.4490 |
| | Standard Deviation | 5.26 | 27.91 | 2.8232 | 0.757 | 1.7137 |
| | CV | 6.24 | 82.15 | 211.5 | 124.35 | 8.61 |
| | Bartlett's x2 | 15.841 | 22.741 | 147.989 | 64.207 | 35.418 |
| | P(Bartlett's X2) | 0.393 | 0.121 | 0.001* | 0.001* | 0.003* |
| | Replicate F | 2.920 | 3.678 | 2.208 | 3.515 | 3.563 |
| | Replicate Prob(F) | 0.0439 | 0.0183 | 0.0992 | 0.0220 | 0.0208 |
| | Treatment F | 2.545 | 1.946 | 1.715 | 2.266 | 8.017 |
| | Treatment Prob(F) | 0.0069 | 0.0387 | 0.0760 | 0.0149 | 0.0001 |

Example 7

Control of Leaf Rust on Wheat

Leaf rust field trial was carried out on spring wheat cultivars. Spores from the spreader plots were served as innoculum source for the natural infection of experimental plots. Treatments were applied at heading (Feekes 10.1/10.2) using a $CO_2$-powered backpack sprayer operating at the pressure of ca. 276 kPa, fitted with flat-fan spray tip (TeeJet SS8003; Spraying Systems Co., Wheaton, Ill.), at the rate of 20 gal per acre. Prosaro (Bayer Crop Science) was used as the standard chemical control.

Disease rating was done 19 days after chemical spray. Leaf rust severity was rated as percent leaf area infected on 12 randomly selected flag leaves per plot. Data were analyzed using 'R' statistical package. Data on leaf rust severity was transformed using square root and arcsin function for analysis of variance. Means presented for rust severity in the graph and tables are back transformed mean value.

The treatments of Civitas/Harmonizer (160:10 oz/acre) and Civitas/Harmonizer (320:20 oz/acre) resulted in significantly low rust infection compared to control plots. The efficacy of Civitas treatments are at par with the chemical standard Prosaro (6.5 oz/acre).

TABLE 14

ANOVA table

| Source | DF | MS | F-value | Prob > F |
|---|---|---|---|---|
| Treatment | 12 | 6.199 | 2.617 | 0.01157 |
| Error | 39 | 2.3686 | . . . | . . . |

TABLE 15

Mean Comparisons Between Treatments:

| Treatment | Mean | Group* |
|---|---|---|
| Untreated | 2.81 | a |
| Civitas/Harmonizer - 160:10 oz/acre | 0.88 | b |
| Prosaro - 6.5 oz/acre | 0.77 | b |
| Civitas/Harmonizer - 320:20 oz/acre | 0.67 | b |

*Treatment with same letters are not statistically different

Example 8

Control of Gray Leaf Spot on Corns

Gray Leaf Spot (*Cercospora zeae-maydis*) field trial was conducted on hybrid corns (NK 67 3000GT) with natural infection. Civitas treatments were applied at R1 and R3 growth stage with the spray rate of 20 gal per acre. Headline (BASF) and Stratego (Bayer Crop Science) were applied at R1 as the standard chemical control.

Disease rating was done about 16 days and 40 days after R1 application. Gray leaf spot severity was rated as percent leaf area infected in the plots.

All of the chemical treatments resulted in lower disease severity than control plots.

TABLE 15

| No of treat-ment | Chemicals | application rate (fl.oz product/A) | Growth Stage | 16DAA % Leaf area infected | 40DAA % Leaf area infected |
|---|---|---|---|---|---|
| | untreated | | | 2.5 A | 12.0 |
| 1 | Civitas + Harmonizer | 640 40 | R1 + R3 | 1.0 C | 7.8 |
| 2 | Headline | 6 | R1 | 1.0 C | 0.8 |

TABLE 15-continued

| No of treatment | Chemicals | application rate (fl.oz product/A) | Growth Stage | 16DAA % Leaf area infected | | 40DAA % Leaf area infected |
|---|---|---|---|---|---|---|
| 3 | Stratego | 10 | R1 | 1.0 | C | 1.0 |
| | P > F | | | 0.0084 | | <.0001 |
| | LSD 0.05 | | | 0.9 | | 4.2 |
| | CV % | | | 46 | | 73 |

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way.

Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein.

The invention includes all embodiments and variations substantially as hereinbefore described and with reference to the examples. Other implementations are within the scope of the following claims.

What is claimed is:

1. A method of controlling infection of an annual crop plant by a fungal pathogen, the method comprising applying a fungicidal composition to the plant, wherein the fungicidal composition comprises a pigment and a paraffinic oil-in-water emulsion, the paraffinic oil-in-water emulsion comprising a paraffinic oil and an emulsifier.

2. The method of claim 1, wherein the crop plant is wheat, barley, soybean, or corn.

3. The method of claim 1, wherein the plant is monocotyledonous.

4. The method of claim 3, wherein the plant is of the order Poaceae.

5. The method of claim 4, wherein the plant is of the genus *Triticum, Secale, Hordeum, Oryza, Zea*, or *Elymus*.

6. The method of claim 1, wherein the fungal pathogen is of the order Pucciniales.

7. The method of claim 6, wherein the fungal pathogen is of the genus *Puccinia*.

8. The method of claim 7, wherein the fungal pathogen is of the species *Puccinia graminis, Puccinia triticina*, or *Puccinia sriiformis*.

9. The method of claim 1, wherein the fungal pathogen is selected from the group consisting of *Bipolaris sorokiniana, Fusarium graminearum*, and *Pyrenophora tritici-repentis*.

10. The method of claim 1, wherein the plant is dicotyledonous.

11. The method of claim 10, wherein the plant is of the order Fabaceae.

12. The method of claim 11, wherein the plant is of the species *Glycine max*.

13. The method of claim 10, wherein the fungal pathogen is of the genus *Phakopsora*.

14. The method of claim 13, wherein the fungal pathogen is *Phakopsora pachyrhizi* or *Phakopsora meibomiae*.

15. The method of claim 10, wherein the plant is of the genus *Gossypium*.

16. The method of claim 15, wherein the fungal pathogen is *Phakopsora gossypii*.

17. The method of claim 10, wherein the fungal pathogen is *Phytophthora infestans*.

18. The method of claim 1, wherein the paraffinic oil comprises a paraffin having a number of carbon atoms ranging from about 12 to about 50.

19. The method of claim 1, wherein the paraffinic oil has a paraffin content of at least about 80%.

20. The method of claim 1, wherein the paraffinic oil is used in a range from about 1 to about 3,200 oz/acre.

21. The method of claim 1, wherein the ratio of the paraffinic oil to the emulsifier is from 10:1 to 500:1.

22. The method of claim 21, wherein the composition comprises from 2 to 50 weight percent of the paraffinic oil.

23. The method of claim 1, wherein the fungicidal composition further comprises a demethylation inhibitor (DMI).

24. The method of claim 23, further including applying a demethylation inhibitor (DMI) at a rate of 0.015 to 0.60 lbs/acre.

25. The method of claim 23, wherein the DMI is tetraconazole, tebuconazole, propioconazole, azaconazole, bitertanol, bromuconazole, cyproconazole, difenoconazole, diniconazole, epoxiconazole, etaconazole, fenbuconazole, fluquinconazole, flusilazole, flutriafol, hexaconazole, imibenconazole, ipconazole, metconazole, myclobutanil, penconazole, prothioconazole, simeconazole, triadimefon, triadimenol, triticonazole, imazalil, oxpoconazole, pefurazoate, prochloraz, triflumizole, fenarimol, nuarimol, triforine, or pyrifenox.

26. The method of claim 1, wherein the fungicidal composition further comprises a Quinone outside Inhibitor (QoI).

27. The method of claim 21, further including applying a Quinone outside Inhibitor (QoI) to an aerial portion of the plant.

28. The method of claim 26, wherein the QoI is azoxystrobin, enestrobin, picoxystrobin, pyraclostrobin, trifloxystrobin, dimoxystrobin, metominostrobin, orysastrobin, famoxadonem, fluoxastrobin, fenamidone, or pyribencarb.

29. The method of claim 1, wherein the fungicidal composition further comprises a silicone surfactant, wherein the emulsifier, the paraffinic oil, the pigment and the silicone surfactant are present in amounts that, when applied to the plant, are synergistically effective at controlling infection by the fungal pathogen.

30. The method of claim 1, wherein the pigment is a polychlorinated (Cu II) phthalocyanine.

31. The method of claim 1, wherein the pigment is dispersed in water and the emulsifier comprises a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof.

32. The method of claim 1, wherein the pigment is dispersed in oil, the emulsifier comprises a natural or synthetic alcohol ethoxylate, a polymeric surfactant, a sorbitan fatty acid ester, or a combination thereof, and the composition further comprises a polyethylene glycol according to formula IV:

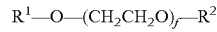

wherein R1=H or CH2=CH—CH2 or COCH3; R2=H or CH2=CH—CH2 or COCH3; and f≥1.

33. The method of claim 1, wherein the ratio of the paraffinic oil to the pigment is from 5:1 to 100:1.

34. The method of claim 1, wherein the composition further comprises an anti-settling agent.

35. The method of claim 29, wherein the weight ratio of the pigment to the silicone surfactant is from 2:1 to 50:1.

* * * * *

UNITED STATES PATENT AND TRADEMARK OFFICE
CERTIFICATE OF CORRECTION

PATENT NO.       : 9,451,773 B2
APPLICATION NO.  : 14/123716
DATED            : September 27, 2016
INVENTOR(S)      : Michael Fefer and Jun Liu It is certified that error appears in the above-identified patent and that said Letters Patent is hereby corrected as shown below:

On the Title Page

In Column 2 (Other publications), Line 6, delete "monocothtml" and insert -- monocot.html --, therefor.

In Column 2 (Other publications), Line 7, delete "Qol" and insert -- Qoi --, therefor.

In Column 2 (Other publications), Line 10, delete "U Schutte," and insert -- Schutte, --, therefor.

In Column 2 (Abstract), Line 6, delete "(Qol)" and insert -- (Qoi) --, therefor.

In the Claims

In Column 49, Line 52, Claim 8, delete "sriiformis." and insert -- striiformis. --, therefor.

In Column 50, Line 22, Claim 25, delete "propioconazole," and insert -- propiconazole, --, therefor.

In Column 50, Line 38, Claim 28, delete "enestrobin," and insert -- enestroburin, --, therefor.

In Column 50, Line 40, Claim 28, delete "famoxadonem," and insert -- famoxadone, --, therefor.

Signed and Sealed this
Sixteenth Day of January, 2018

Joseph Matal
*Performing the Functions and Duties of the
Under Secretary of Commerce for Intellectual Property and
Director of the United States Patent and Trademark Office*